(12) United States Patent
Ancliff et al.

(10) Patent No.: US 7,560,548 B2
(45) Date of Patent: *Jul. 14, 2009

(54) MORPHOLIN-ACETAMIDE DERIVATIVES FOR THE TREATMENT OF INFLAMMATORY DISEASES

(75) Inventors: Rachael Anne Ancliff, Stevenage (GB); Simon Teanby Hodgson, Stevenage (GB); Xiao Qing Lewell, Stevenage (GB); Graeme Michael Robertson, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 278 days.

This patent is subject to a terminal disclaimer.

(21) Appl. No.: 11/284,544

(22) Filed: Nov. 22, 2005

(65) Prior Publication Data

US 2006/0079525 A1 Apr. 13, 2006

Related U.S. Application Data

(63) Continuation of application No. 10/381,767, filed as application No. PCT/GB01/04345 on Sep. 28, 2001, now Pat. No. 7,101,882.

(30) Foreign Application Priority Data

Sep. 29, 2000 (GB) ................. 0023902.0
Mar. 27, 2001 (GB) ................. 0107644.7

(51) Int. Cl.
C07D 413/00 (2006.01)
(52) U.S. Cl. .................... 544/111
(58) Field of Classification Search .......... 544/111
See application file for complete search history.

(56) References Cited

U.S. PATENT DOCUMENTS 7,101,882 B2 * 9/2006 Ancliff et al. ............ 514/237.5

FOREIGN PATENT DOCUMENTS

| EP | 0243959 A | 11/1987 |
|---|---|---|
| EP | 0 243 959 B1 | 8/1992 |
| EP | 0 760 362 A1 | 3/1997 |
| EP | 0 903 349 A2 | 3/1999 |
| FR | 2 785 902 | 11/1999 |
| JP | 1 117882 | 5/1989 |
| JP | 4 208267 | 7/1992 |
| WO | 9637486 A | 11/1996 |
| WO | 9748695 A | 12/1997 |
| WO | WO 97 48397 | 12/1997 |
| WO | WO 99 55324 | 11/1999 |
| WO | WO 00 04003 | 1/2000 |
| WO | WO 00 27800 | 5/2000 |
| WO | WO 00 27835 | 5/2000 |
| WO | WO 00 27843 | 5/2000 |
| WO | WO 00 29377 | 5/2000 |
| WO | WO 00 31032 | 6/2000 |
| WO | WO 00 31033 | 6/2000 |
| WO | WO 00 34278 | 6/2000 |
| WO | WO 00/35449 | 6/2000 |
| WO | WO 00 35451 | 6/2000 |
| WO | WO 00 35452 | 6/2000 |
| WO | WO 00 35453 | 6/2000 |
| WO | WO 00 35454 | 6/2000 |
| WO | WO 00 35876 | 6/2000 |
| WO | WO 00 35877 | 6/2000 |
| WO | WO 00 41685 | 7/2000 |
| WO | WO 00 51607 | 9/2000 |
| WO | WO 00 51608 | 9/2000 |
| WO | WO 00 53172 | 9/2000 |
| WO | WO 00 53600 | 9/2000 |
| WO | 0071518 A | 11/2000 |
| WO | WO 00 71518 A2 | 11/2000 |
| WO | WO 01 14333 A1 | 3/2001 |

OTHER PUBLICATIONS

Kato, Shiro et. al., "Novel Benzamides as Selective and Potent Gastric Prokinetic Agents. 1. Synthesis and Structure-Activity Relationships of N-[(2-Morpholinyl)alkyl]benzamides," J. Med. Chem., 1990, vol. 33, pp. 1406-1413.

Wells and Schwartz, "Plagiarism of the host immune system: lessons about chemokine immunology from viruses," Curr.Opin.Biotech, 1997, vol. 4, pp. 741-748.

Choe, Hyeryun, The β-Chemokine Receptors CCR3 and CCR5 Facilitate Infection by Primary HIV-1 Isolates, Cell. vol. 85, pp. 1135-1148, Jun. 28, 1996.

Luster, Andrew D., M.D., Ph.D., "Chemokines—Chemotactic Cytrokines That Mediate Inflammation," The New England Journal of Medicine, 1998, vol. 338, pp. 436-445.

(Continued)

Primary Examiner—Rei-tsang Shiao
(74) Attorney, Agent, or Firm—James P. Riek

(57) ABSTRACT

There are provided according to the invention, novel compounds of formula (I)

(I)

$$R^1\underset{\underset{R^2}{|}}{\overset{\overset{O}{\|}}{C}}-N-X-\underset{(\ )_a}{\overset{O}{\underset{|}{\bigcirc}}}\underset{\underset{\underset{R^5}{|}}{Z}}{\overset{\underset{|}{\bigcirc}}{\underset{R^4}{\overset{}{\underset{}{\bigcirc}}}}}-R^3$$

wherein $R^1$, $R^2$, $R^3$, $R^4$, $R^5$, X, a, b and Z are as defined in the specification, processes for preparing them, formulations containing them and their use in therapy for the treatment of inflammatory diseases.

1 Claim, No Drawings

OTHER PUBLICATIONS

Gonzalo, Jose-Angel, "The Coordinated Action of CC Chemokines in the Lung Orchestrates Allergic Inflammation and Airway Hyper-responsiveness," *J. Exp. Med.*, 1998, vol. 188, pp. 157-167.

Heath, Heidi, "Chemokine Receptor Usage by Human Eosinophils," *J. Clin. Invest.*, 1997, vol. 99 (2), pp. 178-184.

Lloyd, Clare M., et. al., "CC Chemokine Receptor (CCR)3/Eotaxin Is Followed by CCR4/Monocyte-derived Cehmokine in Mediating Pulmonary T Helper Lymphocyte Type 2 Recruitment after Serial Antigen Challenge In Vitro," *J.Exp.Med.*, 2000, vol. 191 No. 2, pp. 265-273.

Griffiths-Johnson, et. al., "Eotaxin: A Potent Eosinophil Chemoattractant Cytokine Detected in a Guinea Pig Model of Allergic Airways Inflammation," *J. Exp. Chem.*, 1994, vol. 179, pp. 881-887.

Kato, et. al., "Novel benzamides as selective and potent gastrokienetic agents", *Chemical and Pharmaceutical Bulletin, Pharmaceutical Society of Japan*, vol. 40, No. 3, 1992, pp. 652-660.

Kato, et. al., "Novel benzamides as selective and potent gastrokienetic agents", *Journal of Medicinal Chemistry, American Chemical Society*, vol. 34, No. 2, 1991, pp. 616-624.

\* cited by examiner

MORPHOLIN-ACETAMIDE DERIVATIVES FOR THE TREATMENT OF INFLAMMATORY DISEASES

CROSS REFERENCES TO RELATED APPLICATIONS

This application is a continuation of U.S. patent application Ser. No. 10/381,767 filed 15 Aug. 2003, now U.S. Pat. No. 7,101,882, which is a 371 Application of PCT/GB01/04345 filed 28 Sep. 2001, which claims priority to GB 0023902.0 filed on 29 Sep. 2000, and GB 0107644.7 filed 27 Mar. 2001 both in the United Kingdom.

This invention relates to novel chemical compounds, processes for their preparation, pharmaceutical formulations containing them and their use in therapy.

Inflammation is a primary response to tissue injury or microbial invasion and is characterised by leukocyte adhesion to the endothelium, diapedesis and activation within the tissue. Leukocyte activation can result in the generation of toxic oxygen species (such as superoxide anion), and the release of granule products (such as peroxidases and proteases). Circulating leukocytes include neutrophils, eosinophils, basophils, monocytes and lymphocytes. Different forms of inflammation involve different types of infiltrating leukocytes, the particular profile being regulated by the profile of adhesion molecule, cytokine and chemotactic factor expression within the tissue.

The primary function of leukocytes is to defend the host from invading organisms, such as bacteria and parasites. Once a tissue is injured or infected, a series of events occurs which causes the local recruitment of leukocytes from the circulation into the affected tissue. Leukocyte recruitment is controlled to allow for the orderly destruction and phagocytosis of foreign or dead cells, followed by tissue repair and resolution of the inflammatory infiltrate. However in chronic inflammatory states, recruitment is often inappropriate, resolution is not adequately controlled and the inflammatory reaction causes tissue destruction. There is increasing evidence that the bronchial inflammation which is characteristic of asthma represents a specialised form of cell-mediated immunity, in which cytokine products, such as IL-4 and IL-5 released by Th2 T lymphocytes, orchestrate the accumulation and activation of granulocytes, in particular eosinophils and to a lesser extent basophils. Through the release of cytotoxic basic proteins, pro-inflammatory mediators and oxygen radicals, eosinophils generate mucosal damage and initiate mechanisms that underlie bronchial hyperreactivity. Therefore, blocking the recruitment and activation of Th2 cells and eosinophils is likely to have anti-inflammatory properties in asthma. In addition, eosinophils have been implicated in other disease types such as rhinitis, eczema, irritable bowel syndrome and parasitic infections.

Chemokines are a large family of small proteins which are involved in trafficking and recruitment of leukocytes (for review see Luster, New Eng. J. Med., 338, 436-445 (1998)). They are released by a wide variety of cells and act to attract and activate various cell types, including eosinophils, basophils, neutrophils, macrophages, T and B lymphocytes. There are two major families of chemokines, CXC-($\alpha$) and CC-($\beta$) chemokines, classified according to the spacing of two conserved cysteine residues near to the amino terminus of the chemokine proteins. Chemokines bind to specific cell surface receptors belonging to the family of G-protein-coupled seven transmembrane-domain proteins (for review see Luster, 1998). Activation of chemokine receptors results in, amongst other responses, an increase in intracellular calcium, changes in cell shape, increased expression of cellular adhesion molecules, degranulation and promotion of cell migration (chemotaxis).

To date, 9 members of CC chemokine receptors have been identified (CCR-1 to 9). Of particular importance to the current invention is the CC-chemokine receptor-3 (CCR-3), which is predominantly expressed on eosinophils, and also on basophils, mast cells and Th2 cells (Luster, 1998). Chemokines that act at CCR-3, such as RANTES, MCP-3 and MCP-4, are known to recruit and activate eosinophils. Of particular interest are eotaxin and eotaxin-2, which specifically bind to CCR-3. The localization and function of CCR-3 chemokines indicate that they play a central role in the development of allergic diseases such as asthma. Thus, CCR-3 is specifically expressed on all the major cell types involved in inflammatory allergic responses. Chemokines that act at CCR-3 are generated in response to inflammatory stimuli and act to recruit these cell types to sites of inflammation, where they cause their activation (e.g. Griffiths et al., J. Exp. Med., 179, 881-887 (1994), Lloyd et al., J. Exp. Med., 191, 265-273 (2000)). In addition, anti-CCR-3 monoclonal antibodies completely inhibit eotaxin interaction with eosinophils (Heath, H. et al., (1997) J. Clin. Invest. 99 (2), 178-184), while an antibody for the CCR-3 specific chemokine, eotaxin, reduced both bronchial hyperreactivity and lung eosinophilia in an animal model of asthma (Gonzalo et al., J. Exp. Med., 188, 157-167 (1998). Thus, many lines of evidence indicate that antagonists at the CCR-3 receptor are very likely to be of therapeutic use for the treatment of a range of inflammatory conditions.

A number of patent applications relating to CCR-3 antagonists have published before the filing date of this application. For example, EP 0 903 349, FR 2785902, WO 00129377, WO 00/31032 and WO 00/31033 (all in the name of F. Hoffmann-La-Roche AG) disclose pyrrolidine, piperidine and piperazine based compounds which are all distinct from the compounds of the present invention.

WO 99/55324, WO 00/04003, WO 00/27800, WO 00/27835, WO 00/27843, WO 00/41685 and WO 00/53172 (all in the name of SmithKline Beecham Corporation) describe a variety of compounds as CCR-3 antagonists which are unrelated to the compounds of the present invention.

WO 00/34278 (Toray Industries Inc.) describe fused triazolo derived compounds as chemokine inhibitors.

WO 00/35449, WO 00/35451, WO 00/35452, WO 00/35453, WO 00/35454, WO 00/35876 and WO 00/35877 (Du Pont Pharmaceuticals Company) describe N-ureidoalkyl and heterocyclic piperidine compounds as CCR-3 antagonists.

WO 00151607 and WO 00/51608 (Merck & Co. Inc.) describe a series of pyrrolidine modulators of chemokine receptor activity.

WO 00/53600 (Banyu Pharmaceutical Co. Ltd.) describes piperidine derivatives as inhibitors at the CCR-3 receptor.

WO 01/14333 (AstraZeneca UK Ltd.) describe substituted piperidine compounds as modulators of chemokine receptor activity.

EP 0 760 362 (Nisshin Flour Milling Co. Ltd.) describes morpholinoalkylurea derivatives which are disclosed as being useful in the treatment of digestive tract diseases.

JP 04208267A (Mitsui Seiyaku Kogyo KK) also describes morpholinoalkylurea derivatives which are disclosed as being useful as antiemetics, for activating peristalsis and ameliorating gastrointestinal function.

EP 243959A (Dainippon Pharm KK) describes O-substituted N-morpholinyl-alkyl-benzamide derivatives useful as gastrointestinal motility enhancing agents.

J0 1117-882-A (Dainippon Pharm KK) describes heterocyclic morpholinyl alkylenyl carboxamide derivatives useful as anti-emetics.

WO 00/71518 (Sepracor Inc) describes morpholinoalkylamide derivatives useful in the treatment of pain, drug addiction and tinnitus.

WO 97/48695 and WO 97/48397 (Klinge Pharma Gmbh) describe pyridyl alkane, alkene and/or alkyne acid amide compounds useful as cytostatic, immunomodulatory or immuno-suppressive agents.

Kato et al., (1992) Chem. Pharm. Bull. 40(3), 652-660, Kato et al., (1991) J. Med. Chem. 34(2), 616-624 and Kato et al., (1990) J. Med. Chem. 33(5), 1406-1413 describe a series of morpholine benzamides which are disclosed as being selective and potent gastrokinetic agents.

We have now found a novel group of CCR-3 antagonist compounds which block migration/chemotaxis of eosinophils, consequently effecting anti-inflammatory properties. These compounds are therefore of potential therapeutic benefit, especially in providing protection from eosinophil, basophil and Th2-cell-induced tissue damage in diseases where such cell types are implicated, particularly allergic diseases, including but not limited to bronchial asthma, allergic rhinitis and atopic dermatitis.

In addition to a key role in inflammatory disorders, chemokines and their receptors also play a role in infectious disease. Mammalian cytomegaloviruses, herpes viruses and pox viruses express chemokine receptor homologues, which can be activated by human CC chemokines such as RANTES and MCP-3 (for review see Wells and Schwartz, Curr. Opin. Biotech., 8, 741-748, 1997). In addition, human chemokine receptors, such as CXCR4, CCR-5 and CCR-3, can act as co-receptors for the infection of mammalian cells by microbes such as human immunodeficiency viruses (HIV). CCR-3 serves as a co-receptor for certain clinical strains of HIV-1 and facilitates viral entry (e.g Choe, H. et al, Cell, 1996, 85, 1135-1148). A key ligand for CCR-3, eotaxin, blocked the process of HIV entry. Thus, chemokine receptor antagonists, including CCR-3 antagonists, may be useful in blocking infection of CCR-3 expressing cells by HIV or in preventing the manipulation of immune cellular responses by viruses such as cytomegaloviruses.

Thus, according to one aspect of the invention, we provide compounds of formula (I):

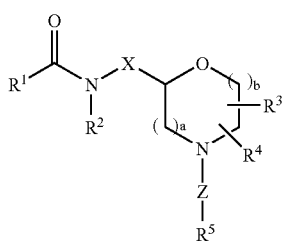

(I)

wherein:

$R^1$ represents $C_{1-6}$ alkyl, $C_{2-6}$ alkenyl, $C_{2-6}$ alkynyl, $C_{2-6}$ alkynyl-$Y^1$—, aryl-$Y^1$—, heteroaryl-$Y^1$—, aryl-$(O)_t$-aryl-$Y^1$—, aryl-$(O)_t$-heteroaryl-$Y^1$—, heteroaryl-$(O)_t$-aryl-$Y^1$—, heteroaryl-$(O)_t$-heteroaryl-$Y^1$—, $C_{2-6}$ alkenyl-$Y^1$—, aryl-O—$Y^1$—, heteroaryl-O—$Y^1$—, $C_{1-6}$ alkyl-$SO_2$—$Y^1$—, M-$Y^1$—, $J^2$-$Y^1$—, —CN or $C_{3-8}$ cycloalkyl-$Y^1$— or $C_{3-8}$ cycloalkenyl-$Y^1$—, which cycloalkyl or cycloalkenyl may be optionally substituted by one or more hydroxyl or $C_{1-6}$ alkyl groups;

$R^2$ represents hydrogen or $C_{1-6}$ alkyl;

X represents ethylene or a group of formula $CR^eR^f$ wherein $R^e$ and $R^f$ independently represent hydrogen or $C_{1-4}$ alkyl or $R^e$ and $R^f$ may together with the carbon atom to which they are attached form a $C_{3-8}$ cycloalkyl group;

$R^3$ and $R^4$ independently represent hydrogen or $C_{1-4}$ alkyl;

Z represents a bond, CO, $SO_2$, $CR^9R^6(CH_2)_n$, $(CH_2)_nCR^9R^6$, $CHR^6(CH_2)_nO$, $CHR^6(CH_2)_nS$, $CHR^6(CH_2)_nOCO$, $CHR^6(CH_2)_nCO$, $COCHR^6(CH_2)_n$ or $SO_2CHR^6(CH)_n$;

$R^5$ represents $C_{1-6}$ alkyl, $C_{2-6}$ alkenyl, aryl, heteroaryl, aryl-$C_{2-6}$ alkenyl- or a group of formula —$Y^2$-$J^1$;

$R^6$ represents hydrogen, $C_{1-4}$ alkyl, $CONR^7R^8$ or $COOC_{1-6}$ alkyl;

a and b represent 1 or 2, such that a+b represents 2 or 3;

n represents an integer from 0 to 4;

$J^1$ and $J^2$ independently represent a moiety of formula (K):

(K)

wherein $X^1$ represents oxygen, $NR^{13}$ or sulphur, $X^2$ represents $CH_2$, oxygen, $NR^{10}$ or sulphur, $m^1$ represents an integer from 1 to 3 and $m^2$ represents an integer from 1 to 3, provided that $m^1+m^2$ is in the range from 3 to 5, also provided that when both $X^1$ and $X^2$ represent oxygen, $NR^{13}$, $NR^{10}$ or sulphur, $m^1$ and $m^2$ must both not equal less than 2, wherein K is optionally substituted by one or more (eg. 1 or 2) —$Y^3$-aryl, —$Y^3$-heteroaryl, —$Y^3$—CO-aryl, —$COC_{3-8}$cycloalkyl, —$Y^3$—CO-heteroaryl, —$C_{1-6}$ alkyl, —$Y^3$—$COOC_{1-6}$ alkyl, —$Y^3$—$COC_{1-6}$ alkyl, —$Y^3$—W, —$Y^3$—CO—W, —$Y^3$—$NR^{11}R^{12}$, —$Y^3$—$CONR^{11}R^{12}$, hydroxy, oxo, —$Y^3$—$SO_2NR^{11}R^{12}$, —$Y^3$—$SO_2C_{1-6}$ alkyl, —$Y^3$—$SO_2$aryl, —$Y^3$—$SO_2$heteroaryl, —$Y^3$—$NR^{14}C_{1-6}$ alkyl, —$Y^3$—$NR^{14}SO_2C_{1-6}$ alkyl, —$Y^3$—$NR^{14}CONR^{11}R^{12}$, —$Y^3$—$NR^{14}COOR^{15}$ or —$Y^3$—$OCONR^{11}R^{12}$ groups, and is optionally fused to a monocyclic aryl or heteroaryl ring;

$R^7$, $R^8$, $R^9$, $R^{10}$, $R^{13}$, $R^{14}$ and $R^{15}$ independently represent hydrogen or $C_{1-6}$ alkyl;

$R^{11}$ and $R^{12}$ independently represent hydrogen or $C_{1-6}$ alkyl or $R^{11}$ and $R^{12}$ together with the nitrogen atom to which they are attached may form a morpholine, piperidine or pyrrolidine ring;

M represents a $C_{3-8}$ cycloalkyl or a $C_{3-8}$ cycloalkenyl group fused to a monocyclic aryl or monocyclic heteroaryl group;

W represents a saturated or unsaturated, non-aromatic 5-7 membered ring containing between 1 and 3 heteroatoms selected from nitrogen, oxygen or sulphur, optionally substituted with one or more $C_{1-6}$ alkyl, halogen or hydroxy groups;

t represents 0 or 1.

$Y^1$, $Y^2$ and $Y^3$ independently represent a bond or a group of formula —$(CH_2)_pCR^cR^d(CH_2)_q$— wherein $R^c$ and $R^d$ independently represent hydrogen or $C_{1-4}$ alkyl or $R^c$ and $R^d$ may together with the carbon atom to which they are attached form a $C_{3-8}$ cycloalkyl group, and p and q independently represent an integer from 0 to 5 wherein p+q is an integer from 0 to 5;

and salts and solvates thereof.

Specific groups of compounds of formula (I) which may be mentioned are those as defined above with the proviso that the compound of formula (I) is not a compound of formula (I)$^a$:

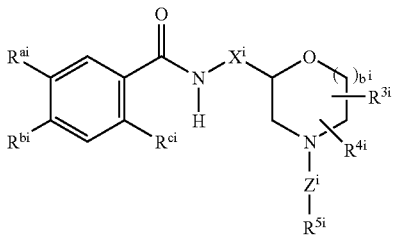

wherein $R^{ai}$ represents hydrogen, halogen, nitro, $SO_2NH_2$, or mono- or di-($C_{1-4}$ alkylsulphamoyl; $R^{bi}$ represents hydrogen, halogen, amino, nitro, —$N(CH_3)_2$ or $C_{2-5}$ alkanoylamino (provided that at least one of $R^{ai}$ and $R^{bi}$ is not hydrogen); $R^{ci}$ represents halogen, hydroxy, $C_{1-6}$ alkoxy, cyano, $C_{3-6}$ cycloalkyl, —$SCH_3$, amino or $C_{2-5}$ alkoxycarbonyl; $X^i$ represents methylene or ethylene; $b^i$ represents 1 or 2; $R^{3i}$ and $R^{4i}$ represent hydrogen or $C_{1-4}$ alkyl; and wherein the moiety -$Z^i$-$R^{5i}$ represents heteroaryl$C_{1-3}$ alkyl (wherein heteroaryl represents furyl, thienyl, pyridyl or 1,2-benzisoxazolyl), phenyl-$C_{3-5}$ alkenyl, naphthyl, —$C_{1-5}$ alkylenenaphthyl, —$C_{1-5}$ alkyleneonaphthyl, —$C_{1-5}$ alkyleneCOnaphthyl, phenyl, —$C_{1-5}$ alkylenephenyl, —$C_{1-5}$ alkyleneophenyl or —$C_{1-5}$ alkyleneCOphenyl (wherein phenyl is substituted by one to five members each independently selected from the group consisting of a halogen, $C_{1-4}$ alkyl, trifluoromethyl, $C_{1-4}$ alkoxy, nitro, cyano or amino) (compounds of formula (I)$^a$ are described in EP0243959A1); and/or the proviso that the compound of formula (I) is not a compound of formula (I)$^b$:

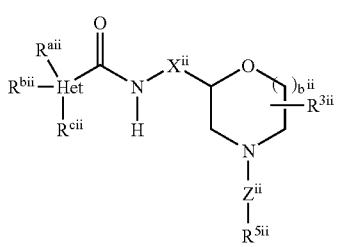

wherein Het represents a heteroaryl moiety; $R^{aii}$, $R^{bii}$ and $R^{cii}$ represent hydrogen, halogen, $C_{1-6}$ alkyl, $C_{1-6}$ alkoxy, amino or $NMe_2$; $X^{ii}$ represents methylene or ethylene; $R^{3ii}$ represents hydrogen or $C_{1-4}$ alkyl; $b^{ii}$ represents 1 or 2; and wherein the moiety -$Z^{ii}$-$R^{5ii}$ represents optionally substituted aryl-$C_{1-5}$ alkyl- (compounds of formula (I)$^b$ are described in J01117-882A); and/or the proviso that the compound of formula (I) is not a compound of formula (I)$^c$:

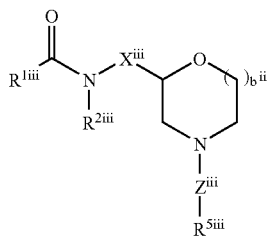

wherein $R^{1iii}$ represents $C_{1-6}$ alkyl, $C_{3-8}$ cycloalkyl, heteroaryl or aryl; $R^{2iii}$ represents $C_{1-6}$ alkyl; $X^{iii}$ represents ethylene or a group of formula $CR^{eiii}R^{fiii}$ wherein $R^{eiii}$ and $R^{fiii}$ independently represent hydrogen or $C_{1-4}$ alkyl; $R^{3iii}$ represents hydrogen or $C_{1-4}$ alkyl; $b^{iii}$ represents 1 or 2; $Z^{iii}$ represents $CR^{9iii}R^{6iii}(CH_2)_{niii}$ (wherein $R^{6iii}$ represents hydrogen or $C_{1-4}$ alkyl and $R^{9iii}$ represents hydrogen or $C_{1-6}$ alkyl and niii represents 0 to 3); and $R^{5iii}$ represents $C_{1-6}$ alkyl, aryl, heteroaryl or $C_{2-6}$ alkenyl (compounds of formula (I)$^c$ are described in WO00/71518A2); and/or the proviso that the compound of formula (I) is not a compound of formula (I)$^d$:

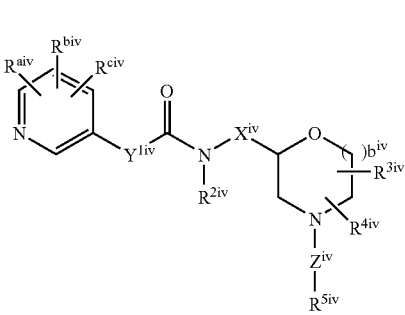

wherein $R^{aiv}$ represents hydrogen, halogen, —CN, —$CF_3$, —OH, —$CONH_2$, —COOH, $C_{1-6}$ alkyl, —$C_{2-6}$ alkenyl, —$C_{1-6}$ alkoxy, —$SCH_3$, $C_{3-8}$ cycloalkyl, —$COOC_{1-6}$ alkyl, —$NHCOC_{1-6}$ alkyl, —$CON(C_{1-6}$ alkyl$)_2$, —$N(CH_3)_2$; $R^{biv}$ represents hydrogen, halogen, —CN, OH, —$CF_3$, $C_{1-6}$ alkyl or $C_{1-6}$ alkoxy; $R^{civ}$ represents hydrogen, halogen, $C_{1-6}$ alkyl, —$CF_3$; $Y^{1iv}$ represents $C_{1-6}$ alkylene; $R^{2iv}$ represents hydrogen or $C_{1-6}$ alkyl; $X^{iv}$ represents methylene or ethylene; $R^{3iv}$ represents hydrogen or $C_{1-4}$ alkyl; $R^{4iv}$ represents hydrogen or $C_{1-4}$ alkyl; $b^{iv}$ represents 2; $Z^{iv}$ represents $CR^{9iv}R^{6iv}(CH_2)_{niv}$, $CHR^{6iv}(CH_2)_{niv}CO$ (wherein $R^{6iv}$ represents hydrogen or $C_{1-4}$ alkyl and $R^{9iv}$ represents hydrogen or methyl and niv represents 0 to 3) or $SO_2CHR^{6iv}(CH_2)_{niv}$ (wherein $R^{6iv}$ represents hydrogen and niv represents 0); and $R^{5iv}$ represents $C_{1-6}$ alkyl, $C_{3-6}$ alkenyl, phenyl, $J^1$ or heteroaryl (wherein said phenyl or heteroaryl may be optionally substituted by 1-3 halogen, CN, $C_{1-6}$ alkyl, —$CF_3$, $C_{3-8}$ cycloalkyl, hydroxy, $C_{1-6}$ alkoxy, —$SCH_3$, COOH, $COOC_{1-6}$ alkyl, nitro, amino or —$N(CH_3)_2$) (compounds of formula (I)$^d$ are described in WO97/48695A1 and WO97/48397A1); and/or the proviso that the compound of formula (I) is not a compound of formula (I)$^e$:

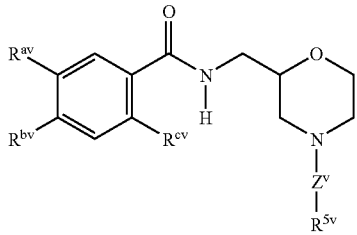

(I)$^e$ wherein R$^{av}$ represents chlorine; R$^{bv}$ represents amino; R$^{cv}$ represents methoxy or ethoxy; and the moiety -Z$^v$R$^{5v}$ represents phenyl or C$_{1-6}$ alkyl (such compounds of formula (I)$^e$ are described in Kato et al., (1992) Chem. Pharm. Bull. 40(3), 652-660);

also wherein R$^{av}$ represents chlorine; R$^{bv}$ represents amino; R$^{cv}$ represents methoxy or ethoxy; and the moiety -Z$^v$-R$^{5v}$ represents —CH$_2$-phenyl wherein phenyl is substituted by 2-, 3- or 4-chloro, 2-, 3- or 4-fluorine, 3- or 4-CF$_3$, 3- or 4-methoxy, 4-methyl, 4-nitro, 4-amino, 4-carboxymethyl, 3- or 4-cyano, 3,4-dichloro, 2,4-difluoro, 3,4-difluoro, 3,5-difluoro, 2,4,6-trimethyl (such compounds of formula (I)$^e$ are described in Kato et al., (1991) J. Med. Chem. 34(2), 616-624);

also wherein R$^{av}$ represents hydrogen, bromine, chlorine, nitro or SO$_2$NH$_2$; R$^{bv}$ represents amino, —NMe$_2$, —NEt$_2$ or —NHCOCH$_3$; R$^{cv}$ represents methoxy, ethoxy, hydroxy or chlorine; and the moiety -Z$^v$-R$^{5v}$ represents —CH$_2$-phenyl (such compounds of formula (I)$^e$ are described in Kato et al., (1990) J. Med. Chem. 33(5), 1406-1413).

A preferred set of compounds of formula (I) include compounds wherein R$^1$ represents C$_{1-6}$ alkyl, C$_{2-6}$ alkenyl, C$_{2-6}$ alkynyl, C$_{2-6}$ alkynyl-Y$^1$—, aryl-Y$^1$—, heteroaryl-Y$^1$—, aryl-(O)$_t$-aryl-Y$^1$—, aryl-(O)$_t$-heteroaryl-Y$^1$—, heteroaryl-(O)$_t$-aryl-Y$^1$—, heteroaryl-(O)$_t$-heteroaryl-Y$^1$—, C$_{2-6}$ alkenyl-Y$^1$—, aryl-O—Y$^1$—, heteroaryl-O—Y$^1$—, C$_{1-6}$ alkyl-SO$_2$—Y$^1$—, M-Y$^1$— or C$_{3-8}$ cycloalkyl-Y$^1$— or C$_{3-8}$ cycloalkenyl-Y$^1$—, which cycloalkyl or cycloalkenyl may be optionally substituted by one or more hydroxyl or C$_{1-6}$ alkyl groups; and J$^1$ represents a moiety of formula (K):

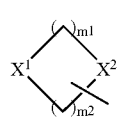

(K)

wherein X$^1$ represents oxygen, NR$^{13}$ or sulphur, X$^2$ represents CH$_2$, oxygen, NR$^{10}$ or sulphur, m$^1$ represents an integer from 1 to 3 and m$^2$ represents an integer from 1 to 3, provided that m$^1$+m$^2$ is in the range from 3 to 5, also provided that when both X$^1$ and X$^2$ represent oxygen, NR$^{13}$, NR$^{10}$ or sulphur, m$^1$ and m$^2$ must both not equal less than 2, wherein K is optionally substituted by one or more (eg. 1 or 2) —Y$^3$-aryl, —Y$^3$-heteroaryl, —Y$^3$—CO-aryl, —Y$^3$—CO-heteroaryl, —C$_{1-8}$ alkyl, —Y$^3$—COOC$_{1-6}$ alkyl, —Y$^3$—COC$_{1-6}$ alkyl, —Y$^3$—W, —Y$^3$—CO—W, —Y$^3$—NR$^{11}$R$^{12}$$_1$, —Y$^3$—CONR$^{11}$R$^{12}$, hydroxy, oxo, —Y$^3$—SO$_2$NR$^{11}$R$^{12}$, —Y$^3$—SO$_2$C$_{1-6}$ alkyl, —Y$^3$—O$_2$aryl, —Y$^3$—SO$_2$heteroaryl, —Y$^3$—NR$^{14}$C$_{1-6}$ alkyl, —Y$^3$—NR$^{14}$SO$_2$C$_{1-6}$ alkyl, —Y$^3$—NR$^{14}$CONR$^{11}$R$^{12}$, —Y$^3$—NR$^{14}$COOR$^{15}$ or —Y$^3$—OCONR$^{11}$R$^{12}$ groups, and is optionally fused to a monocyclic aryl or heteroaryl ring.

A preferred subset of compounds of formula (I) include compounds wherein R$^1$ represents C$_{1-6}$ alkyl, C$_{2-6}$ alkenyl, C$_{2-6}$alkynyl, aryl-Y$^1$—, heteroaryl-Y$^1$—, aryl-(O)$_t$-aryl-Y$^1$—, aryl-(O)$_t$-heteroaryl-Y$^1$—, heteroaryl-(O)$_t$-aryl-Y$^1$—, heteroaryl-(O)$_t$-heteroaryl-Y$^1$—, C$_{2-6}$ alkenyl-Y$^1$—, aryl-O—Y$^1$—, heteroaryl-O—Y$^1$—, C$_{1-6}$ alkyl-SO$_2$—Y$^1$—, M-Y$^1$— or C$_{3-8}$ cycloalkyl-Y$^1$— or C$_{3-8}$ cycloalkenyl-Y$^1$—, which cycloalkyl or cycloalkenyl may be optionally substituted by one or more hydroxyl or C$_{1-6}$ alkyl groups;

Z represents a bond, CO, CR$^9$R$^6$(CH$_2$)$_n$, CHR$^6$(CH$_2$)$_n$O, CHR$^6$(CH$_2$)$_n$S, CHR$^6$(CH$_2$)$_n$OCO, CHR$^6$(CH$_2$)$_n$CO; and J$^1$ represents a moiety of formula (K):

(K)

wherein X$^1$ represents oxygen, nitrogen, NR$^{13}$ or sulphur, X$^2$ represents CH$_2$, oxygen, nitrogen, NR$^{10}$ or sulphur, m$^1$ represents an integer from 1 to 3, m$^2$ represents an integer from 1 to 3, provided that m$^1$+m$^2$ is in the range from 3 to 5, also provided that when X$^2$ represents oxygen, nitrogen, NR$^{10}$ or sulphur, m$^1$ and m$^2$ must both not equal less than 2, wherein K is optionally substituted by one or more (eg. 1 or 2) —Y$^3$-aryl, —Y$^3$-heteroaryl, —Y$^3$—CO-aryl, —Y$^3$—CO-heteroaryl, —C$_{1-6}$ alkyl, —Y$^3$—COOC$_{1-6}$ alkyl, —Y$^3$—COC$_{1-6}$ alkyl, —Y$^3$—W, —Y$^3$—CO—W, —Y$^3$—NR$^{11}$R$^{12}$, —Y$^3$—CONR$^{11}$R$^{12}$, hydroxy, oxo, —Y$^3$—SO$_2$NR$^{11}$R$^{12}$, —Y$^3$—SO$_2$C$_{1-6}$ alkyl, —Y$^3$—SO$_2$aryl, —Y$^3$—SO$_2$heteroaryl, —Y$^3$—NR$^{14}$C$_{1-6}$ alkyl, —Y$^3$—NR$^{14}$SO$_2$C$_{1-6}$ alkyl, —Y$^3$—NR$^{14}$CONR$^{11}$R$^{12}$, —Y$^3$—NR$^{14}$COOR$^{15}$ or —Y$^3$—OCONR$^{11}$R$^{12}$ groups, and is optionally fused to a monocyclic aryl or heteroaryl ring.

References to 'aryl' include references to monocyclic carbocyclic aromatic rings (eg. phenyl) and bicyclic carbocyclic aromatic rings (e.g. naphthyl) and references to 'heteroaryl' include references to mono- and bicyclic heterocyclic aromatic rings containing 1-3 hetero atoms selected from nitrogen, oxygen and sulphur. References to 'heteroaryl' may also be extended to include references to mono- and bicyclic heterocyclic aromatic rings containing 4 hetero atoms selected from nitrogen, oxygen and sulphur. Examples of monocyclic heterocyclic aromatic rings include e.g. pyridinyl, pyrimidinyl, thiophenyl, furanyl, pyrrolyl, oxazolyl, isoxazolyl, oxadiazolyl, thiazolyl, thiadiazolyl, imidazolyl. Further examples of monocyclic heterocyclic aromatic rings include pyrazinyl or tetrazolyl. Examples of bicyclic heterocyclic aromatic rings include eg. benzimidazolyl, quinolinyl or indolyl. Further examples of bicyclic heterocyclic aromatic rings include eg. benzotriazolyl, pyrrolopyridine, benzothiazolyl and quinoxalinyl. Carbocyclic and heterocyclic aromatic rings may be optionally substituted, e.g. by one or more C$_{1-6}$ alkyl, C$_{2-6}$ alkenyl, halogen, C$_{1-6}$ alkoxy, cyano, hydroxy, nitro, amino, W, —N(CH$_3$)$_2$, —NHCOC$_{1-6}$ alkyl, —OCF$_3$, —CF$_3$, —COOC$_{1-6}$ alkyl, —OCHF$_2$, —SCF$_3$, —SO$_2$N(CH$_3$)$_2$, —SO$_2$CH$_3$, —SCH$_3$, —CONR$^{16}$R$^{17}$ or —SO$_2$NR$^{16}$R$^{17}$ groups (wherein R$^{16}$ and R$^{17}$ independently represent hydrogen or $C_{1-6}$ alkyl; $R^{16}$ and $R^{17}$ may also independently represent $C_{3-8}$ cycloalkyl). Further substituents of carbocyclic and heterocyclic aromatic rings include —COOH and —NHSO$_2$CH$_3$. Yet further substituents include —N(C$_{1-6}$alkyl)SO$_2$C$_{1-6}$alkyl, —N(SO$_2$C$_{1-6}$alkyl)$_2$, —NHCOCH$_2$N(C$_{1-6}$alkyl)$_2$, —NHCONHC$_{1-6}$alkyl, —CONH(CH$_2$)$_2$OC$_{1-6}$alkyl, —CONH(CH$_2$)$_2$N(C$_{1-6}$alkyl)$_2$, CON(C$_{1-6}$alkyl)$_2$, C$_{3-8}$cycloalkyl, morpholinyl, —COmethylpiperazinyl and COmorpholinyl.

Examples of group $J^1$ include indolinyl, which may be optionally substituted.

Examples of group $J^2$ include thiomorpholinyl and piperidinyl, which may be optionally substituted, for example by t-butoxycarbonyl.

Examples of group M include tetrahydronaphthalenyl.

Examples of group W include piperidinyl, pyrrolidinyl, morpholinyl and piperazinyl which may be optionally substituted.

References to alkyl include references to both straight chain and branched chain aliphatic isomers of the corresponding alkyl. It will be appreciated that references to alkylene and alkoxy shall be interpreted similarly.

References to $C_{3-8}$ cycloalkyl include references to all alicyclic (including branched) isomers of the corresponding alkyl.

Preferably, $R^1$ represents $C_{1-6}$ alkyl (particularly butyl and —(CH$_2$)$_2$CH(CH$_3$)$_2$), $C_{2-6}$ alkenyl, $C_{2-6}$ alkynyl, aryl-Y$^1$—, heteroaryl-Y$^1$—, aryl-(O)$_t$-aryl-Y$^1$—, aryl-(O)$_t$-heteroaryl-Y$^1$— (particularly wherein aryl represents phenyl and heteroaryl represents tetrazolyl, oxadiazolyl, thiazolyl or oxazolyl), heteroaryl-(O)$_t$-aryl-Y$^1$—, heteroaryl-(O)$_t$-heteroaryl-Y$^1$— (particularly wherein heteroaryl represents oxazolyl, thiazolyl, thiophenyl, pyrazolyl, pyrazinyl, furanyl, pyridinyl or tetrazolyl), $C_{2-6}$ alkenyl-Y$^1$—, aryl-O—Y$^1$— (particularly wherein aryl represents phenyl), heteroaryl-O—Y$^1$—, $C_{1-6}$ alkyl-SO$_2$—Y$^1$— (particularly wherein C$_{1-6}$ alkyl represents methyl), M-Y$^1$—, —CN, J$^2$-Y$^1$— or C$_{3-8}$ cycloalkyl-Y$^1$— (particularly cyclopropyl and cyclohexyl) or C$_{3-8}$ cycloalkenyl-Y$^1$—, which cycloalkyl or cycloalkenyl may be optionally substituted by one or more hydroxyl or C$_{1-6}$ alkyl groups.

Particularly, $R^1$ represents $C_{1-6}$ alkyl, $C_{2-6}$ alkenyl, $C_{2-6}$ alkynyl, aryl-Y$^1$—, heteroaryl-Y$^1$—, aryl-(O)$_t$-aryl-Y$^1$—, aryl-(O)$_t$-heteroaryl-Y$^1$—, heteroaryl-(O)$_t$-aryl-Y$^1$—, heteroaryl-(O)$_t$-heteroaryl-Y$^1$—, $C_{2-6}$ alkenyl-Y$^1$—, aryl-O—Y$^1$—, heteroaryl-O—Y$^1$—, $C_{1-6}$ alkyl-SO$_2$—Y$^1$—, M-Y$^1$— or $C_{3-8}$ cycloalkyl-Y$^1$— or $C_{3-8}$ cycloalkenyl-Y$^1$—, which cycloalkyl or cycloalkenyl may be optionally substituted by one or more hydroxyl or C$_{1-6}$ alkyl groups.

More preferably, $R^1$ represents aryl-Y$^1$—, aryl-O—Y$^1$—, heteroaryl-Y$^1$—, aryl-(O)$_t$-heteroaryl-Y$^1$— or heteroaryl-(O)$_t$-heteroaryl-Y$^1$—, especially aryl-Y$^1$—, heteroaryl-Y$^1$, heteroaryl-(O)$_t$-heteroaryl-Y$^1$— or aryl-(O)$_t$-heteroaryl-Y$^1$—. In this definition, aryl preferably represents phenyl optionally substituted by one or more —SO$_2$—N(CH$_3$)$_2$, —SO$_2$CH$_3$, halogen (especially fluorine or chlorine), C$_{1-6}$ alkyl (especially methyl), CH$_3$CONH—, —CF$_3$, CH$_3$O—, —CONH$_2$, (CH$_3$)$_2$N— or —SCH$_3$ groups. Further preferred phenyl substituents include —NHSO$_2$CH$_3$, —COOH, —COOCH$_3$ and —CONH-cyclopropyl. Yet further preferred phenyl substituents include —SO$_2$NHcyclopropyl, —SO$_2$NHCH$_2$CH$_3$, —SO$_2$NHCH$_3$, —N(CH$_3$)SO$_2$CH$_3$, —N(SO$_2$CH$_3$)$_2$, —NHCOCH$_2$N(CH$_3$)$_2$, —NHCOCH(CH$_3$)$_2$, —NH$_2$, —SO$_2$NH$_2$, —NHCONHCH$_3$, —NO$_2$, —CONH(CH$_2$)$_2$OCH$_3$, —CONHCH(CH$_3$)$_2$, —CONH(CH$_2$)$_2$OH, —CONH(CH$_2$)$_2$N(CH$_3$)$_2$, —CON(CH$_3$)$_2$, —CONHCH$_2$CH$_3$, —CONHCH$_3$, —COCH$_3$, —COCH(CH$_3$)$_2$, —CN, —OH, —CO-4-methyl-1-piperazinyl and —COmorpholinyl. Heteroaryl preferably represents indolyl, thiophenyl, oxazolyl, pyrazolyl, thiazolyl, pyrimidinyl or furanyl optionally substituted with one or more C$_{1-6}$ alkyl (especially methyl), CH$_3$O— or halogen (especially bromine) groups. Heteroaryl also preferably represents tetrazolyl or pyrazinyl. Further preferred groups which heteroaryl may represent include benzotriazolyl, pyrrolopyridine, benzothiazolyl, pyridinyl, quinoxalinyl and imidazolyl. Suitable heteroaryl substituents include halogen (especially bromine), —COCH$_3$, —COOCH$_3$, —CH$_3$, —CH(CH$_3$)$_2$, morpholinyl, cyclopropyl, —CH$_2$CH(CH$_3$)$_2$ and —CH=C(CH$_3$)$_2$.

A most particularly preferred group of compounds are those in which $R^1$ is aryl-(O)$_t$-heteroaryl-Y$^1$— especially wherein heteroaryl represents optionally substituted oxazolyl, (especially oxazolyl substituted by methyl), aryl represents phenyl and t represents 0.

Especially preferred $R^1$ is aryl-Y$^1$—, particularly when aryl represents phenyl optionally substituted by any of the above substituents, most especially phenyl substituted by —SO$_2$NH$_2$.

Preferably, $Y^1$ represents a bond, $C_{1-6}$ alkylene, $C_{3-8}$ cycloalkyl or —CHCH$_3$, particularly $C_{1-6}$ alkylene or $C_{3-8}$ cycloalkyl, most preferably methylene, ethylene or cyclopropyl, especially methylene or cyclopropyl, most especially methylene.

Preferably, $R^2$ represents hydrogen.

Preferably, X represents methylene.

Preferably, $R^3$ and $R^4$ independently represent hydrogen or methyl, especially hydrogen.

Preferably, Z represents a bond, CO, CR$^9$R$^6$(CH$_2$)$_n$, CHR$^6$(CH$_2$)$_n$O, CHR$^6$(CH$_2$)$_n$S, CHR$^6$(CH$_2$)$_n$OCO or CHR$^6$(CH$_2$)$_n$CO.

More preferably, Z represents a bond, CO, CHR$^6$(CH$_2$)$_n$, CHR$^6$(CH$_2$)$_n$O (particularly (CH$_2$)$_2$O) or CHR$^6$(CH$_2$)$_n$CO, more particularly CHR$^6$(CH$_2$)$_n$ or CHR$^6$(CH$_2$)$_n$CO, most preferably CH$_2$, (CH$_2$)$_3$, CHCH$_3$or CH$_2$CO, especially CH$_2$ or CH$_2$CO, most especially CH$_2$.

Preferably, $R^5$ represents $C_{2-6}$ alkenyl (particularly —CH$_2$CH(CH$_3$)=CH$_2$), aryl, heteroaryl or a group of formula —Y$^2$-J$^1$, more preferably aryl, heteroaryl or a group of formula —Y$^2$-J$^1$, most preferably monocyclic aryl, heteroaryl or a group of formula —Y$^2$-J$^1$, especially aryl or —Y$^2$-J$^1$, particularly phenyl which may be optionally substituted. We also especially prefer $R^5$ to represent heteroaryl, particularly thiophenyl which may be optionally substituted. Other groups which heteroaryl preferably represents include benzoxadiazolyl, benzothiadiazolyl or benzothiophenyl which may be optionally substituted. We most particularly prefer $R^5$ to represent phenyl optionally substituted by one or more (eg. 1, 2 or 3) halogen groups. Other preferred substituents for phenyl include —CN and —CF$_3$. We also most particularly prefer $R^5$ to represent thiophenyl optionally substituted by one or more (eg. 1, 2 or 3) halogen groups.

Especially preferred $R^5$ groups are dichlorophenyl, difluorophenyl, fluorophenyl, chlorothiophenyl, chlorophenyl and trifluorophenyl, most especially dichlorophenyl, difluorophenyl, fluorophenyl and chlorothiophenyl.

Most preferred $R^5$ is dichlorophenyl (particularly 3,4-dichlorophenyl, 2,3-dichlorophenyl and 2,5-dichlorophenyl), 4-fluorophenyl and 3,4-difluorophenyl.

Most especially preferred $R^5$ is dichlorophenyl, particularly 3,4-dichlorophenyl.

Preferably, $y^2$ represents a bond.

Preferably, $J^1$ represents indolinyl, particularly indolin-1-yl.

Preferably, $J^2$ represents optionally substituted piperidinyl (particularly piperidinyl substituted by —$COOC_{1-6}$alkyl eg. —$COOC(CH_3)_3$) or thiomorpholinyl (particularly dioxidothiomorpholinyl) or dioxidothiomorpholinyl.

Preferably, $Y^3$ represents a bond.

Preferably, $R^3$ represents hydrogen.

Preferably, $R^7$ and $R^8$ represent hydrogen.

Preferably, $R^9$ represents hydrogen.

Preferably, $R^{10}$ and $R^{13}$ independently represent hydrogen or methyl, especially hydrogen.

Preferably, $R^{11}$ and $R^{12}$ independently represent hydrogen or methyl or $R^{11}$ and $R^{12}$ together with the nitrogen atom to which they are attached may form a morpholine, piperidine or pyrrolidine ring, especially hydrogen or methyl.

Preferably, $R^{14}$ and $R^{15}$ independently represent hydrogen or methyl.

Preferably, $R^{16}$ and $R^{17}$ independently represent hydrogen, methyl, ethyl, isopropyl, 2-hydroxyethyl, 2-methoxyethyl, cyclopropyl or 2-(dimethylamino)ethyl. Most preferably, $R^{16}$ and $R^{17}$ independently represent hydrogen or cyclopropyl.

Preferably, $R^c$ and $R^d$ independently represents hydrogen or methyl, most preferably hydrogen or $R^c$ and $R^d$ together with the carbon atom to which they are attached preferably forms cyclopropyl.

Preferably, $R^e$ and $R^f$ both represent hydrogen.

Preferably, a and b both represent 1.

Preferably, n represents 0, 1 or 2, more preferably 0.

Preferably, p and q independently represent 0 or 1 such that p+q represent 0-1.

Most preferably, p and q both represent 0.

Preferably, t represents 0.

Preferably, W represents pyrrolidinyl or piperidinyl, especially pyrrolidinyl.

Preferably, $X^1$ represents sulphur, oxygen or $NR^{11}$. More preferably, $X^1$ represents oxygen or $NR^{11}$.

Preferably, $X^2$ represents $CH_2$, oxygen or $NR^{12}$.

Preferably, $m^1$ and $m^2$ independently represent an integer from 1 to 2, such that $m^1+m^2$ is in the range from 3 to 4.

Suitable salts of the compounds of formula (I) include physiologically acceptable salts and salts which may not be physiologically acceptable but may be useful in the preparation of compounds of formula (I) and physiologically acceptable salts thereof. If appropriate, acid addition salts may be derived from inorganic or organic acids, for example hydrochlorides, hydrobromides, sulphates, phosphates, acetates, benzoates, citrates, succinates, lactates, tartrates, fumarates, maleates, 1-hydroxy-2-naphthoates, palmoates, methanesulphonates, formates or trifluoroacetates. Examples of solvates include hydrates.

When compounds of formula (I) contain chiral centres, the invention extends to mixtures of enantiomers (including racemic mixtures) and diastereoisomers as well as to individual enantiomers. Generally it is preferred to use a compound of formula (I) in the form of a single enantiomer.

The compounds of formula (I) and salts and solvates thereof may be prepared by the methodology described hereinafter, constituting a further aspect of this invention.

A process according to the invention for preparing a compound of formula (I) which comprises:

(a) acylation of a compound of formula (II)

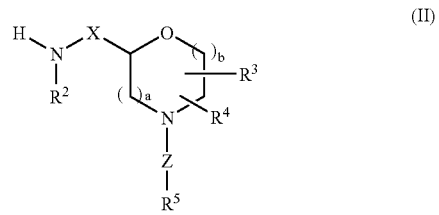

or a protected derivative thereof wherein $R^2$, $R^3$, $R^4$, $R^5$, X, Z, a and b are as described above, with a compound of formula $R^1COOH$ or an activated derivative thereof, wherein $R^1$ is as described above; or (b) reacting a compound of formula (III)

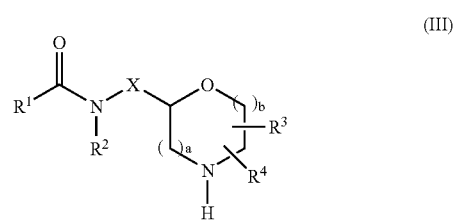

or a protected derivative thereof wherein $R^1$, $R^2$, $R^3$, $R^4$, X, a and b are as defined above, with a compound of formula $L^1$-Z-$R^5$, wherein Z and $R^5$ are as defined above and $L^1$ represents a suitable leaving group; or (c) deprotecting a compound of formula (I) which is protected; or (d) interconversion of other compounds of formula (I).

We also provide a further process according to the invention for preparing a compound of formula (I) which comprises:

(e) forming a compound of formula (I) wherein $R^1$ represents heteroaryl-$Y^1$—, aryl-(O)$_t$-heteroaryl-$Y^1$— or heteroaryl-(O)$_t$-heteroaryl-$Y^1$— (wherein said $Y^1$ group is attached to heteroaryl via a heterocyclic nitrogen atom) and $R^2$ represents hydrogen which comprises reacting a compound of formula (IV)

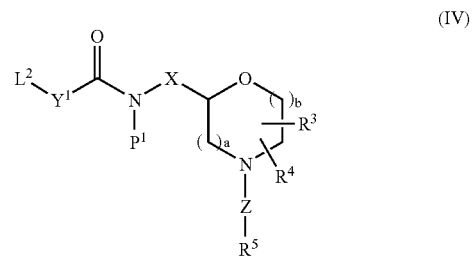

or a protected derivative thereof wherein $R^3$, $R^4$, $R^5$, X, $Y^1$, Z, a and b are as defined above, $L^2$ represents a suitable leaving group, such as a halogen atom eg. bromine and $P^1$ represents a solid phase resin bound protecting group, such as one described for process (c), with a heterocyclic compound defined by the $R^1$ groups heteroaryl, aryl-(O)$_t$-heteroaryl or heteroaryl-(O)$_t$-heteroaryl above wherein said heteroaryl group contains at least one NH atom, followed by removal of the solid phase resin bound protecting group; or (f) forming a compound of formula (I) wherein Z represents CR⁹R⁶(CH₂)ₙ and R⁹ represents hydrogen which comprises reacting a compound of formula (III) or a protected derivative thereof with a compound of formula R⁶CO (CH₂)ₙR⁵, followed by reduction of the resultant imine; or (g) forming a compound of formula (I) wherein Z represents CO by reacting a compound of formula (III) or a protected derivative thereof with a compound of formula R⁵COOH or an activated derivative thereof.

Process (a) may be effected simply by the reaction of a compound of formula (II) with R¹COOH which may typically be achieved using an oven eg. a microwave oven at a power of 600 W for 4 minutes. Examples of activated derivatives of R¹COOH which may be employed in this reaction include acid halides and anhydride derivatives (eg. the acid chloride). Alternatively, process (a) may be performed in the presence of O-(7-azabenzotriazol-1-yl)-N,N,N',N'-tetramethylammonium hexafluorophosphate (HATU) and a suitable base, eg. N,N-diisopropylethylamine in a suitable solvent, eg. N,N-dimethylformamide at a suitable temperature, eg. room temperature. Process (a) may also be performed in the presence of 1-hydroxybenzotriazole and 1-(3-dimethylaminopropyl)-3-ethylcarbodiimide hydrochloride in the presence of a suitable base, eg. N,N-diisopropylethylamine and a suitable solvent, eg. dichloromethane or N,N-dimethylformamide, at a suitable temperature, eg. room temperature. Further, process (a) may be performed in the presence of 1,1'-carbonyldiimidazole in the presence of a suitable solvent, eg. N,N-dimethylformamide at a suitable temperature, eg. room temperature. Process (a) may also be performed in the presence of a suitable base such as polyvinylpyridine and a suitable solvent, such as dichloromethane at a suitable temperature such as room temperature.

Process (b) may be performed in the presence of a suitable solvent eg. N,N-dimethylformamide, optionally in the presence of N,N-diisopropylethylamine at a suitable temperature eg. room temperature. Examples of suitable leaving groups (L¹) include halogen, eg. chlorine.

In process (c), examples of protecting groups and the means for their removal can be found in T. W. Greene and P. G. M. Wuts 'Protective Groups in Organic Synthesis' (J. Wiley and Sons, 3rd Ed. 1999). Suitable amine protecting groups include sulphonyl (e.g. tosyl), acyl (e.g. benzyloxycarbonyl or t-butoxycarbonyl) and arylalkyl (e.g. benzyl), which may be removed by hydrolysis or hydrogenolysis as appropriate. Other suitable amine protecting groups include trifluoroacetyl (—COCF₃) which may be removed by base catalysed hydrolysis, or a solid phase resin bound benzyl group, such as a Merrifield resin bound 2,6-dimethoxybenzyl group (Ellman linker) or a 2,6-dimethoxy4-[2-(polystyrylmethoxy)ethoxy]benzyl, which may be removed by acid catalysed hydrolysis, for example with trifluoroacetic acid.

Process (d) may be performed using conventional interconversion procedures such as epimerisation, oxidation, reduction, alkylation, nucleophilic aromatic substitution, ester hydrolysis or amide bond formation. Alternative conditions for process (d) include t-butoxycarbonyl group addition or removal and sulphonylation.

Process (e) may be performed using a suitable base, eg. potassium tert-butoxide and a suitable solvent, eg. N,N-dimethylformamide, at a suitable temperature, eg. 60° C.

Process (f) may be performed in the presence of a suitable acid eg. acetic acid and a suitable reducing agent, eg. sodium triacetoxyborohydride in a suitable solvent, eg. dichloromethane at a suitable temperature, eg. room temperature.

Process (g) may be performed in the presence of suitable reagents, eg. 1,-(3-dimethylaminopropyl)-3-ethyl-carbodiimide hydrochloride and 1-hydroxybenzotriazole in the presence of a suitable base, eg. N,N-diisopropylethylamine and a suitable solvent eg. N,N-dimethylformamide at a suitable temperature, eg. room temperature.

Compounds of formula (II) may be prepared according to the following process:

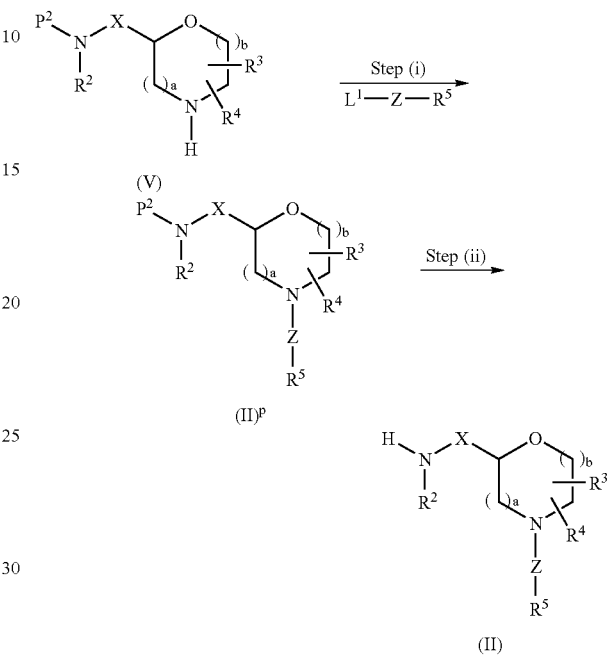

wherein $R^2$, $R^3$, $R^4$, $R^5$, X, a, b and Z are as defined above and $L^1$ represents a suitable leaving group eg. chlorine and $P^2$ represents a suitable protecting group eg. one mentioned above, such as —COCF₃. Step (i) comprises the use of a suitable solvent eg. N,N-dimethylformamide in the presence of suitable reagents eg. sodium iodide and potassium carbonate at a suitable temperature eg. room temperature. Alternatively step (i) may comprise the use of a suitable solvent eg. N,N-dimethylformamide, in the presence of a suitable base such as N,N-diisopropylethylamine at a suitable temperature eg. room temperature. Step (ii) comprises deprotection under conventional conditions appropriate for the protecting groups. When $P^2$ represents —COCF₃, deprotection may be achieved by the use of water and methanol in the presence of potassium carbonate at room temperature.

Compounds of formula (II)$^P$ may also be prepared by reductive amination of compounds of formula (V) in an analogous manner to that described in process (f) above.

Compounds of formula (II) wherein $R^2$ represents hydrogen, X represents methylene, a and b represent 1 and $R^3$ and $R^4$ are both attached to the morpholine ring at the 5-position may be prepared according to the following process:

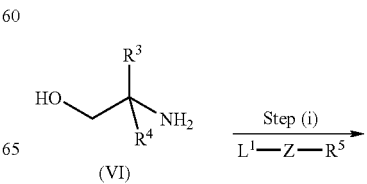

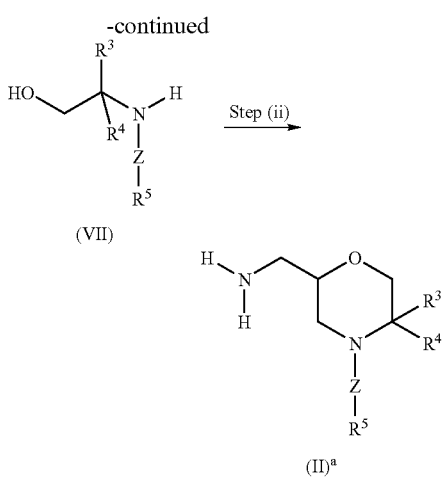

wherein $R^3$, $R^4$ and $R^5$ and Z are as defined above and $L^1$ represents a suitable leaving group eg. chlorine. Step (i) comprises heating in the absence of solvent at between 50 and 60° C. Step (ii) comprises heating with 2-(oxiran-2-ylmethyl)-1H-isoindole-1,3(2H)-dione at 80° C. under nitrogen, followed by stirring with concentrated sulphuric acid at 150° C.

Compounds of formula (II) wherein $R^2$ represents H may be prepared according to the following process:

wherein $R^3$, $R^4$, $R^5$, X, a, b and Z are as defined above and $L^1$ represents a suitable leaving group eg. chlorine. Step (i) comprises heating a compound of formula (VIII; Merrifield Resin) with sodium carbonate in a suitable solvent eg. dimethylsulphoxide at a suitable temperature eg. 150° C. Step (ii) comprises reacting a compound of formula (IX) with a compound of formula (X) in the presence of a suitable solvent eg. tetrahydrofuran at a suitable temperature eg. room temperature. Step (iii) comprises the use of suitable solvent eg. N,N-dimethylformamide and a suitable base eg. N,N-diisopropylethylamine at a suitable temperature eg. 70° C., followed by deprotection under conventional conditions appropriate for the Merrifield resin protecting group eg. acid catalysed hydrolysis.

Compounds of formula $R^1$COOH used in process (a) above (and activated derivatives thereof) are either known compounds or may be synthesised by known methods.

For example, compounds of formula $R^1$COOH wherein $R^1$ represents heteroaryl-$Y^1$, aryl-(O)$_t$-heteroaryl-$Y^1$— or heteroaryl-(O)$_t$-heteroaryl-$Y^1$— (wherein the heteroaryl moiety linked to $Y^1$ represents 1,3-oxazol-4-yl and t represents 0) may be prepared according to the following process:

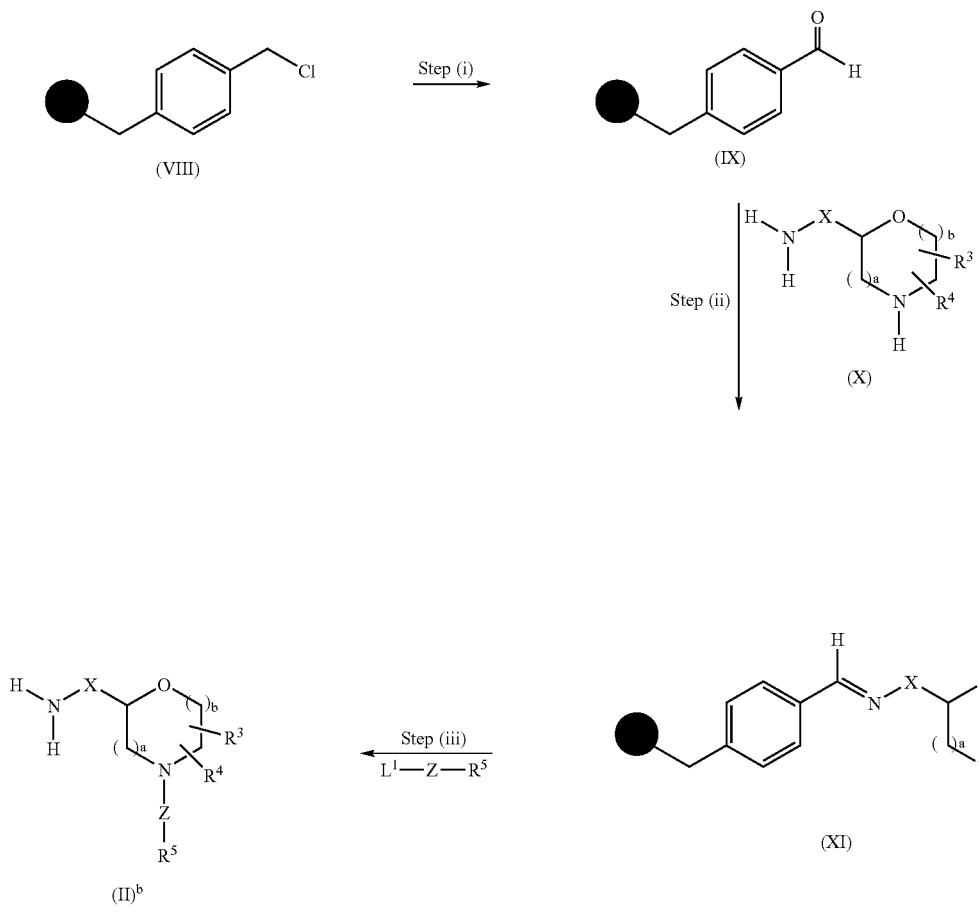

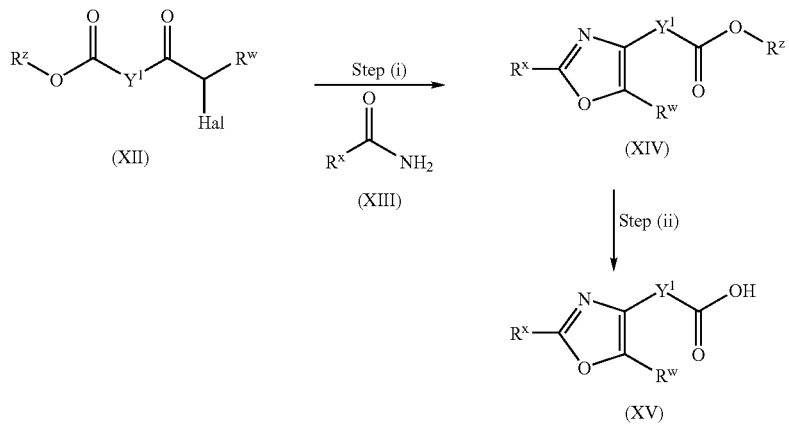

wherein $R^w$ represents a suitable substituent described above for a heteroaryl group, especially $C_{1-6}$ alkyl, $R^x$ represents $C_{1-6}$ alkyl, aryl or heteroaryl, $R^z$ represents $C_{1-6}$ alkyl, especially ethyl, Hal represents a halogen atom, especially bromine and $Y^1$ is as defined above.

Compounds of formula (XII) may be prepared by following the procedure described in Svendsen and Boll (1973) Tetrahedron 29, 4251-4258.

Step (i) may typically be performed in the presence of a suitable solvent, eg. toluene at a suitable temperature eg. at 140° C. and using suitable conditions, eg. Dean-Stark conditions.

Step (ii) may typically be performed in the presence of a suitable alkali, eg. sodium hydroxide and suitable solvents, eg. water and ethanol at a suitable temperature, eg. 70° C.

Compounds of formula $R^1COOH$ wherein $R^1$ represents heteroaryl-$Y^1$, aryl-$(O)_t$-heteroaryl-$Y^1$— or heteroaryl-$(O)_t$-heteroaryl-$Y^1$— (wherein the heteroaryl moiety linked to $Y^1$ represents 1,3-oxazol-4-yl and t represents 0) may also be prepared according to the following process:

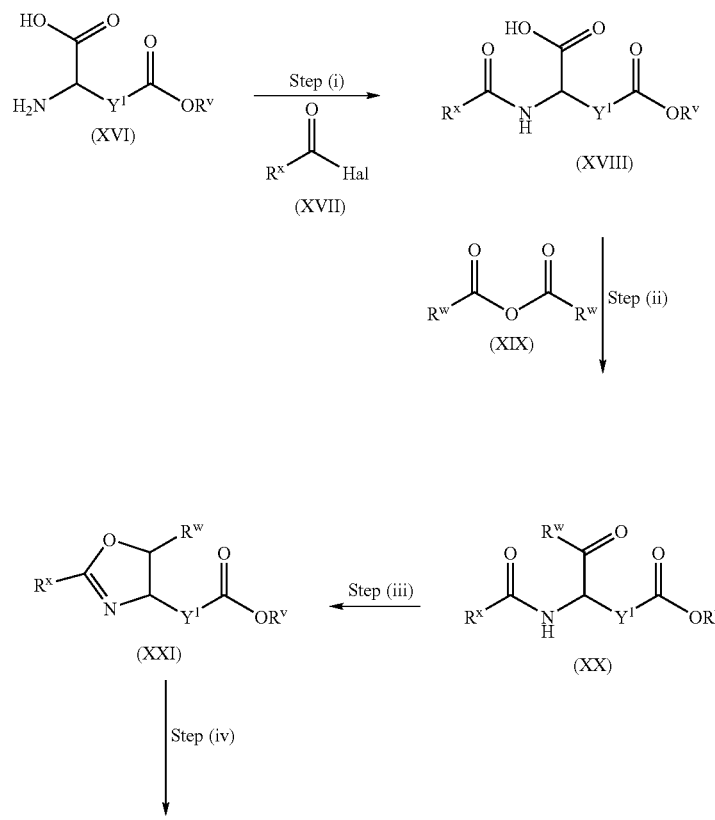

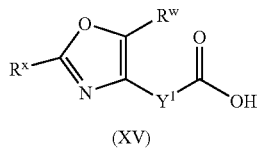

(XV)

wherein $R^v$ represents $C_{1-6}$ alkyl, especially methyl, $R^w$ represents a suitable substituent described above for a heteroaryl group, especially $C_{1-6}$ alkyl, $R^x$ represents $C_{1-6}$ alkyl, aryl or heteroaryl, Hal represents a halogen atom, especially chlorine and $Y^1$ is as defined above.

Step (i) may typically be performed in the presence of a suitable base, eg. pyridine, at a suitable temperature, eg. from 0° C. to room temperature.

Step (ii) may typically be performed in the presence of a suitable base, eg. pyridine at a suitable temperature, eg. 90° C., followed by the addition of water at a suitable temperature, eg. 90° C.

Step (iii) may typically be performed in the presence of a suitable reagent, eg. phosphorus oxychloride and a suitable solvent, eg. toluene, under suitable conditions, eg. 110° C.

Step (iv) may typically be performed in the presence of a suitable alkali eg. 2M aqueous sodium hydroxide, and a suitable solvent, eg. ethanol at a suitable temperature, eg. room temperature.

Compounds of formula (III) as the R-isomer, wherein $R^2$ represents hydrogen, X represents methylene, a and b represent 1 and $R^3$ and $R^4$ both represent hydrogen may be prepared according to the following process:

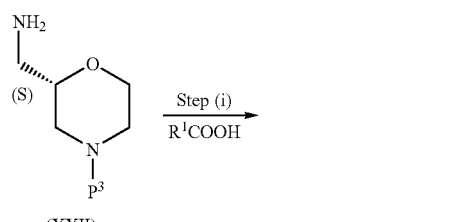

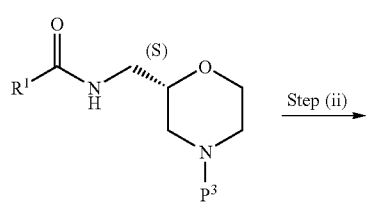

wherein $R^1$ is as defined above and $P^3$ is a suitable protecting group, eg. benzyl.

Compounds of formula (XXII) may be prepared as described in EP0995746.

Step (i) typically comprises the use of 1-hydroxybenzotriazole and 1-(3-dimethylaminopropyl)-3-ethylcarbodiimide hydrochloride in the presence of a suitable base, eg. N,N-diisopropylethylamine and a suitable solvent, eg. N,N-dimethylformamide, at a suitable temperature, eg. room temperature.

Step (ii) typically comprises a simple deprotection reaction, eg. which may comprise the use of 10% palladium on activated carbon in the presence of ammonium formate and a suitable solvent, eg. ethanol.

Compounds of formula (III) as the S-isomer, wherein $R^1$ is as defined above, may be prepared by an analogous process.

Compounds of formula (IV) may be prepared according to the following process:

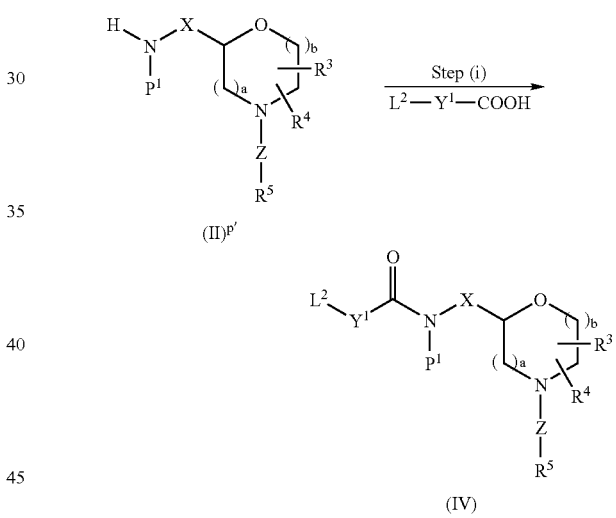

wherein $R^3$, $R^4$, $R^5$, X, $Y^1$, Z, a and b are defined above, $L^2$ represents a suitable leaving group, such as a halogen atom, eg. bromine and $P'$ represents a solid phase resin bound protecting group, such as one described in process (c).

Step (i) typically comprises the use of a suitable reagent, eg. 1,3-diisopropylcarbodiimide in the presence of one or more suitable solvents, eg. dichloromethane and N,N-dimethylformamide.

Compounds of formula (V), (I), (VIII), (X), (XII), (XIII), (XVI), (XVII), (XIX) and (XXII) are either known or may be prepared in accordance with known procedures.

Compounds of formula $L^1$-Z-$R^5$, $R^6CO(CH_2)_nR^5$, $R^5COOH$, $L^2$-$Y^1$—COOH and heterocyclic compounds defined by the $R^1$ groups heteroaryl, aryl-(O)$_t$-heteroaryl or heteroaryl-(O)$_t$-heteroaryl above are also either known or may be prepared in accordance with known procedures.

Compounds of formula (III) may be prepared in accordance with processes analogous to those described above for compounds of formula (I), employing suitable protection for the morpholine (or analogue) NH, e.g. t-butoxycarbonyl protection.

Compounds of formula (II), (III) and (IV) in their protected and deprotected form and salts and solvates thereof are also claimed as an aspect of the invention.

Compounds of the invention may be tested for in vitro and in vivo biological activity in accordance with the following assays.

(a) CCR-3 Binding Assay

A CCR-3 competition binding SPA (scintillation proximity assay) was used to assess the affinity of novel compounds for CCR-3. Membranes prepared from K562 cells stably expressing CCR-3 (2.5 µg/well) were mixed with 0.25 mg/well wheat-germ agglutinin SPA beads (Amersham) and incubated in binding buffer (HEPES 50 mM, $CaCl_2$ 1 mM, $MgCl_2$ 5 mM, 0.5% BSA) at 4° C. for 1.5 hr. Following incubation, 20 pM of [$^{125}$I] eotaxin (Amersham) and increasing concentrations of compound (1 pM to 30 µM) were added and incubated in a 96 well plate for 2 hr at 22° C. then counted on a Microbeta plate counter. The total assay volume was 100 µl. Competition binding data were analysed by fitting the data with a four parameter logistic equation. Data are presented as the mean $pIC_{50}$ values (negative logarithm of the concentration of compound which inhibits [$^{125}$I]eotaxin binding by 50%) from at least two experiments.

(b) Eosinophil Chemotaxis Assay

Compounds were evaluated for their inhibitory effect on eosinophil chemotaxis. Eosinophils were purified from human peripheral blood by standard CD16 cell depletion using a Miltenyi cell separation column and a magnetic Super Macs magnet as previously described (Motegi & Kita, 1998; J. Immunology. 161:4340-6). Cells were re-suspended in RPMI 1640/10% FCS solution and incubated with calcein-AM (Molecular Probes) at 37° C. for 30 mins. Following incubation, the eosinophils were centrifuged at 400 g for 5 min and re-suspended in RPMI/FCS at 2.2 million/ml. Cells were then incubated in the presence of increasing concentration of compounds (1 pM to 30 µM) at 37° C. for 30 mins. For control responses cells were incubated with RPMI/FCS only. The agonist eotaxin (either a concentration response curve or for the functional inhibition curves an $EC_{80}$ concentration) was added to the lower chamber of a 96 well chemotaxis plate (5 µm filter Receptor Technologies). Eosinophils (50 µl of 2 million/ml cells) were added to the top chamber of the filter plate and incubated at 37° C. for 45 mins. Cells remaining on top of the chemotaxis filter were removed and the number of eosinophils which had migrated were quantified by reading the plate on a fluorescent plate reader. Inhibiton curves for the effect of compounds on eosinophil chemotaxis were analysed by fitting the data with a four parameter logistic equation. Functional $pK_i$ values ($fpK_i$) were generated using the equation below (Lazareno & Birdsall, 1995. Br. J. Pharmacol 109: 1110-9).

$$fpKi = \frac{IC_{50}}{1 + \left[\frac{[Agonist]}{EC_{50}}\right]}$$

(c) Guinea-Pig Ovalbumin Model

Inhibition of Eosinophil Infiltration and Hyper-Reactivity in the Guinea Pig

In a method based on that described by Danahay et al., 1997, ovalbumin sensitised guinea pigs were dosed with mepyramine (30 mg $kg^{-1}$ ip) to protect against anaphylactic bronchospasm. Test compounds, dissolved in 10% DMSO and 90% PEG200, were given by the oral route, 30 minutes before ovalbumin challenge (10 minutes breathing of an aerosol generated from a 0.5% solution of ovalbumin). Hyperreactivity of the airways to the thromboxane mimetic U46619, was measured 24 hours after ovalbumin challenge in un-restrained animals using a whole body plethysmograph (Buxco Ltd., USA). The guinea pigs were then sacrificed and the lungs lavaged. Total and differential leukocyte counts were then obtained for the bronchoalveolar lavage fluid and the percentage reduction in eosinophil accumulation determined (Sanjar et al., 1992). Data was presented as the inhibitory effect of the specified dose expressed as a percentage of the vehicle control response.

Examples of disease states in which the compounds of the invention have potentially beneficial anti-inflammatory effects include diseases of the respiratory tract such as bronchitis (including chronic bronchitis), asthma (including allergen-induced asthmatic reactions), chronic obstructive pulmonary disease (COPD) and rhinitis. Another disease of the respiratory tract in which the compounds of the invention have potentially beneficial effects is sinusitis. Other relevant disease states include diseases of the gastrointestinal tract such as intestinal inflammatory diseases including inflammatory bowel disease (e.g. Crohn's disease or ulcerative colitis) and intestinal inflammatory diseases secondary to radiation exposure or allergen exposure. Furthermore, compounds of the invention may be used to treat nephritis, skin diseases such as psoriasis, eczema, allergic dermatitis and hypersensitivity reactions and diseases of the central nervous system which have an inflammatory component eg. Alzheimer's disease, meningitis, multiple sclerosis and AIDS dementia. Compounds of the present invention may also be of use in the treatment of nasal polyposis, conjunctivitis or pruritis. Additionally, the compounds of the present invention may be of use in the treatment of viral diseases such as HIV.

Further examples of disease states in which compounds of the invention have potentially beneficial effects include cardiovascular conditions such as atherosclerosis, peripheral vascular disease and idiopathic hypereosinophilic syndrome. Other diseases for which the compounds of the present invention may be beneficial are other hypereosinophilic diseases such as Churg-strauss syndrome. Additionally, eosinophilia is commonly found in parasitic diseases, especially helminth infections, and thus the compounds of the present invention may be useful in treating inflammation arising from hypereosinophilic states of diseases such as hydatid cyst (*Echinococcus* sp.), tapeworm infections (*Taenia* sp.), blood flukes (schistosomiasis), and nematode (round worms) infections such as:—Hookworm (*Ancylostoma* sp.), *Ascaris, Strongyloides, Trichinella*, and particularly lymphatic filariasis including *Onchocerca, Brugia, Wucheria* (Elephantiasis).

Compounds of the invention may be useful as immunosuppressive agents and so have use in the treatment of autoimmune diseases such as allograft tissue rejection after transplantation, rheumatoid arthritis and diabetes.

Compounds of the invention may also be useful in inhibiting metastasis.

Diseases of principal interest include asthma, COPD and inflammatory diseases of the upper respiratory tract involving seasonal and perennial rhinitis. Preferred diseases of principle interest include asthma and inflammatory diseases of the upper respiratory tract involving seasonal and perennial rhinitis. Further diseases also of principle interest include inflammatory diseases of the gastrointestinal tract such as inflammatory bowel disease.

It will be appreciated by those skilled in the art that reference herein to treatment extends to prophylaxis as well as the treatment of established conditions.

As mentioned above, compounds of formula (I) are useful as pharmaceuticals, in particular as anti-inflammatory agents.

There is thus provided as a further aspect of the invention a compound of formula (I) or a physiologically acceptable salt or solvate thereof for use as pharmaceuticals, particularly in the treatment of patients with inflammatory conditions, eg. asthma or rhinitis.

According to another aspect of the invention, there is provided the use of a compound of formula (I) or a physiologically acceptable salt or solvate thereof for the manufacture of a medicament for the treatment of patients with inflammatory conditions, eg. asthma or rhinitis.

In a further or alternative aspect there is provided a method for the treatment of a human or animal subject with an inflammatory condition eg. asthma or rhinitis, which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in anti-inflammatory therapy, comprising a compound of formula (I) or a physiologically acceptable salt or solvate thereof together, if desirable, with one or more physiologically acceptable diluents or carriers. There is also provided a process for preparing such a pharmaceutical formulation which comprises mixing the ingredients.

The compounds according to the invention may, for example, be formulated for oral, inhaled, intranasal, buccal, parenteral or rectal administration, preferably for oral administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The pharmaceutical compositions according to the invention may also be used in combination with other therapeutic agents, for example anti-inflammatory agents (such as corticosteroids (e.g. fluticasone propionate, beclomethasone dipropionate, mometasone furoate, triamcinolone acetonide or budesonide) or NSAIDs (eg. sodium cromoglycate, nedocromil sodium, PDE-4 inhibitors, leukotriene antagonists, iNOS inhibitors, tryptase and elastase inhibitors, beta-2 integrin antagonists and adenosine 2a agonists)) or beta adrenergic agents (such as salmeterol, salbutamol, formoterol, fenoterol or terbutaline and salts thereof), anti-histamines (eg methapyrilene or loratadine) or antiinfective agents (eg. antibiotics, antivirals).

It will be appreciated that when the compounds of the present invention are administered in combination with other therapeutic agents normally administered by the inhaled or intranasal route, that the resultant pharmaceutical composition may be administered by the inhaled or intranasal route.

Compounds of the invention may conveniently be administered in amounts of, for example, 0.001 to 500 mg/kg body weight, preferably 0.01 to 500 mg/kg body weight, more preferably 0.01 to 100 mg/kg body weight, 1 to 4 times daily. The precise dose will of course depend on the age and condition of the patient and the particular route of administration chosen.

The compounds of the invention have the advantage that they may be more efficacious, show greater selectivity, have fewer side effects, have a longer duration of action, be more bioavailable when administered by the oral route, have more ready and economic synthesis, or have other more desirable properties than similar known compounds.

The invention may be illustrated by reference to the following examples:

EXAMPLES

General Experimental Details

Standard Automated Preparative HPLC Column, Conditions and Eluent

Automated preparative high performance liquid chromatography (autoprep. HPLC) was carried out using a Supelco+5 µm (100 mm×22 mm internal diameter) column eluted with a mixture of solvents consisting of i) 0.1% trifluoroacetic acid in water and ii) 0.1% trifluoroacetic acid in acetonitrile, the eluent being expressed as the percentage of ii) in the solvent mixture, at a flow rate of 4 ml per minute.

Mass Directed Automated Preparative HPLC Column, Conditions and Eluent

Mass directed automated preparative high performance liquid chromatography was carried out using an LCABZ+5

μm (5 cm×10 mm internal diameter) column, employing gradient elution using two solvent systems, (A) 0.1% formic acid in water, and (B) 95% acetonitrile and 0.5% formic acid in water, at a flow rate of 8ml min$^1$. Mass spectrometry was carried out using a VG Plafform Mass Spectrometer, with an HP 1100 Diode Array Detector and Accurate Flow Splitter.

Normal Phase Automated Preparative HPLC Column—Conditions

Normal phase automated preparative high performance liquid chromatography (normal phase autoprep HPLC) was carried out using a Nucleosil silica 5 μm (100 mm×20 mm internal diameter) column eluted with an ethyl acetate:heptane two-step gradient (i) 0% to 25% ethyl acetate over 7min followed by (ii) 25% to 100% ethyl acetate over 5.5min; at a flow rate of 30 ml/min.

LC/MS System

Three alternative Liquid Chromatography Mass Spectroscopy (LC/MS) Systems were used:

System A

This system used a 3 μm ABZ+PLUS (3.3 cm×4.6 mm internal diameter) column, eluting with solvents: A—0.1% v/v formic acid+0.077% w/v ammonium acetate in water; and B—95:5 acetonitrile:water+0.05% v/v formic acid, at a flow rate of 3 ml per minute. The following gradient protocol was used: 100% A for 0.7 mins; A+B mixtures, gradient profile 0-100% B over 3.5 mins; hold at 100% B for 1.1 mins; return to 100% A over 0.2 mins.

System B

This system used a 3 μm ABZ+PLUS (3.3 cm×4.6 mm internal diameter) column, eluting with solvents: A—0.1% v/v formic acid+0.077% w/v ammonium acetate in water; and B—95:5 acetonitrile:water+0.05% v/v formic acid, at a flow rate of 1 ml per minute. The following gradient protocol was used: 100% A for 1.0 min; A+B mixtures, gradient profile 0-100% B over 9.0 mins; hold at 100% B for 3.0 mins; return to 100% A over 2.0 mins.

System C

This system used a 3 μm ABZ+PLUS (3.3 cm×4.6 mm internal diameter) column, eluting with solvents: A—0.1% v/v formic acid+0.077% wlv ammonium acetate in water; and B—95:5 acetonitrile:water+0.05% v/v formic acid, at a flow rate of 1 ml per minute. The following gradient protocol was used: 100% A for 2.0 mins; A+B mixtures, gradient profile 0-100% B over 20 mins; hold at 100% B for 5.0 mins; return to 100% A over 2.0 mins; hold at 100% A for 1.0 mins.

All LC/MS systems (apart from the Mass Directed Automated Preparative HPLC system) used a micromass spectrometer, with electrospray ionisation mode, positive and negative ion switching, mass range 80-1000 a.m.u.

Thermospray Mass Spectra

Thermospray Mass Spectra were determined on a HP 5989A engine mass spectrometer, +ve thermospray, source temperature 250° C., probe temperatures 120° C. (stem), 190° C. (tip), detection mass range 100-850 a.m.u. Compounds were injected in 10 μl of a mixture of solvents comprising 65% methanol and 35% 0.05M aqueous ammonium acetate, at a flow rate of 0.7 ml/min.

Normal Phase Analytical HPLC Method

Normal phase automated analytical high performance liquid chromatography (normal phase analytical HPLC) was carried out using a Nucleosil silica 3 μm (150 mm×4.6 mm internal diameter) column eluted with an ethyl acetate:heptane two-step gradient (i) 0% to 40% ethyl acetate over 7 min followed by (ii) 40% to 100% ethyl acetate over 2.5 min; at a flow rate of 2 ml/min.

Standard Chiral Analytical HPLC System

This system used a 250×4.6 mm Chiralpak AD 10 μm column, eluting with absolute ethanol:heptane mixtures at a flow rate of 1 ml per minute, with UV detection at 215 nm.

Standard Chiral Preparative HPLC System

This system used a Chiralpak AD column (2 cm×25 cm), eluting with absolute ethanol:heptane mixtures (15 ml/min over 25 mins, UV detection at 215 nm).

Solid Phase Extraction (Ion Exchange)

'SCX' refers to Isolute Flash SCX-2 sulphonic acid solid phase extraction cartridges.

Organic/Aqueous Phase Separation with Hydrophobic Frits

'Hydrophobic frit' refers to a Whatman polypropylene filter tube fitted with a PTFE frit, pore size 5.0 μm.

All temperatures are in ° C.

INTERMEDIATES

Intermediate 1

[4-(3,4-Dichlorobenzyl)morpholin-2-yl]methylamine

A mixture of 2-[(3,4-dichlorobenzyl)amino]ethanol (Chem Abs No. 40172-06-3, 0.980 g) and 2-(oxiran-2-ylmethyl)-1H-isoindole-1,3(2H)-dione (1.10 g) was heated at 80° C. under nitrogen for 3 h. The resulting solid mass was treated with concentrated sulphuric acid (1.5 ml) then stirred at 150° C. for 24 h. The mixture was treated with water (100 ml) then washed with ethyl acetate (2×100 ml). The dark aqueous phase was basified to ~pH 12 using 5M aqueous sodium hydroxide, then extracted with ethyl acetate (2×100 ml). The combined organic extracts were washed with water and brine, dried ($Na_2SO_4$) and concentrated under vacuum to give the title compound as a brown oil (1.02 g).

LC-MS (System A): Rt 1.6 min.

Intermediate 1 (Alternative Procedure)

[4-(3,4-Dichlorobenzyl)morpholin-2-yl]methylamine

To a stirred solution of Intermediate 42 (2.97 g) in methanol (15 ml) and water (5 ml) was added potassium carbonate (5.53 g). The mixture was stirred at 22° C. for 18 h before the methanol was removed in vacuo. Water (25 ml) was added and the mixture extracted with ethyl acetate (3×30 ml). The combined organic phases were washed with water (5 ml) and saturated aqueous sodium chloride solution (10 ml) before drying over sodium sulphate, filtering and evaporation of the solvent in vacuo to give a pale yellow oil. The oil was purified by Biotage flash chromatography on a 90 g silica cartridge eluting with 75:8:1 dichloromethane/ethanol/0.880 ammonia solution. The required fractions were combined and the solvent evaporated in vacuo to give the title compound as a colourless oil (1.85 g).

LC/MS (System A) $R_t$ 1.77 min, Mass Spectrum m/z 275 [MH$^+$].

Intermediate 1A

[4-(3,4Dichlorobenzyl)morpholin-2-yl]methylamine salt with para-toluenesulphonic acid 1:1

A solution of 2-[(3,4-dichlorobenzyl)amino]ethanol (2.25 g) and 2-chloroacrylonitrile (1.0 ml) in tetrahydrofuran (3 ml)

was heated at 40° C. for 66 h. The solvent was evaporated in vacuo to leave a gum. The residue was redissolved in tetrahydrofuran (20 ml) and cooled to 0-5° C. Potassium tert-butoxide (1.2 g) was added portionwise to this solution over 10 min and the mixture was stirred at 0-5° C. for a further 45 min. The mixture was diluted with water (20 ml) and ethyl acetate (20 ml), the phases were separated and the organic phase was washed with 20% w/w aqueous sodium chloride solution. The organic phase was dried over sodium sulfate and the solvent was evaporated in vacuo to leave a gum (2.75 g).

A portion of this gum (0.22 g) in tetrahydrofuran (1 ml) was treated dropwise with a 1M solution of borane.tetrahydrofuran complex in tetrahydrofuran (2.44 ml) at 15-25° C. The mixture was stirred at 15-25° C. for 16 h, and methanol (3 ml) was added dropwise. The mixture was stirred for a further 5 h and the solvent was evaporated in vacuo. The residue was redissolved in ethyl acetate (4 ml) and p-toluenesulfonic acid monohydrate (0.123 g) was added. The mixture was heated at 50° C. for 20 min, and the suspension was cooled to 15-25° C. and stirred for 15 min. The mixture was filtered, washed with ethyl acetate and dried to give the title compound (0.123 g) as a white solid.

LC/MS (System A) $R_t$ 1.75 min. Mass spectrum m/z 275/277 [MH+]

Intermediate 2

2-[(3,4-Dichlorobenzyl)amino]-2-methylpropan-1-ol 3,4-Dichlorobenzyl chloride (3.95 g) was added to 2-amino-2-methylpropan-1-ol (17.8 g) and the mixture was stirred at 60° C. under nitrogen for 2 h. Excess amine was removed by distillation under vacuum and the residue was partitioned between saturated aqueous sodium bicarbonate (100 ml) and ethyl acetate (100 ml). The phases were separated, the organic layer was washed with water (4×100 ml) and brine (100 ml), dried ($Na_2SO_4$) and concentrated under vacuum to give the title compound as a white solid (4.7 g).

LC-MS (System A): Rt 2.07 min.

Intermediate 3

1-[4-(3,4-Dichlorobenzyl)-5,5-dimethylmorpholin-2-yl]methanamine

A mixture of Intermediate 2 (0.260 g) and 2-(oxiran-2-ylmethyl)-1H-isoindole-1,3(2H)-dione (0.205 g) was heated at 80° C. under nitrogen for 3 h. The mixture was treated with concentrated sulphuric acid (0.3 ml) then stirred at 150° C. for 18 h. The mixture was treated with water (25 ml) then washed with ethyl acetate (2×25 ml). The dark aqueous phase was basified to ~pH 11 using 5M aqueous sodium hydroxide then extracted with ethyl acetate (2×25 ml). The combined organic extracts were washed with water and brine, dried ($Na_2SO_4$) and concentrated under vacuum to give the title compound as a brown oil (0.225 g).

LC-MS (System A): Rt 1.92 min.

Intermediate 4

2-[(3,4-Dichlorobenzyl)amino]propan-1-ol 3,4-Dichlorobenzyl chloride (0.988 g) was added to 2-amino-1-propanol (4.10 g) and the mixture was stirred at 50° C. under nitrogen for 2 h. The mixture was partitioned between saturated aqueous sodium bicarbonate (100 ml) and ethyl acetate (100 ml) and the phases were separated. The organic layer was washed with water (4×100 ml) and brine, dried ($Na_2SO_4$) then concentrated under vacuum to give the title compound as a white solid (0.935 g).

LC-MS (System A): Rt 2.13 min.

Intermediate 5

1-[(cis)-4-(3,4-Dichlorobenzyl)-5-methylmorpholin-2-yl]methanamine (2:1 Mixture with Trans Isomer)

A mixture of Intermediate 4 (0.470 g) and 2-(oxiran-2-ylmethyl)-1H-isoindole-1,3(2H)-dione (0.410 g) was heated at 80° C. under nitrogen for 5 h. The mixture was treated with concentrated sulphuric acid (0.6 ml) then stirred at 150° C. for 42 h. The mixture was treated with water (50 ml) then washed with ethyl acetate (2×50 ml). The dark aqueous phase was basified to ~pH 11 using 5M aqueous sodium hydroxide then extracted with ethyl acetate (2×50 ml). The combined organic extracts were washed with water and brine, dried ($Na_2SO_4$) and concentrated under vacuum to give the title compound as a brown oil (0.42 g).

LC-MS (System A): Rt 1.74 min.

Intermediate 6

2-{[3-(3,4-Dichlorophenyl)propyl]amino}ethanol 4-(3-Bromopropyl)-1,2-dichlorobenzene (Chem Abs No. 29648-26-8, 1.30 g) was added to ethanolamine (2.8 ml) and the mixture stirred at 60° C. under nitrogen for 2 h. The mixture was concentrated under vacuum at 80° C. and the residue was partitioned between saturated aqueous sodium bicarbonate (100 ml) and ethyl acetate (100 ml). The phases were separated, the aqueous layer was re-extracted with ethyl acetate (100 ml) and the combined organic extracts were washed with water (2×100 ml) and brine then dried ($Na_2SO_4$). The solution was concentrated under vacuum to give the title compound as a pale yellow liquid (1.10 g).

LC-MS (System A): Rt 2.40 min.

Intermediate 7

1-{4-[3-(3,4-Dichlorophenyl)propyl]morpholin-2-yl}methanamine

A mixture of Intermediate 6 (1.05 g) and 2-(oxiran-2-ylmethyl)-1H-isoindole-1,3(2H)-dione (1.10 g) were heated at 80° C. under nitrogen for 2 h. The mixture was treated with concentrated sulphuric acid (1.5 ml) then stirred at 150° C. for 18 h. The mixture was treated with water (100 ml) then washed with ethyl acetate (2×10 ml). The dark aqueous phase was basified to ~pH 11 using 5M aqueous sodium hydroxide then extracted with ethyl acetate (2×100 ml). The combined organic extracts were washed with water and brine, dried ($Na_2SO_4$) and concentrated under vacuum to give the title compound as a brown oil (0.980 g).

LC-MS (System A): Rt 2.05 min.

Intermediate 8

1-[4-(2,3-Dichlorobenzyl)morpholin-2-yl]methanamine hydrochloride

A mixture of chloromethylpolystyrene-divinylbenzene (Merrifield resin, loaded at 4.0 mmol $g^{-1}$) (5.0 g) and sodium hydrogen carbonate (14.5 g) in dimethylsulphoxide (80 ml) was heated at 150° C. for 8 h. The solution was allowed to cool, left to stand for 24 h, then filtered. The solid was washed successively with water (3×100 ml), tetrahydrofuran (3×100 ml) and diethyl ether (3×100 ml), then dried in vacuo to give the formylpolystyrene as a yellow solid which was not characterised. A portion of this solid (1.0 g) was washed with tetrahydrofuran (5×10 ml) and transferred to a round bottomed flask. 1-Morpholin-2-ylmethanamine dihydrochloride (0.435 g) was dissolved in methanol (10 ml) and loaded equally onto two solid phase extraction columns (Isolute SCX sulphonic acid, 10 g each) which had been prepared by application of methanol. Elution with methanol, then 0.880 ammonia:methanol 10:90 gave a clear colourless oil (0.280 g). This was added in tetrahydrofuran (2.3 ml) to the round bottomed flask containing formylpolystyrene and the mixture stirred for 24 h at 20° C. The mixture was then filtered, and the solid washed with tetrahydrofuran:methanol 1:1 to leave N-{[4-(polystyrene resin)phenyl]methylidene}-1-morpholin-2-ylmethanamine as a yellow solid which was not characterised. Two portions of this solid (2×50 mg) in two thick walled glass vials (Reactivials) were each treated with N,N-dimethylformamide (1.25 ml), N,N-diisopropylethylamine (0.097 ml) and 1,2-dichloro-3-(chloromethyl)benzene (0.076 ml), and the mixture was stirred at 70° C. for 20 h, then allowed to cool. The mixtures were combined, filtered and washed sequentially with N,N-dimethylformamide (10×10 ml) and tetrahydrofuran (5×10 ml), then treated with tetrahydrofuran: 2M aqueous hydrochloric acid solution 3:1 (3 ml). After 2 h shaking at 20° C., the mixture was filtered, washed with tetrahydrofuran (4×5 ml) and the filtrate and washings concentrated in vacuo to give the title compound as white crystals (0.060 g).

1HNMR (MeOD) 7.85 (1H, dd, aromatic CH), 7.78 (1H, dd, aromatic CH), 7.53 (1H, t, aromatic CH), 4.72 (2H, AB, CH$_2$), 4.30-4.23 (2H, m, 2×CH), 4.05 (1H, br.t, CH), 3.65 (1H, br.d, CH), 3.58 (1H, br.d, CH), 3.47 (1H, dd, CH), 3.30-3.22 (1H, m, 2×CH), 3.08 (1H, br.m, CH).

Intermediate 9

1-[(2S)-4-(3,4-Dichlorobenzyl)morpholin-2-yl]methanamine

Intermediate 1 (racemic mixture, 8 g) was separated into its single enantiomers by preparative chiral-HPLC. The separation was carried out using a 2"×22 cm Chiralpak AD 20 μm column, Merck self pack DAC system, eluting with 95:5:0.1 (v/v) heptane:absolute ethanol:diethylamine (flow rate: 55 ml/min over 40 min, UV detection 225 nm); sample load preparation: 400 mg sample in 20 ml 3:2 (v/v) absolute ethanol: system eluent.

The title compound (2.49 g) was obtained with preparative HPLC retention time 23.0 min.

Intermediate 9A

1-[(2S)-4-(3,4Dichlorobenzyl)morpholin-2-yl]methanamine salt with D-tartaric acid 1:1

35% Hydrazine in water (1.8 ml) was added to a slurry of Intermediate 41 (5 g) in industrial methylated spirits (75 ml), and the mixture was heated to reflux. Chloroform (75 ml) was added and the mixture was heated under reflux for 65 h. The reaction mixture was cooled to 0-4° C. and allowed to stand for 15 min. The by-product phthalhydrazide was removed by vacuum filtration and washed with chloroform (50 ml). The filtrate was washed with water (50 ml, 25 ml), dried (MgSO$_4$), and the solvent evaporated in vacuo to give an oil. This was dissolved in methanol (20 ml), which was evaporated in vacuo to give an oil. The oil was dissolved in methanol (100 ml) and D-tartaric acid (1.05 g) was added. The mixture was heated to and maintained at reflux for 30 min. The solution was cooled to 45-50° C., then seeded. The slurry was held at this temperature for 30 min, then cooled to 0-4° C. and allowed to stand for 30 min. The product was isolated by filtration to give the title compound as a white solid (2.59 g).

A sample of the crude D-tartrate salt (500 mg) was dissolved in water (1.4 ml). Methanol (23 ml) was added to give a slurry which was heated to reflux to give a solution. The mixture was stirred at reflux for 30 min, then cooled slowly, seeding at 55° C. The resultant slurry was cooled to 0-4° C. and allowed to stand 30 min. The product was isolated by filtration to give the title compound as a white solid (0.355 g).

ee: 91.6% ee

LC/MS (System A) R$_t$ 1.75 min. Mass spectrum m/z 275/277 [MH$^+$]

Chiral analytical HPLC (Chiralpak AD column, 4.6×250 mm, eluent 50:50:0.1 MeOH:EtOH: Butylamine, flow rate 0.5 ml/min, UV detection at 220 nm), Rt 8.9 min.

Intermediate 9A (Alternative Procedure)

1-[(2S)-4-(3,4-Dichlorobenzyl)morpholin-2-yl]methanamine salt with D-tartaric acid 1:1

Intermediate 1 (0.613 g) was dissolved in methanol (12.3 ml). D-Tartaric acid (0.335 g) was added and the slurry was heated to reflux for 50 min. The mixture was allowed to cool to 0-5° C. and the precipitate isolated by filtration to give the title compound as a white solid (0.4 g).

ee: 76% ee

Chiral analytical HPLC (Chiralpak AD column, 4.6×250 mm, eluent 50:50:0.1 MeOH: EtOH: Butylamine, flow rate 0.5 ml/min, UV detection at 220 nm), Rt 8.9 min.

Intermediate 10

1-[(2R)-4-(3,4Dichlorobenzyl)morpholin-2-yl]methanamine

Intermediate 10 was prepared in an analogous manner to Intermediate 9 yielding the title compound (2.24 g) with preparative HPLC retention time 27.8 min.

Intermediate 10A

1-[(2R)-4-(3,4Dichlorobenzyl)morpholin-2-yl]methanamine salt with L-tartaric acid 1:1

[4-(3,4-Dichlorobenzyl)morpholin-2-yl]methylamine (Intermediate 1) (0.500 g) was dissolved in methanol (5 ml). L-Tartaric acid (0.273 g) was added and the mixture was heated to ~65° C. to give a milky slurry, and maintained at this temperature for 1 h. Further methanol (5 ml) was added and the mixture left to cool slowly to 15-25° C., then cooled further to 0-4° C. The mixture was stirred for 30min at this temperature and the product isolated by filtration to give the title compound as a white solid (0.38 g).

ee: 78%

LC/MS (System A) Rt 1.75 min. Mass spectrum m/z 275/277 [MH$^+$]

Chiral analytical HPLC (Chiralpak AD column, 4.6×250 mm, eluent 50:50:0.1 MeOH:EtOH: Butylamine, flow rate 0.5 ml/min, UV detection at 220 nm), Rt 10.5 min.

Intermediate 11

Ethyl[2-(4-fluorophenyl)-5-methyl-1,3-oxazol-4-yl]acetate

A suspension of 4fluorobenzamide (12.9 g) and ethyl 4bromo-3-oxopentanoate (Chem Abs No. 3618769-6; 5.24 g) in anhydrous toluene (120 ml) was heated at 140° C. for 19 h, using a Dean-Stark trap. The solution was allowed to cool, filtered, and the residual solid washed with toluene (30 ml). The combined filtrate and washings were concentrated in vacuo to give a brown oil, which was purified by Biotage flash chromatography on silica gel (90 g column), eluting with ethyl acetate:cyclohexane (5:95, 7.5:92.5, 10:90), to give the title compound as a yellow solid (2.98 g).

LC/MS (System A) Rt 3.26 min. Mass spectrum m/z 264 [MH$^+$].

Intermediate 12

[2-(4-Fluorophenyl)-5-methyl-1,3-oxazol-4-yl]acetic acid

Intermediate 11 (2.98 g) in ethanol (25 ml) was treated with aqueous sodium hydroxide (2.5M, 18 ml) and the solution stirred at 70° C. for 3.5 h then allowed to cool. The material was concentrated in vacuo to remove the ethanol, then the aqueous phase was washed with ethyl acetate (30 ml). The aqueous phase was adjusted to pH 1 by addition of aqueous hydrochloric acid (5M) and the desired acid was extracted into ethyl acetate (1×100ml, 1×50 ml). The combined organic phases were washed with dilute aqueous sodium chloride, dried (Na$_2$SO$_4$), filtered and the solution concentrated in vacuo to give the title compound as a cream solid (2.549).

LC/MS (System A) Rt 2.85 min. Mass Spectrum m/z 236 [MH$^+$].

Intermediate 13

1{4-[(5-Chlorothien-2-yl)methyl]morpholin-2-yl}methanamine

Intermediate 13 was prepared in an analogous manner to Intermediate 1 (Alternative procedure) from Intermediate 19 and 2-chloro-5-(chloromethyl)thiophene, followed by a deprotection reaction yielding the title compound.

Intermediate 14

1-{(2S)-4-[(5-Chlorothien-2-yl)methyl]morpholin-2-yl}methanamine

Intermediate 13 was separated into its single enantiomers by chiral preparative HPLC to give the title compound in an analogous manner to the separation of Intermediate 1 to yield Intermediate 9.

LCMS (system A) R$_t$ 25.2 min.

Chiral Preparative HPLC retention time 25.2min

Intermediate 14A

1-{(2R)-4-[(5-Chlorothien-2-yl)methyl]morpholin-2-yl}methanamine

Intermediate 14A was prepared in an analogous manner to Intermediate 14 yielding the title compound.

LCMS (system A) R$_t$ 34 min.

Chiral Preparative HPLC retention time 34 min.

Intermediate 15

N-{[(2S)-4-Benzylmorpholin-2-yl]methyl}-2-(5-methyl-2-phenyl-1,3-oxazol-4-yl)acetamide A mixture of (5-methyl-2-phenyl-oxazol-4-yl)-acetic acid (0.263 g), 1-hydroxylbenzotriazole (0.163 g), and N,N-diisopropylethylamine (0.211 ml) in N,N-dimethylformamide (3 ml) was treated with 1-(3-dimethylaminopropyl)-3-ethylcarbodiimide hydrochloride (0.232 g). The mixture was stirred for 5 min, treated with 1-[(2S)-4-benzylmorpholin-2-yl]methanamine (prepared in accordance with EP 0 995 746 A1; 0.192 g), and the solution was stirred at 22° C. for 18 h. The mixture was partitioned between dichloromethane (20 ml) and saturated aqueous sodium hydrogen carbonate (10 ml). The phases were separated in a hydrophobic frit; the organic phase was loaded onto a solid phase extraction cartridge (10 g SCX) and eluted with methanol, followed by 0.880 ammonia:methanol 10:90 to give the title compound as a colourless gum (0.394 g).

LC/MS (System A) R$_t$ 2.42 min. Mass spectrum m/z 406 [MH$^+$].

Chiral analytical HPLC, eluent 10% EtOH/n-heptane, R$_t$ 18.55 min.

Intermediate 15A

N-{[(2R)-4-Benzylmorpholin-2-yl]methyl}-2-(5-methyl-2-phenyl-1,3-oxazol-4-yl)acetamide Prepared in an analogous manner to Intermediate 15 from 1-[(2R)-4-benzylmorpholin-2-yl]methanamine (prepared in accordance with EP 0 995 746 A1) to obtain the R isomer.

Chiral analytical HPLC eluent 10% EtOH/n-heptane, R$_t$ 16.296 min.

Intermediate 16

2-(5-Methyl-2-phenyl-1,3-oxazol-4-yl)-N-[(2R)-morpholin-2-ylmethyl]acetamide

A mixture of Intermediate 15 (0.192 g) and ammonium formate (0.4 g) in absolute ethanol (2 ml) was treated with 10% palladium on activated carbon (0.1 g). After 1.5 h the mixture was treated with ammonium formate (0.6 g) and stirred under nitrogen for a further 15.5 h.

The mixture was filtered through celite and the residue washed with absolute ethanol (20 ml). The solvent was removed at reduced pressure to leave a gum. The residue was partitioned between ethyl acetate (20 ml) and 2N sodium hydroxide (20 ml). The phases were separated and the aqueous phase extracted with ethyl acetate (10 ml). The combined organic extracts were filtered through Whatman silicone treated filter paper and the solvent removed at reduced pressure to give the title compound (0.077 g) as a colourless gum.

LC/MS (System A) R$_t$ 2.14 min. Mass spectrum m/z 316 [MH$^+$].

Intermediate 17

2-(5-Methyl-2-phenyl-1,3-oxazol-4-yl)-N-[(2S)-morpholin-2-ylmethyl]acetamide

Intermediate 17 was prepared in an analogous manner to Intermediate 16 from Intermediate 15A yielding the title compound

Intermediate 18

{3-[(Methylsulfonyl)amino]phenyl}acetic acid

Methanesulphonylchloride (1.70 ml) was added to a stirred mixture of 3-aminophenylacetic acid (3.2 g) and sodium carbonate (5.44 g) in water (36 ml), and the mixture was heated at 85° C. with stirring for 4 h, allowed to cool and acidified with conc. hydrochloric acid to pH 2. After leaving to stand at approximately 4° C. for 18 h, a solid was filtered off, and the residue washed with water and ether. The aqueous and ether filtrates were combined and evaporated in vacuo to give a solid, which was dissolved in hot water, the solution was filtered whilst still hot and the filtrate left to cool before standing at 4° C. for 18 h. The precipitated solid was filtered, washed with a small quantity of cold water and dried in vacuo to give the title compound as a pale yellow solid (0.417 g).
$^1$H nmr (400 MHz, $d_6$ DMSO) 12.35 (1H, br, s, COOH), 9.74 (1 H, s, NH), 7.27 (1H, dd, CH), 7.13-7.08 (2H, m, 2×CH), 6.99 (1H, br, d, CH), 3.54 (2H, s, $CH_2$), 2.98 (3H, s $CH_3$)
LCMS (system A) $R_t$ 2.07 min. Mass Spectrum m/z=247 [$MNH_4^+$] m/z=228 [$MH^-$].

Intermediate 19

2,2,2-Trifluoro-N-(morpholin-2-ylmethyl)acetamide

To a stirred solution of morpholin-2-ylmethylamine (3.1 g) in methanol (70 ml) under nitrogen was added an ethereal solution of ethyl-α,α,α-trifluoroacetate (5 ml in 20 ml ether) which had been washed with saturated aqueous sodium bicarbonate, water and brine, and dried. The mixture was stirred for 30 min at 22° C. before removal of all volatiles in vacuo. The residue was dissolved in methanol (10 ml) and the volatiles again removed in vacuo to give the title compound as a white crunchy foam (4.9 g).
Thermospray Mass Spectrum m/z 213 [$MH^+$].

Intermediate 20

1-[4-(3,4-Difluorobenzyl)morpholin-2-yl]methanamine

Intermediate 20 was prepared in an analogous manner to Intermediate 1 (Alternative Procedure) from Intermediate 19 and 3,4-difluorobenzyl bromide, followed by deprotection to yield the title compound.

Intermediate 21

1-[4-(4-Fluorobenzyl)morpholin-2-yl]methanamine

Intermediate 21 was prepared in an analogous manner to Intermediate 1 (Alternative Procedure) from Intermediate 19 and 4-fluorobenzyl chloride, followed by deprotection to yield the title compound.

Intermediate 22

1-[(2S)-4-(4-Fluorobenzyl)morpholin-2-yl]methanamine

Intermediate 21 was separated into its single enantiomers by chiral preparative HPLC to give the title compound in an analogous manner to the separation of Intermediate 1 to yield Intermediate 9.
LCMS (system A) $R_t$ 18.43 min.
Chiral Preparative HPLC Retention time 18.43 min.

Intermediate 23

1-[(2R)-4-(4-Fluorobenzyl)morpholin-2-yl]methanamine

Intermediate 23 was prepared in an analogous manner to Intermediate 22 yielding the title compound.
LCMS (system A) $R_t$ 26.56 min.
Chiral Preparative HPLC Retention time 26.56 min.

Intermediate 24

[(2S)-4-(3-chlorobenzyl)morpholin-2-yl]methylamine

Intermediate 24 was prepared in an analogous manner to Intermediate 9
Preparative chiral HPLC retention time 26.1 min

Intermediate 25

[(2S)-4-(2,3-dichlorobenzyl)morpholin-2-yl]methylamine

Intermediate 25 was prepared in an analogous manner to Intermediate 9.
Preparative chiral HPLC retention time 25.3min

Intermediate 26

[(2S)-4-(3,4-difluorobenzyl)morpholin-2-yl]methylamine

Intermediate 26 was prepared in an analogous manner to Intermediate 9.
Preparative chiral HPLC retention time 28.3

Intermediate 27

1-[(cis)-4-(2,5-dichlorobenzyl)-5-methylmorpholin-2-yl]methanamine (2:1 Mixture with Trans Isomer)

Intermediate 27 was made in an analogous manner to Intermediate 5.
LC-MS (System A): Rt 1.88 mins Mass Spectrum m/z 289 [$MH^+$]

Intermediate 28

2-[2-(4-fluorophenyl)-5-methyl-1,3-oxazol-4-yl]-N-[(2R)-morpholin-2-ylmethyl]acetamide Intermediate 28 was prepared in an analogous manner to Intermediate 16.
LC-MS (System A): Rt 2.21 mins Mass Spectrum m/z 334 [$MH^+$]

Intermediate 29

[4-(3-Fluorobenzyl)morpholin-2-yl]methylamine

A mixture of Intermediate 19 (0.300 g) and N,N-diisopropylethylamine (0.372 ml) in N,N-dimethylformamide (5 ml) was treated with 3-fluorobenzyl bromide (0.295 g). The solution was stirred at 20° C. under nitrogen for 24 h. The mixture was partitioned between dichloromethane (10 ml) and saturated aqueous potassium carbonate (10 ml). The phases were separated and the organic phase applied to an ion exchange cartridge (10 g Isolute SCX, prewashed with methanol). The SCX cartridge was eluted with methanol (40 ml) followed by 10% 0.880 ammonia in methanol (40 ml) and the appropriate fractions were concentrated in vacuo. The residue was dissolved in methanol (2 ml) and treated with aqueous 2N sodium hydroxide (2 ml). The solution was stirred at 20° C. for 24 h. The mixture was partitioned between dichloromethane (15 ml) and water (20 ml). The aqueous extract was washed with dichloromethane (15 ml) and the combined organic extracts concentrated to give the title compound as a colourless gum (0.150 g).

Thermospray Mass spectrum m/z 225 [MH$^+$].

Intermediate 30 tert-Butyl[(2S)-4-(3,4-dichlorobenzoyl)morpholin-2-yl]methylcarbamate

A mixture of 3,4-dichlorobenzoic acid (0.5 g), 1-hydroxybenzotriazole (0.376 g), 1-(3-dimethylaminopropyl)-3-ethylcarbodiimide hydrochloride (0.432 g), and N,N-diisopropylethylamine (0.485 ml) in N,N-dimethylformamide (10 ml) was stirred at 20° C. for 10 min. The mixture was treated with tert-butyl(2R)-morpholin-2-ylmethylcarbamate (0.500 g, known compound WO 9639407A1) and stirred at 20° C. for 24 h. The mixture was partitioned between ethyl acetate (75 ml) and 2N aqueous hydrochloric acid (50 ml). The phases were separated and the organic extract washed with 2N aqueous hydrochloric acid (50 ml), saturated aqueous sodium hydrogen carbonate (2×50 ml), dried (MgSO$_4$) and filtered. The solvent was removed in vacuo to give the title compound as a yellow oil, (0.774 g).

LCMS (system A) R$_t$ 3.24min Mass Spectrum m/z 389 [MH$^+$].

Intermediate 31

1-[(2S)-4-(3,4-dichlorobenzoyl)morpholin-2-yl]methanamine hydrochloride

Intermediate 30 (0.770 g) was treated with 4.0M hydrogen chloride in dioxane (8 ml). The mixture was stirred at 20° C. for 30 min. The solvent was removed in vacuo to give the title compound as a white solid (0.592 g).

LCMS (system A) R$_t$ 2.04min Mass Spectrum m/z 289 [MH$^+$]

Intermediate 32

Methyl 4-oxo-3-[(pyridin-3-ylcarbonyl)amino]pentanoate

Nicotinyl chloride hydrochloride (178 mg) was added to a stirred suspension of aspartic acid β-methyl ester hydrochloride (183 mg) in pyridine at 0° C. with stirring under nitrogen, and the mixture was stirred at 0° C. for 1.5 h and at room temperature for 0.5 h. Acetic anhydride (0.37 ml) was added, and the mixture was heated at 90° C. for 2 h. Water (0.6 ml) was added and heating continued for 15 min before the mixture was partitioned between saturated aqueous sodium bicarbonate and dichloromethane. The organic layer was evaporated in vacuo to give a yellow oil (110 mg).

LC-MS (System A) Rt 1.86 min. Mass Spectrum m/z 251 [MH$^+$].

Intermediate 33

Methyl(5-methyl-2-pyridin-3-yl-1,3-oxazol-4-yl)acetate

Intermediate 32 (110 mg) was treated with phosphorous oxychloride (0.51 ml) in toluene (2 ml) and the mixture heated under reflux for 3.5 h. The mixture was poured into ice cold saturated aqueous sodium bicarbonate (30 ml) and extracted with dichloromethane (20 ml). The organic layer was evaporated in vacuo to give a yellow gum (111 mg).

LC-MS (System A) Rt 2.30 min. Mass Spectrum m/z 233 [MH$^+$].

Intermediate 34

(5-Methyl-2-pyridin-3-yl-1,3-oxazol-4-yl)acetic acid

Intermediate 33 (111 mg) was dissolved in tetrahydrofuran (2 ml) and water (0.2 ml) and lithium hydroxide (12 mg) added. The mixture was stirred at 22° C. for 17 h and heated at 60° C. for 2 h. Ethanol (3 ml) and 2N aqueous sodium hydroxide (1 ml) were added, and stirring was continued at 22° C. for 2 h. The mixture was applied to a sulphonic acid ion exchange cartridge (10 g Isolute SCX) and eluted with methanol followed by 10% triethylamine in methanol. Evaporation of the triethylamine containing fraction gave the title compound as a gum (46 mg).

LC-MS (System A) Rt 2.12 min. Mass Spectrum m/z 219 [MH$^+$].

Intermediate 35

Ethyl 4-(methylthio)butanoate

A solution of ethyl 4-bromobutyrate (0.269) in N,N-dimethylformamide (3 ml) was treated with sodium thiomethoxide (0.103 g), and the mixture stirred at room temperature overnight. The mixture was partitioned between water (10ml) and dichloromethane (10 ml), and the organic layer was washed with 1:1 saturated aqueous sodium chloride and water (10 ml). The organic layers were evaporated in vacuo to give the title compound as a clear oil (0.135 g).

NMR (CDCl$_3$) 4.06δ(2H, q, CH$_2$), 2.46δ(2H, t, CH$_2$), 2.35δ(2H, t, CH$_2$), 2.03δ(3H, s, CH$_3$), 1.85δ(2H, m, CH$_2$), 1.18δ(3H, t, CH$_3$).

Intermediate 36

Ethyl 4-(methylsulfonyl)butanoate

A solution of Intermediate 35 (0.126 g) in dry dichloromethane (5 ml) was treated with m-chloroperoxybenzoic acid (0.27 g) portion-wise over ~5 min. The mixture was stirred at room temperature overnight, treated with saturated aqueous sodium carbonate solution (10 ml) and stirred for ~5 min. The organic layers were separated using a hydrophobic frit and evaporated in vacuo to give the title compound as a pale yellow oil (0.133 g).

NMR (CDCl$_3$) 4.15δ(2H, q, CH$_2$), 3.11δ(2H, t, CH$_2$), 2.93δ(3H, s, CH$_3$), 2.52δ(2H, t, CH$_2$), 2.17δ(2H, m, CH$_2$), 1.28δ(3H, t, CH$_3$).

Intermediate 37

4-(Methylsulfonyl)butanoic acid

To a solution of Intermediate 36 (0.130 g) in ethanol (2 ml), was added 2N aqueous sodium hydroxide (0.75 ml). The mixture was stirred at room temperature under nitrogen overnight. The solution was evaporated in vacuo to remove the ethanol, and applied to a solid phase extraction cartridge (Isolute SCX sulphonic acid column, 2 g). The cartridge was eluted with methanol (15 ml) and the solvent concentrated in vacuo to give the title compound as a clear oil (0.110 g).

NMR (MeOD) 3.09δ(2H, m, CH$_2$), 2.88δ(3H, s, CH$_3$), 2.41δ(2H, t, CH$_2$), 1.98δ(2H, m, CH$_2$).

Intermediate 38

Methyl[5-(4-fluorophenyl)-1,2,4-oxadiazol-3-yl]acetate

A mixture of 4-fluorobenzamidoxime (1.54 g) and dimethyl malonate (5.7 ml) was heated under reflux in para-xylene (20 ml) for 2 h. The mixture was cooled, washed with 1M aqueous hydrochloric acid, the organic phase separated and dried (MgSO$_4$) and the solvent evaporated in vacuo. The colourless oily residue was diluted with toluene and the toluene evaporated three times; the residue was re-dissolved in dichloromethane and the solvent evaporated under a stream of nitrogen to give the title compound as colourless crystals (1.59 g).

Thermospray Mass Spectrum m/z 237 [MH$^+$], 254 [MNH$_4^+$]

Intermediate 39

Methyl[3-(aminosulfonyl)phenyl]acetate 0.880 Ammonia (0.027 ml) was added to a stirred solution of methyl[3-(chlorosulfonyl)phenyl]acetate (0.35 g) in a 1:1 mixture of dichloromethane and acetonitrile (1.75 ml), and the mixture was stirred at 22° C. for 2 h. The mixture was allowed to stand for a further 18 h, and the solvent was evaporated in vacuo. The residue was re-dissolved in dichloromethane and applied to a silica gel cartridge (10 g Varian Bond Elut, pre-conditioned with dichloromethane). The cartridge was eluted with dichloromethane, chloroform, ether, ethyl acetate, acetone, acetonitrile and methanol (1 column volume each), the fractions containing the product evaporated in vacuo, and the residue passed down a 5 g silica gel cartridge which was prepared and eluted in an identical manner. The product containing fractions were evaporated in vacuo to give a residue which was further purified using mass-directed preparative HPLC, to give the title compound as a colourless gum (0.018 g).

LCMS (System A) R$_t$ 2.12min Mass Spectrum m/z 230 [MH$^+$], 247 [MNH$_4^+$]

Intermediate 40

[3-(Aminosulfonyl)phenyl]acetic acid Compound with N,N,N-triethylamine (1:1)

A portion (0.120 ml) of a solution of sodium hydroxide (0.123 g) in water (3.05 ml) was added to a stirred solution of Intermediate 39 (0.018 g) in methanol (2 ml) and water (1 ml), and stirring was continued at 22° C. for 7 h. The pH of the mixture was adjusted to approximately 8, and the mixture was applied to an aminopropyl ion exchange cartridge (2 g Isolute SPE, pre-conditioned with methanol). Elution with methanol (3 column volumes) followed by of 10% triethylamine in methanol (2 column volumes), and evaporation of the basic fractions in vacuo gave the title compound as a colourless gum (0.0229).

LCMS (System A) R$_t$ 1.75min Mass Spectrum m/z 214 [MH$^-$], 233 [MNH$_4^+$]

Intermediate 41

2-{[4-(3,4-dichlorobenzyl)morpholin-2-yl]methyl}-1H-isoindole-1,3(2H)-dione

To a solution of 2-(oxiran-2-ylmethyl)-1H-isoindole-1,3 (2H)-dione (2 g) in tetrahydrofuran (4 ml) was added 2-[(3, 4-dichlorobenzyl)amino]ethanol (2.16 g) with stirring, under a nitrogen atmosphere. The mixture was heated to 66° C. for 22 h, then cooled to 0° C. A further portion of tetrahydrofuran (10 ml) was added, followed by triphenylphosphine (2.88 g). Diisopropyl azodicarboxylate (2.2 g) was then added over 10 min. The mixture was stirred at 0° C. for a further 30 min, and at room temperature for 14 h. To the crude solution was added ethyl acetate (100 ml), then 2M aqueous hydrochloric acid (250 ml). The resulting white precipitate was isolated by filtration, and dried in vacuo to give the title compound as its white crystalline hydrochoride salt (2.01 g). This was partitioned between 8% aqueous sodium bicarbonate (200 ml) and ethyl acetate (50 ml). The organic phase was separated, dried over magnesium sulfate and the solvent evaporated in vacuo to give a solid. Dichloromethane (20 ml) was added to the residue and the solvent again evaporated in vacuo to give the title compound as a white solid (1.1 g).

LC/MS R$_t$ 2.91 min. Mass Spectrum m/z 405 [MH$^+$]

Intermediate 42

N-{[4-(3,4Dichlorobenzyl)morpholin-2-yl]methyl}-2,2,2-trifluoroacetamide

To a stirred solution of Intermediate 19 (3.3 g) in N,N-dimethylformamide (50 ml) under nitrogen was added potassium carbonate (2.46 g) and sodium iodide (2.12 g). A solution of 3,4-dichlorobenzyl chloride (2 ml) in N,N-dimethylformamide (10 ml) was added dropwise to the mixture. The mixture was stirred at 22° C. for 18 h before the volatiles were removed in vacuo. The residue was partitioned between dichloromethane (100 ml) and saturated aqueous sodium carbonate solution (50 ml). The organic phase was subsequently washed with additional saturated aqueous sodium carbonate solution (2×50 ml) and water (50 ml) before drying over magnesium sulphate, filtering and evaporation of the solvent in vacuo to give a pale yellow oil. The oil was purified by Biotage flash chromatography on a 90 g silica cartridge eluting with 25% ethyl acetate in cyclohexane, to give the title compound as a colourless oil (2.97 g).

LC/MS (System A) R$_t$ 2.63 min, Mass Spectrum m/z 371 [MH$^+$].

EXAMPLES

Example 1

N-{[4-(3,4-Dichlorobenzyl)morpholin-2-yl]methyl}-2-phenylacetamide

A mixture of Intermediate 1 (0.028 g) and phenylacetic acid (0.015 g) was treated with 1-methyl-2-pyrrolidinone (0.015 ml) then heated in a 600 W microwave oven, at full power, for 4 min. The crude mixture was purified by chromatography on silica gel (Varian Bond-Elut, 1 g) eluting with cyclohexane/ethyl acetate (4:1 followed by 2:1) to give the title compound as a colourless gum (0.029 g).

LC-MS (System A): Rt 2.63 min, Mass Spectrum m/z 393 [MH$^+$].

Example 2

N-{[4-(3,4-Dichlorobenzyl)morpholin-2-yl]methyl}-2-[4-(methylsulfonyl)phenyl]acetamide salt with formic acid (1:1)

Example 2 was prepared in an analogous manner to Example 1 using a mixture of Intermediate 1 (0.055 g) and [4-(methylsulfonyl)phenyl]acetic acid (0.043 g) to give the title compound (0.03 g).

LC-MS (System A): Rt 2.32 mins, Mass Spectrum m/z 471 [MH$^+$].

Example 3

N-{[4-(3,4-Dichlorobenzyl)morpholin-2-yl]methyl}-2-(3-fluorophenyl)acetamide

Example 3 was prepared in an analogous manner to Example 1 using a mixture of Intermediate 1 (0.055 g) and (3-fluorophenyl)acetic acid (0.031 g) to give the title compound (0.041 g).

LC-MS (System A): Rt 2.65 mins, Mass Spectrum m/z 411 [MH$^+$].

Example 4

N-{[4-(3,4-Dichlorobenzyl)morpholin-2-yl]methyl}-2-(4-fluorophenyl)acetamide

Example 4 was prepared in an analogous manner to Example 1 using a mixture of Intermediate 1 (0.055 g) and (4-fluorophenyl)acetic acid (0.031 g) to give the title compound (0.019 g).

LC-MS (System A): Rt 2.72 mins, Mass Spectrum m/z 411 [MH$^+$].

Example 5

N-{[4-(3,4-Dichlorobenzyl)morpholin-2-yl]methyl}-2-[4-(methylthio)phenyl]acetamide Example 5 was prepared in an analogous manner to Example 1 using a mixture of Intermediate 1 (0.055 g) and 4-(methylthio)phenylacetic acid (0.036 g) to give the title compound (0.028 g).

LC-MS (System A): Rt 2.77 mins, Mass Spectrum m/z 439 [MH$^+$].

Example 6

N-{[4-(3,4-Dichlorobenzyl)morpholin-2-yl]methyl}-2-(3,4-difluorophenyl)acetamide Example 6 was prepared in an analogous manner to Example 1 using a mixture of Intermediate 1 (0.055 g) and (3,4-difluorophenyl)acetic acid (0.034 g) to give the title compound (0.0195 g).

LC-MS (System A): Rt 2.84 mins, Mass Spectrum m/z 429 [MH$^+$].

Example 7

N-{[4-(3,4-Dichlorobenzyl)morpholin-2-yl]methyl}-2-{4-[(dimethylamino)sulfonyl]phenyl}acetamide salt with formic acid (1:1)

Example 7 was prepared in an analogous manner to Example 1 using a mixture of Intermediate 1 (0.055 g) and {4-[(dimethylamino)sulfonyl]phenyl}acetic acid (0.049 g) to give the title compound (0.031 g).

LC-MS (System A): Rt 2.46 mins, Mass Spectrum m/z 500 [MH$^+$].

Example 8

2-(3-Chlorophenyl)-N-{[4-(3,4-dichlorobenzyl)morpholin-2-yl]methyl}acetamide

Example 8 was prepared in an analogous manner to Example 1 using a mixture of Intermediate 1 (0.055 g) and (3-chlorophenyl)acetic acid (0.0349) to give the title compound (0.034 g).

LC-MS (System A): Rt 2.64 mins, Mass Spectrum m/z 427 [MH$^+$].

Example 9

N-{[4-(3,4Dichlorobenzyl)morpholin-2-yl]methyl}-2-4-methylphenyl)acetamide

Example 9 was prepared in an analogous manner to Example 1 using a mixture of Intermediate 1 (0.055 g) and (4-methylphenyl)acetic acid (0.03 g) to give the title compound (0.024 g).

LC-MS (System A): Rt 2.64 mins, Mass Spectrum m/z 407 [MH$^+$].

Example 10

4-[2-({[4-(3,4Dichlorobenzyl)morpholin-2-yl]methyl}amino)-2-oxoethyl]benzamide

Example 10 was prepared in an analogous manner to Example 1 using a mixture of Intermediate 1 (0.055 g) and [4-(aminocarbonyl)phenyl]acetic acid (0.036 g) to give the title compound (0.01 g).

LC-MS (System A): Rt 2.20 mins, Mass Spectrum m/z 436 [MH$^+$].

Example 11

2-(4-Chlorophenyl)-N-{[4-(3,4-dichlorobenzyl)morpholin-2-yl]methyl}acetamide

Example 11 was prepared in an analogous manner to Example 1 using a mixture of Intermediate 1 (0.028 g) and (4-chlorophenyl)acetic acid (0.019 g) to give the title compound (0.033 g).

LC-MS (System A): Rt 2.86 min, Mass Spectrum m/z 427 [MH$^+$].

Example 12

N-{[4-(3,4-Dichlorobenzyl)morpholin-2-yl]methyl}-2-[4-(dimethylamino)phenyl]acetamide salt with formic acid (1:1)

Example 12 was prepared in an analogous manner to Example 1 using a mixture of Intermediate 1 (0.055 g) and [4-(dimethylamino)phenyl]acetic acid (0.036 g) to give the title compound (0.025 g).

LC-MS (System A): Rt 2.27 mins, Mass Spectrum m/z 436 [MH$^+$].

Example 13

N-{[4-(3,4-Dichlorobenzyl)morpholin-2-yl]methyl}-2-(2,5-dichlorophenyl)acetamide Example 13 was prepared in an analogous manner to Example 4 using a mixture of Intermediate 1 (0.055 g) and (2,5-dichlorophenyl)acetic acid (0.041 g) to give the title compound (0.025 g).

LC-MS (System A): Rt 2.89 mins, Mass Spectrum m/z 463 [MH$^+$].

Example 14

N-{[4-(3,4-Dichlorobenzyl)morpholin-2-yl]methyl}-2-[4-(trifluoromethyl)phenyl]acetamide Example 14 was prepared in an analogous manner to Example 1 using a mixture of Intermediate 1 (0.055 g) and [4-(trifluoromethyl)phenyl]acetic acid (0.041 g) to give the title compound (0.015 g).

LC-MS (System A): Rt 3.00 mins, Mass Spectrum m/z 463 [MH$^+$].

Example 15

N-{[4-(3,4-Dichlorobenzyl)morpholin-2-yl]methyl}-2-(3,4-dichlorophenyl)acetamide Example 15 was prepared in an analogous manner to Example 1 using a mixture of Intermediate 1 (0.055 g) and (3,4-dichlorophenyl)acetic acid (0.041 g) to give the title compound (0.015 g).

LC-MS (System A): Rt 2.93 mins, Mass Spectrum m/z 461 [MH$^+$].

Example 16

2-(2-Chlorophenyl)-N-{[4-(3,4-dichlorobenzyl)morpholin-2-yl]methyl}acetamide

Example 16 was prepared in an analogous manner to Example 1 using a mixture of Intermediate 1 (0.055 g) and (2-chlorophenyl)acetic acid (0.034 g) to give the title compound (0.025 g).

LC-MS (System A): Rt 2.67 mins, Mass Spectrum m/z 429 [MH$^+$].

Example 17

2-[3,5-Bis(trifluoromethyl)phenyl]-N-{[4-(3,4-dichlorobenzyl)morpholin-2-yl]methyl}acetamide Example 17 was prepared in an analogous manner to Example 1 using a mixture of Intermediate 1 (0.055 g) and [3,5-bis(trifluoromethyl)phenyl]acetic acid (0.054 g) to give the title compound (0.04 g).

LC-MS (System A): Rt 3.24 mins, Mass Spectrum m/z 529 [MH$^+$].

Example 18

N-{[4-(3,4-Dichlorobenzyl)morpholin-2-yl]methyl}-2-(2,4-dichlorophenyl)acetamide Example 18 was prepared in an analogous manner to Example 1 using a mixture of Intermediate 1 (0.055 g) and (2,4-dichlorophenyl)acetic acid (0.041 g) to give the title compound (0.019 g).

LC-MS (System A): Rt 2.72 mins, Mass Spectrum m/z 463 [MH$^+$].

Example 19

N-{[4-(3,4-Dichlorobenzyl)morpholin-2-yl]methyl}-2-(4-fluoro-2-methylphenyl)acetamide Example 19 was prepared in an analogous manner to Example 1 using a mixture of Intermediate 1 (0.055 g) and (4-fluoro-2-methylphenyl)acetic acid (0.034 g) to give the title compound (0.014 g).

LC-MS (System A): Rt 2.77 mins, Mass Spectrum m/z 425 [MH$^+$].

Example 20

N-{[4-(3,4-Dichlorobenzyl)morpholin-2-yl]methyl}-2-(2,6-dichlorophenyl)acetamide Example 20 was prepared in an analogous manner to Example 1 using a mixture of Intermediate 1 (0.055 g) and (2,6-dichlorophenyl)acetic acid (0.041 g) to give the title compound (0.011 g).

LC-MS (System A): Rt 2.81 mins, Mass Spectrum m/z 463 [MH$^+$].

Example 21

N-{[4-(3,4-Dichlorobenzyl)morpholin-2-yl]methyl}-2-phenoxyacetamide

Example 21 was prepared in an analogous manner to Example 1 using a mixture of Intermediate 1 (0.028 g) and phenoxyacetic acid (0.017 g) to give the title compound (0.026 g).

LC-MS (System A): Rt 2.74 min, Mass Spectrum m/z 409 [MH$^+$].

Example 22

N-{[4-(3,4-Dichlorobenzyl)morpholin-2-yl]methyl}-2-(4-methoxyphenyl)acetamide

Example 22 was prepared in an analogous manner to Example 1 using a mixture of Intermediate 1 (0.028 g) and (4-methoxyphenyl)acetic acid (0.018 g) to give the title compound (0.02 g).

LC-MS (System A): Rt 2.66 min, Mass Spectrum m/z 423 [MH$^+$].

Example 23

2-(4-Chlorophenyl)-N-{[4-(3,4-dichlorobenzyl)-5,5-dimethylmorpholin-2-yl]methyl}acetamide A mixture of Intermediate 3 (0.030 g) and 4-chlorophenylacetic acid (0.020 g) were treated with 1-methyl-2-pyrrolidinone (0.015 ml) then heated in a 600 W microwave oven, at full power, for 4 min. The crude mixture was purified by chromatography on silica gel (Varian Bond-Elut cartridge, 1 g) eluting with cyclohexane/ethyl acetate (19:1 followed by 1:1) to give a brown solid which was triturated with ether to give the title compound as an off-white solid (0.018 g).

LC-MS (System A): Rt 3.21 min, Mass Spectrum m/z 455 [MH$^+$].

Example 24

N-{[(cis)-4-(3,4-Dichlorobenzyl)-5-methylmorpholin-2-yl]methyl}-2-phenylacetamide A mixture of Intermediate 5 (0.060 g) and phenylacetic acid (0.027 g) was treated with 1-methyl-2-pyrrolidinone (0.015 ml) then heated in a 600 W microwave oven, at full power, for 4 min. The crude mixture was purified by normal phase preparative HPLC to give the title compound as a colourless gum (27 mg).

LC-MS (System A): Rt 2.85 min, Mass Spectrum m/z 407 [MH$^+$].

Example 25

N-{[(trans)-4-(3,4-Dichlorobenzyl)-5-methylmorpholin-2-yl]methyl}-2-phenylacetamide Example 25 was prepared in an analogous manner to Example 24 using a mixture of Intermediate 5 (0.06 g) and phenylacetic acid (0.027 g) to give the title compound as a colourless gum (18 mg).

LC-MS (System A): Rt 2.85 min, Mass Spectrum m/z 407 [MH$^+$].

Example 26

2-(4-Chlorophenyl)-N-{[(cis)-4-(3,4-dichlorobenzyl)-5-methylmorpholin-2-yl]methyl}acetamide Example 26 was prepared in an analogous manner to Example 24 using a mixture of Intermediate 5 (0.06 g) and (4-chlorophenyl)acetic acid (0.034 g) to give the title compound (0.027 g).

LC-MS (System A): Rt 3.10 min, Mass Spectrum m/z 441 [MH$^+$].

Example 27

2-(4-Chlorophenyl)-N-{[(trans)-4-(3,4-dichlorobenzyl)-5-methylmorpholin-2-yl]methyl}acetamide Example 27 was prepared in an analogous manner to Example 24 using a mixture of Intermediate 5 (0.06 g) and (4-chlorophenyl)acetic acid (0.034 g) to give the title compound (0.018 g).

LC-MS (System A): Rt 3.10 min, Mass Spectrum m/z 441 [MH$^+$].

Example 28

N-({4-[3-(3,4-Dichlorophenyl)propyl]morpholin-2-yl}methyl)-2-phenylacetamide

A mixture of Intermediate 7 (0.030 g) and phenylacetic acid (0.015 g) was treated with 1-methyl-2-pyrrolidinone (0.015 ml) then heated in a 600 W microwave oven, at full power, for 4 min. The crude mixture was purified by chromatography on silica gel (Varian Bond-Elut, 1 g) eluting with cyclohexane/ethyl acetate (4:1 followed by 2:1) to give the title compound as a colourless gum (0.004 g).

LC-MS (System A): Rt 2.74 min, Mass Spectrum m/z 421 [MH$^+$].

Example 29

2-(4Chlorophenyl)-N-{[4-(2,3-dichlorobenzyl)morpholin-2-yl]methyl}acetamide trifluoroacetate Intermediate 8 (0.060 g) was dissolved in methanol (10 ml) and loaded onto a solid phase extraction column (2 g Isolute SCX sulphonic acid) which had been prepared by application of methanol. Elution with methanol, then 0.880 ammonia: methanol 10:90 gave a clear colourless gum (0.027 g). This was treated with (4chlorophenyl)acetic acid (0.017 g) and N-methyl-2-pyrrolidinone (1 drop) and subjected to microwave irradiation (600 W, full power, 4 min). Purification by automated preparative HPLC (gradient profile 30-60% (ii) over 20 mins, R$_t$ 13 mins) gave the title compound (0.018 g) as a white solid.

LC/MS (System A): R$_t$ 2.87 min, Mass spectrum m/z 429 [MH$^+$].

Example 30

1-(4-Chlorophenyl)-N-{[4-(3,4-dichlorobenzyl)morpholin-2-yl]methyl}cyclopropanecarboxamide trifluoroacetate Example 30 was prepared in an analogous manner to Example 1 using a mixture of Intermediate 1 (0.055 g) and 1-(4-chlorophenyl)cyclopropanecarboxylic acid (0.039 g) to give the title compound (0.008 g).

LC-MS (System A): Rt 3.03 mins, Mass Spectrum m/z 455 [MH$^+$].

Example 31

N-{[4-(3,4-Dichlorobenzyl)morpholin-2-yl]methyl}-2-(5-methoxy-2-methyl-1H-indol-3-yl)acetamide Example 31 was prepared in an analogous manner to Example 1 using a mixture of Intermediate 1 (0.056 g) and (5-methoxy-2-methyl-1H-indol-3-yl)acetic acid (0.044 g) to give the title compound (0.019 g).

LC-MS (System A): Rt 2.63 mins, Mass Spectrum m/z 476 [MH$^+$].

Example 32

N-{[4-(3,4-Dichlorobenzyl)morpholin-2-yl]methyl}-2-thien-3-ylacetamide

Example 32 was prepared in an analogous manner to Example 1 using a mixture of Intermediate 1 (0.056 g) and thien-3-ylacetic acid (0.028 g) to give the title compound (0.016 g).

LC-MS (System A): Rt 2.50 mins, Mass Spectrum m/z 399 [MH$^+$].

Example 33

N-{[4-(3,4-Dichlorobenzyl)morpholin-2-yl]methyl}-2-(5-methyl-2-phenyl-1,3-oxazol-4-yl)acetamide Example 33 was prepared in an analogous manner to Example 1 using a mixture of Intermediate 1 (0.056 g) and (5-methyl-2-phenyl-1,3-oxazol-4-yl)acetic acid (0.043 g) to give the title compound (0.036 g).

LC-MS (System A): Rt 2.80 mins, Mass Spectrum m/z 474 [MH$^+$].

Example 34

N-{[4-(3,4-Dichlorobenzyl)morpholin-2-yl]methyl}-2-(5-methyl-1-phenyl-1H-pyrazol-4-yl)acetamide Example 34 was prepared in an analogous manner to Example 1 using a mixture of Intermediate 1 (0.056 g) and (5-methyl-1-phenyl-1H-pyrazol-4-yl)acetic acid (0.043 g) to give the title compound (0.014 g).

LC-MS (System A): Rt 2.61 mins, Mass Spectrum m/z 473 [MH$^+$].

Example 35

2-(4Bromo-3,5-dimethyl-1H-pyrazol-1-yl)-N-{[4-(3,4-dichlorobenzyl)morpholin-2-yl]methyl}acetamide Example 35 was prepared in an analogous manner to Example 1 using a mixture of Intermediate 1 (0.056 g) and (4-bromo-3,5dimethyl-1H-pyrazol-1-yl)acetic acid (0.047 g) to give the title compound (0.032 g).

LC-MS (System A): Rt 2.70 mins, Mass Spectrum m/z 491 [MH$^+$].

Example 36

N-{[4-(3,4-Dichlorobenzyl)morpholin-2-yl]methyl}-2-(2-phenyl-1,3-thiazol-4-yl)acetamide Example 36 was prepared in an analogous manner to Example 1 using a mixture of Intermediate 1 (0.056 g) and (2-phenyl-1,3-thiazol-4-yl)acetic acid (0.042 g) to give the title compound (0.049 g).

LC-MS (System A): Rt 2.85 mins, Mass Spectrum m/z 476 [MH$^+$].

Example 37

N-{[4-(3,4-Dichlorobenzyl)morpholin-2-yl]methyl}-2-(2-pyrazin-2-yl-1,3-thiazol-4-yl)acetamide Example 37 was prepared in an analogous manner to Example 1 using a mixture of Intermediate 1 (0.056 g) and (2-pyrazin-2-yl-1,3-thiazol-4-yl)acetic acid (0.044 g) to give the title compound (0.05 g).

LC-MS (System A): Rt 2.43 mins, Mass Spectrum m/z 478 [MH$^+$].

Chiral analytical HPLC, eluent 60% EtOH/n-heptane: Rt 9.22 min and 12.42 min.

Example 38

N-{[4-(3,4-Dichlorobenzyl)morpholin-2-yl]methyl}-2-(2-furyl)acetamide

Example 38 was prepared in an analogous manner to Example 1 using a mixture of Intermediate 1 (0.056 g) and 2-furylacetic acid (0.025 g) to give the title compound (0.044 g).

LC-MS (System A): Rt 2.38 mins, Mass Spectrum m/z 383 [MH$^+$].

Example 39

N-{[(2S)-4-(3,4-Dichlorobenzyl)morpholin-2-yl]methyl}-2-[4-(methylsulfonyl)phenyl]acetamide (Single Enantiomer of Example 2)

Example 39 was prepared in an analogous manner to Example 1 using a mixture of Intermediate 9 (0.055 g) and 4-(methylsulphonyl)phenylacetic acid (0.050 g) to give the title compound (0.045 g).

Chiral analytical HPLC, eluent 35% EtOH/n-heptane, Rt 20.56 min

Example 40

N-{[(2R)-4-(3,4-Dichlorobenzyl)morpholin-2-yl]methyl}-2-[4-(methylsulfonyl)phenyl]acetamide Example 40 was prepared in an analogous manner to Example 1 using a mixture of Intermediate 10 (0.055 g) and 4-(methylsulphonyl)phenylacetic acid (0.050 g) to give the title compound (0.046 g).

Chiral analytical HPLC, eluent 35% EtOH/n-heptane, Rt 17.16 min

Example 41

N-{[4-(3,4-Dichlorobenzyl)morpholin-2-yl]methyl}-2-[2-(4-fluorophenyl)-5-methyl-1,3-oxazol-4-yl]acetamide Intermediate 12 (0.050 g) was treated with N,N-dimethylformamide (0.5 ml) followed by 1-hydroxybenzotriazole hydrate (0.027 g), 1-[3-(dimethylamino)propyl]-3-ethylcarbodiimide hydrochloride (0.044 g) and Intermediate 1 (0.042 g) in N,N-dimethylformamide (0.5 ml) and N,N-diisopropylethylamine (0.027 ml). The mixture was stirred at 22° C. for 20 h, then left to stand for 6 days. The solution was diluted with dichloromethane (10 ml) and washed successively with dilute aqueous sodium hydrogen carbonate (10 ml) and dilute aqueous sodium chloride (2×10 ml). The organic phase was isolated using a hydrophobic frit (6 ml) and drained directly onto an SCX column (2 g Isolute SPE) which had been prepared by application of methanol. Elution with methanol, then 0.880 ammonia:methanol 10:90 gave the title compound (0.048 g) as an orange glassy solid.

LC/MS (System A) Rt 2.93 min. Mass spectrum m/z 492 [MH$^+$].

Example 42

N-{[(2S)-4-(3,4Dichlorobenzyl)morpholin-2-yl]methyl}-2-(2-pyrazin-2-yl-1,3-thiazol-4-yl)acetamide Chiral separation from the racemic mixture of Example 37:
Example 37 was separated into its single enantiomers with a chiral preparative HPLC system. The separation was carried out using a Chiralpak AD column (2 cm×25 cm), eluting with 60% ethanol in heptane (15 ml/min over 25 mins, UV detection λ=215 nm) to give the S isomer.

Chiral analytical HPLC, eluent 60% EtOH/n-heptane: Rt 12.22 min.

Example 43

N-{[(2R)-4-(3,4Dichlorobenzyl)morpholin-2-yl]methyl}-2-(2-pyrazin-2-yl-1,3-thiazol-4-yl)acetamide Example 43 was prepared in an analogous manner to Example 42 which similarly obtained the R isomer.
Chiral analytical HPLC, eluent 60% EtOH/n-heptane: Rt 9.20 min.

Example 44

N-[{(2S)-4-(3,4-Dichlorobenzyl)morpholin-2-yl]methyl}-2-(5-phenyl-2H-tetraazol-2-yl)acetamide A solution of (5-phenyl-2H-tetraazol-2-yl)acetic acid (0.082 g) in N,N-dimethylformamide (2 ml) under nitrogen was treated with O-(7-azabenzotriazol-1-yl)-N,N,N'N'-tetramethylammonium hexafluorophosphate (0.152 g) and N,N-diisopropylethylamine (0.139 ml) followed by a solution of Intermediate 9 (0.110 g) in N,N-dimethylformamide (3 ml), and the mixture was stirred at 22° C. for 4 h. The solvent was removed in vacuo and the residue dissolved in ethyl acetate (20 ml). The solution was washed with 10% aqueous citric acid (20 ml), brine (20 ml), saturated aqueous sodium hydrogen carbonate (20 ml) and brine (20 ml), dried (MgSO$_4$) and evaporated in vacuo. Purification by flash chromatography on silica gel (Merck 9385), eluting with ethyl acetate, followed by trituration of the resultant product with diethyl ether, gave the title compound as a white solid (0.184 g).

LCMS (System A): Rt 2.85 min. Mass Spectrum m/z 461 [MH$^+$].

Example 45

N-{[4-(3,4-Difluorobenzyl)morpholin-2-yl]methyl}-2-{4-[(methylsulfonyl)amino]phenyl}acetamide Example 45 was prepared in an analogous manner to Example 44 using a mixture of Intermediate 24 (0.014 g) and {4-[(methylsulfonyl)amino]phenyl}acetic acid (0.013 g) to give the title compound (0.022 g).

LC-MS (System A) Rt 2.09 mins. Mass Spectrum m/z 454 [MH$^+$].

Example 46

N-{[(2S)-4-(4-Fluorobenzyl)morpholin-2-yl]methyl}-2-{4-[(methylsulfonyl)amino]phenyl}acetamide Example 46 was prepared in an analogous manner to Example 44 using a mixture of Intermediate 24 (0.09 g) and 4-(methylsulphonylamino)phenylacetic acid (0.1 g) to give the title compound (0.077 g).

LC-MS (System A) Rt 2.05 mins. Mass Spectrum m/z 436 [MH$^+$].

Chiral analytical HPLC, eluent 15% EtOH/n-heptane: Rt 23.09 min.

Example 47

N-{[(2R)-4-(4-Fluorobenzyl)morpholin-2-yl]methyl}-2-{4-[(methylsulfonyl)amino]phenyl}acetamide Example 47 was prepared in an analogous manner to Example 44 using a mixture of Intermediate 24 (0.023 g) and 4-(methylsulphonylamino)phenylacetic acid (0.025 g) to give the title compound (0.01 g).

LC-MS (System A) Rt 2.06 mins. Mass Spectrum m/z 436 [MH$^+$].

Chiral analytical HPLC, eluent 15% EtOH/n-heptane: Rt 18.78 min.

Example 48

N-{[4-(4-Fluorobenzyl)morpholin-2-yl]methyl}-2-{4-[(methylsulfonyl)amino]phenyl}acetamide Example 48 was prepared in an analogous manner to Example 44 using a mixture of Intermediate 24 (0.013 g) and 4-(methylsulphonylamino)phenylacetic acid (0.013 g), with the exception that 1-(3-dimethylaminopropyl)-3-ethyl-carbodiimide hydrochloride and 1-hydroxybenzotriazole were used as the coupling reagents to give the title compound (0.019 g).

LC-MS (System A) Rt 2.01 mins Mass Spectrum m/z 436 [MH$^+$].

Chiral analytical HPLC, eluent 15% EtOH/n-heptane: Rt 19.40 min and 23.51 min.

Example 49

N-({(2S)-4-[(5-Chlorothien-2-yl)methyl]morpholin-2-yl}methyl)-2-{3-[(methylsulfonyl)amino]phenyl}acetamide Example 49 was prepared in an analogous manner to Example 44 using a mixture of Intermediate 14 (0.1 g) and Intermediate 18 (0.1 g) to give the title compound (0.102 g).

LC-MS (System A) Rt 2.23 mins. Mass Spectrum m/z 458 [MH$^+$].

Chiral analytical HPLC, eluent 20% EtOH/n-heptane: Rt 13.18 min.

Example 50

N-({(2R)-4-[(5-Chlorothien-2-yl)methyl]morpholin-2-yl}methyl)-2-{3-[(methylsulfonyl)amino]phenyl}acetamide Example 50 was prepared in an analogous manner to Example 44 using a mixture of Intermediate 14A (0.1 g) and Intermediate 18 (0.1 g) to give the title compound (0.085 g).

LC-MS (System A) Rt 2.27 mins. Mass Spectrum m/z 458 [MH$^+$].

Chiral analytical HPLC, eluent 20% EtOH/n-heptane: Rt 10.65 min.

Example 51

N-({4-[(5-Chlorothien-2-yl)methyl]morpholin-2-yl}methyl)-2-{3-[(methylsulfonyl)amino]phenyl}acetamide Example 51 was prepared in an analogous manner to Example 44 using a mixture of Intermediate 24 (0.007 g) and Intermediate 18 (0.007 g) with the exception that 1-(3-dimethylaminopropyl)-3-ethyl-carbodiimide hydrochloride and 1-hydroxybenzotriazole were used as the coupling reagents to give the title compound (0.0077 g).

LC-MS (System A) Rt 2.29 mins. Mass Spectrum m/z 458 [MH$^+$].

Chiral analytical HPLC, eluent 20% EtOH/n-heptane: Rt 10.67 min and 13.23 min.

Example 52

N-{[4-(3,4Dichlorobenzyl)morpholin-2-yl]methyl}-2-(2,6-difluorophenyl)acetamide

Example 52 was prepared in an analogous manner to Example 1 using a mixture of Intermediate 1 (0.055 g) and 2,6-difluorophenylacetic acid (0.035 g) to give the title compound (0.057 g).

LC-MS (System A) Rt 2.70 mins. Mass Spectrum m/z 429 [MH$^+$].

Example 53

N-Cyclopropyl-3-[2-({[4-(3,4-dichlorobenzyl)morpholin-2-yl]methyl}amino)-2-oxoethyl]benzamide A mixture of Example 57 (0.300 g), 1-hydroxybenzotriazole (0.171 g) and 1-(3-dimethylaminopropyl)-3-ethylcarbodiimide hydrochloride (0.098 g) was stirred in N,N-dimethylformamide (6.6 ml) and N,N-diisopropylethylamine (0.190 ml) was added. The mixture was stirred at 20° C. until a clear solution was obtained. A portion of the mixture (1.1 ml) was transferred into a flask, cyclopropylamine (0.0077 ml) was added, and the mixture was stirred at 20° C. under nitrogen for 17 h. Polystyrene methylisocyanate (Argonaut Technologies, 0.034g, loading 1.57 mmol/g) and macroporous triethylammonium methylpolystyrene carbonate (Argonaut Technologies, 0.015 g, loading 3.2 mmol/g) were added, and stirring was continued for 1 h. The mixture was filtered, the resin beads washed with methanol and the combined filtrates reduced in volume to approximately 1 ml and purified by solid phase extraction (2 g SCX cartridge), eluting with methanol followed by 10% 0.880 ammonia in methanol. The product was isolated by evaporation of the solvent from the basic fraction and was further purified by solid phase extraction (5 g Varian Bondelut silica gel cartridge), eluting successively with one column volume of dichloromethane, chloroform, ether, ethylacetate, acetone, acetonitrile and methanol, to give the title compound as a colourless gum (0.034 g).

LCMS (system A) R$_t$ 2.65 min. Mass Spectrum m/z 476, 478 [MH$^+$].

Example 54

N-{[(2S)-4-(3,4-Dichlorobenzyl)morpholin-2-yl]methyl}-2-(5-methyl-2-phenyl-1,3-oxazol-4-yl)acetamide Intermediate 16 (0.077 g) in anhydrous N,N-dimethylformamide (2 ml) was treated with N,N-diisopropylethylamine (0.044 ml) and 3,4-dichlorobenzyl chloride (0.035 ml). The mixture was stirred at 22° C. for 19 h, and partitioned between chloroform (15 ml) and saturated aqueous sodium bicarbonate (15 ml). The phases were separated using a hydrophobic frit and the organic phase loaded onto a solid phase extraction column (10 g SCX). Elution with methanol, then 0.880 ammonia:methanol 10:90 gave a clear colourless gum. The crude mixture was purified by flash chromatography on silica gel (Trikonex Flashtube™ 2008, 8 g), eluting with ethyl acetate, to give the title compound as a colourless gum (0.0023 g).

LC/MS (System A) R$_t$ 2.88 min. Mass spectrum m/z 474 [MH$^+$].

Chiral analytical HPLC, eluent 10% EtOH/n-heptane, R$_t$ 12.39 min.

Example 54 (Alternative Procedure)

N-{[(2S)-4-(3,4-Dichlorobenzyl)morpholin-2-yl]methyl}-2-(5-methyl-2-phenyl-1,3-oxazol-4-yl)acetamide Example 54 was prepared in an analogous manner to Example 1 using a mixture of Intermediate 9 (0.055 g) and 2-phenyl-5-methyl-4-oxazolylacetic acid (0.050 g) to give the title compound (0.046 g).

LC-MS (System A) Rt 2.88 mins. Mass Spectrum m/z 474 [MH$^+$].

Example 55

N-{[(2R)-4-(3,4Dichlorobenzyl)morpholin-2-yl]methyl}-2-(5-methyl-2-phenyl-1,3-oxazol-4-yl)acetamide Example 55 was prepared in an analogous manner to that described in Example 54 using Intermediate 17 (0.081 g) and 3,4-dichlorobenzyl chloride (0.037 ml) to give a colourless gum (0.011 g).

LC/MS (System A) R$_t$ 2.87 min. Mass spectrum m/z 474 [MH$^+$].

Chiral analytical HPLC, eluent 10% EtOH/n-heptane, R$_t$ 9.812 min.

Example 55 (Alternative Procedure)

N-{[(2R)-4-(3,4-Dichlorobenzyl)morpholin-2-yl]methyl}-2-(5-methyl-2-phenyl-1,3-oxazol-4-yl)acetamide Example 55 was prepared in an analogous manner to Example 1 using a mixture of Intermediate 10 (0.055 g) and 2-phenyl-5-methyl-4-oxazolylacetic acid (0.050 g) to give the title compound (0.042 g).

LC-MS (System A) Rt 2.88 mins. Mass Spectrum m/z 474 [MH$^+$].

A mixture of Examples 54 and 55: Chiral analytical HPLC, eluent 10% EtOH/n-heptane, R$_t$ 9.73 and 12.42 min.

Example 56

Methyl 3-[2-({[4-(3,4-dichlorobenzyl)morpholin-2-yl]methyl}amino)-2-oxoethyl]benzoate A mixture of [3-(methoxycarbonyl)phenyl]acetic acid (0.200 g), Intermediate 1 (0.284 g), 1-hydroxybenzotriazole (0.182 g) and 1-(3-dimethylaminopropyl)-3-ethylcarbodiimide hydrochloride (0.316 g) was stirred in dichloromethane (10 ml), and N,N-diisopropylethylamine (0.352 ml) was added to the solution. Stirring at 20° C. under nitrogen was continued for 8 h. The mixture was purified by solid phase extraction (2×10 g Varian Bondelut silica gel cartridges), eluting successively with one column volume of dichloromethane, chloroform, ether, ethyl acetate, acetone, acetonitrile and methanol, to give the title compound as a colourless gum, (0.266 g).

LCMS (system A) $R_t$ 2.70 min. Mass Spectrum m/z=451, 453 [MH$^+$].

Example 57

3-[2-({[4-(3,4-Dichlorobenzyl)morpholin-2-yl]methyl}amino)-2-oxoethyl]benzoic acid compound with N,N,N-triethylamine (1:1)

To a solution of Example 56 (0.261 g) in a mixture of water (4 ml) and methanol (12 ml) was added a solution of sodium hydroxide (0.054 g) in water (0.5 ml) and the mixture was stirred at 20° C. for 72 h. The pH of the mixture was adjusted to approximately 6 by the addition of 2N hydrochloric acid and the mixture was purified by solid phase extraction (10 g SCX cartridge), eluting with methanol followed by 10% triethylamine in methanol. Evaporation of the basic fraction in vacuo gave the title compound as a colourless gum, (0.319 g).

LCMS (system A) $R_t$ 2.66 min. Mass Spectrum m/z 437, 439 [MH$^+$].

Examples 58-85

| | Name | Preparation analogous to | Characterising Data |
|---|---|---|---|
| 58 | 2-[3-(acetylamino)phenyl]-N-{[4-(3,4-dichlorobenzyl)morpholin-2-yl]methyl}acetamide | Example 1 | LC-MS(System A): Rt 2.33 mins. Mass Spectrum m/z 450[MH$^+$]. |
| 59 | 2-(3-acetyl-1-benzothien-4-yl)-N-{[4-(3,4-dichlorobenzyl)morpholin-2-yl]methyl}acetamide trifluoroacetate | Example 1 | LC-MS(System A): Rt 2.90 mins. Mass Spectrum m/z 491[MH$^+$]. |
| 60 | 2-(5-bromopyridin-3-yl)-N-{[4-(3,4-dichlorobenzyl)morpholin-2-yl]methyl}acetamide compound with formic acid (1:1) | Example 1 | LC-MS(System A): Rt 2.57 mins. Mass Spectrum m/z 474[MH$^+$]. |
| 61 | N-{[4-(3,4-dichlorobenzyl)morpholin-2-yl]methyl}-2-(2,3-dimethylquinoxalin-6-yl)acetamide | Example 1 | LC-MS(System A): Rt 2.51 mins. Mass Spectrum m/z 473[MH$^+$]. |
| 62 | 2-(4-acetylphenyl)-N-{[4-(3,4-dichlorobenzyl)morpholin-2-yl]methyl}acetamide trifluoroacetate | Example 1 | LC-MS(System A): Rt 2.57 mins. Mass Spectrum m/z 435[MH$^+$]. |
| 63 | 2-(4-acetylphenyl)-N-{[4-(3,4-dichlorobenzyl)morpholin-2-yl]methyl}acetamide | Example 41 | LC-MS(System A): Rt 2.57 mins. Mass Spectrum m/z 435[MH$^+$]. |
| 64 | N-{[4-(3,4-dichlorobenzyl)morpholin-2-yl]methyl}-2-(4-isobutyrylphenyl)acetamide trifluoroacetate | Example 1 | LC-MS(System A): Rt 2.84 mins. Mass Spectrum m/z 463[MH$^+$]. |
| 65 | methyl 4-[2-({[4-(3,4-dichlorobenzyl)morpholin-2-yl]methyl}amino)-2-oxoethyl]benzoate trifluoroacetate | Example 1 | LC-MS(System A): Rt 2.65 mins. Mass Spectrum m/z 451[MH$^+$]. |
| 66 | methyl 4-[2-({[4-(3,4-dichlorobenzyl)morpholin-2-yl]methyl}amino)-2-oxoethyl]benzoate | Example 56 | LC-MS(System A): Rt 2.73 mins. Mass Spectrum m/z 451[MH$^+$]. |
| 67 | 2-(4-cyanophenyl)-N-{[4-(3,4-dichlorobenzyl)morpholin-2-yl]methyl}acetamide trifluoroacetate | Example 1 | LC-MS(System A): Rt 2.60 mins. Mass Spectrum m/z 418[MH$^+$]. |
| 68 | 2-(4-cyanophenyl)-N-{[4-(3,4-dichlorobenzyl)morpholin-2-yl]methyl}acetamide | Example 41 | LC-MS(System A): Rt 2.63 mins. Mass Spectrum m/z 418[MH$^+$]. |

-continued

| Name | Preparation analogous to | Characterising Data |
|---|---|---|
| 69 N-{[(2S,5R)-4-(3,4-dichlorobenzyl)-5-methylmorpholin-2-yl]methyl}-2-phenylacetamide | Example 24 from (2R)-2-aminopropan-1-ol | LC-MS(System A): Rt 2.88 mins. Mass Spectrum m/z 407[MH$^+$]. |
| 70 2-(4-chlorophenyl)-N-{[(2S,5R)-4-(3,4-dichlorobenzyl)-5-methylmorpholin-2-yl]methyl}acetamide | Example 24 | LC-MS(System A): Rt 3.13 mins. Mass Spectrum m/z 441[MH$^+$]. |
| 71 N-{[4-(3,4-dichlorobenzyl)morpholin-2-yl]methyl}-2-(3-fluoro-4-hydroxyphenyl)acetamide trifluoroacetate | Example 1 | LC-MS(System A): Rt 2.66 mins. Mass Spectrum m/z 427[MH$^+$]. |
| 72 N-{[(2S)-4-(3,4-dichlorobenzyl)morpholin-2-yl]methyl}-2-(2-furyl)acetamide | Example 42 | LC-MS(System A): Rt 2.38 mins. Mass Spectrum m/z 383[MH$^+$]. Chiral Analytical HPLC Eluent 20% EtOH/heptane Rt 9.97 mins. |
| 73 N-{[4-(3,4-dichlorobenzyl)morpholin-2-yl]methyl}-2-{4-[(4-methylpiperazin-1-yl)carbonyl]phenyl}acetamide | Example 53 | LC-MS(System A): Rt 2.25 mins. Mass Spectrum m/z 519[MH$^+$]. |
| 74 4-[2-({[4-(3,4-dichlorobenzyl)morpholin-2-yl]methyl}amino)-2-oxoethyl]-N-[2-(dimethylamino)ethyl]benzamide | Example 53 | LC-MS(System A): Rt 2.13 mins. Mass Spectrum m/z 507[MH$^+$]. |
| 75 4-[2-({[4-(3,4-dichlorobenzyl)morpholin-2-yl]methyl}amino)-2-oxoethyl]-N,N-dimethylbenzamide | Example 53 | LC-MS(System A): Rt 2.53 mins. Mass Spectrum m/z 464[MH$^+$]. |
| 76 4-[2-({[4-(3,4-dichlorobenzyl)morpholin-2-yl]methyl}amino)-2-oxoethyl]-N-ethylbenzamide | Example 53 | LC-MS(System A): Rt 2.57 mins. Mass Spectrum m/z 464[MH$^+$]. |
| 77 4-[2-({[4-(3,4-dichlorobenzyl)morpholin-2-yl]methyl}amino)-2-oxoethyl]-N-(2-hydroxyethyl)benzamide | Example 53 | LC-MS(System A): Rt 2.28 mins. Mass Spectrum m/z 480[MH$^+$]. |
| 78 N-{[4-(3,4-dichlorobenzyl)morpholin-2-yl]methyl}-2-[4-(morpholin-4-ylcarbonyl)phenyl]acetamide | Example 53 | LC-MS(System A): Rt 2.45 mins. Mass Spectrum m/z 506[MH$^+$]. |
| 79 N-{[(2S)-4-(3,4-dichlorobenzyl)morpholin-2-yl]methyl}-2-{3-[(dimethylamino)sulfonyl]phenyl}acetamide | Example 162 | LC-MS(System A): Rt 2.66 mins. Mass Spectrum m/z 500[MH$^+$]. |
| 80 N-{[(2R)-4-(3,4-dichlorobenzyl)morpholin-2-yl]methyl}-2-{4-[(dimethylamino)sulfonyl]phenyl}acetamide | Example 42 | LC-MS(System A): Rt 2.81 mins. Mass Spectrum m/z 500[MH$^+$]. Chiral Analytical HPLC Eluent 40% EtOH/heptane Rt 13.10 min. |

-continued

| | Name | Preparation analogous to | Characterising Data |
|---|---|---|---|
| 81 | N-{[(2S)-4-(3,4-dichlorobenzyl)morpholin-2-yl]methyl}-2-{4-[(dimethylamino)sulfonyl]phenyl}acetamide | Example 162 | LC-MS(System A): Rt mins 2.62. Mass Spectrum m/z 500[MH$^+$]. |
| 82 | 4-[2-({[4-(3,4-dichlorobenzyl)morpholin-2-yl]methyl}amino)-2-oxoethyl]-N-methylbenzamide | Example 53 | LC-MS(System A): Rt 2.49 mins. Mass Spectrum m/z 450[MH$^+$]. |
| 83 | 4-[2-({[4-(3,4-dichlorobenzyl)morpholin-2-yl]methyl}amino)-2-oxoethyl]-N-isopropylbenzamide | Example 53 | LC-MS(System A): Rt 2.69 mins. Mass Spectrum m/z 478[MH$^+$]. |
| 84 | N-cyclopropyl-4-[2-({[4-(3,4-dichlorobenzyl)morpholin-2-yl]methyl}amino)-2-oxoethyl]benzamide | Example 53 | LC-MS(System A): Rt 2.61 mins. Mass Spectrum m/z 476[MH$^+$]. |
| 85 | 4-[2-({[4-(3,4-dichlorobenzyl)morpholin-2-yl]methyl}amino)-2-oxoethyl]-N-(2-methoxyethyl)benzamide | Example 53 | LC-MS(System A): Rt 2.57 mins. Mass Spectrum m/z 494[MH$^+$]. |

Example 86

N-{[4-(3,4-dichlorobenzyl)morpholin-2-yl]methyl}-2-(5-phenyl-2H-tetraazol-2-yl)acetamide 2-(3,5-Dimethoxy-4-formylphenoxy)ethoxymethyl polystyrene resin (Novabiochem, loading 0.9 mmol/g, 1 g) was swollen with the minimum quantity of 1% acetic acid/N,N-dimethylformamide to form a slurry. Intermediate 1 (0.969 g) was added to this mixture in N,N-dimethylformamide (2 ml) and the mixture shaken at room temperature for 100 min. 1% Acetic acid/N,N-dimethylformamide (10 ml) was added followed by sodium triacetoxyborohydride (333 mg). The mixture was then shaken for 20 min before further sodium triacetoxyborohydride (0.300 g) was added, and shaking was continued at room temperature for 18 h. The reaction solution was then drained off and the resin washed with (N,N-dimethylformamide: 5×10 ml, methanol: 5×10 ml, dichloromethane: 5×10 ml, diethyl ether: 3×10 ml). The resin was then dried in vacuo.

The resin (0.100 g) was then swollen with dichloromethane, and excess solvent drained off. A solution of diisopropylcarbodiimide (0.0705 ml) and bromo acetic acid (0.125 g) in 1:1 dichloromethane/dimethyl formamide (1 ml), was made and stirred for ca. 5 min, before adding to the resin. The resin was then shaken at room temperature for 2 h. The solution was drained off and the resin washed with (N,N-dimethylformamide: 5×10 ml, methanol: 5×10 ml, dichloromethane: 5×10 ml).

A solution of potassium tert-butoxide (0.050 g) and the azole 5-phenyl-1-H-tetrazole (0.131 g) in N,N-dimethylformamide (1 ml) was prepared and stirred for 5 min before this was added to the resin. The reaction mixture was heated to 60° C. and shaken for 18 h. The reaction solution was then drained off and the resin washed with (N,N-dimethylformamide: 5×1 ml, methanol: 5×1 ml, dichloromethane: 5×1 ml).

1:1 trifluoroacetic acid/dichloromethane solution (1 ml) was then added to the resin, and the mixture shaken for 90 min. The resin was filtered off, washed with dichloromethane (1 ml), and the combined filtrate and washings evaporated. The resulting solid was purified by mass directed preparative HPLC to give the title compound (15 mg).

LC-MS (System A) R$_t$ 2.77 min. Mass Spectrum m/z 461 [MH$^+$].

Examples 87-90

| | Name | Preparation analogous to | Characterising Data |
|---|---|---|---|
| 87 | 2-(4-bromo-1H-imidazol-1-yl)-N-{[4-(3,4-dichlorobenzyl)morpholin-2-yl]methyl}acetamide | Example 86 | LC-MS(System A): Rt 2.34 mins. Mass Spectrum m/z 462[MH$^+$]. |
| 88 | N-{[4-(3,4-dichlorobenzyl)morpholin-2-yl]methyl}-2-(4-nitrophenyl)acetamide | Example 56 | LC-MS(System A): Rt 2.92 mins. Mass Spectrum m/z 438[MH$^+$]. |
| 89 | N-{[4-(3,4-dichlorobenzyl)morpholin-2-yl]methyl}-2-(3-nitrophenyl)acetamide | Example 56 | LC-MS(System A): Rt mins 2.92. Mass Spectrum m/z 438[MH$^+$]. |
| 90 | 2-[3-(acetylamino)phenyl]-N-{[4-(3-fluorobenzyl)morpholin-2-yl]methyl}acetamide | Example 91 | LC-MS(System A): Rt 2.13 mins. Mass Spectrum m/z 400[MH$^+$]. |

Example 91

N-{[4-(3-fluorobenzyl)morpholin-2-yl]methyl}-2-{4-[(methylsulfonyl)amino]phenyl}acetamide A mixture of Intermediate 29 (0.0134 g), {4-[(methylsulfonyl)amino]phenyl}acetic acid (0.0137 g, known compound WO 9929655 A1), 1-hydroxybenzotriazole (0.0097 g) and N,N-diisopropylethylamine (0.01 ml) in N,N-dimethylformamide (0.5 ml) was treated with a solution of 1-(3-dimethylaminopropyl)-3-ethylcarbodiimide hydrochloride (0.00138 g) in N,N-dimethylformamide (0.5 ml). The mixture was stirred at 20° C. for 24 h. The mixture was partitioned between dichloromethane (4 ml) and saturated aqueous sodium hydrogen carbonate (4 ml). The phases were separated and the organic phase applied to an ion exchange cartridge (2 g Isolute SCX, prewashed with methanol). The SCX cartridge was eluted with methanol (10 ml) followed by 10% 0.880 ammonia in methanol (10 ml) and the appropriate fractions were concentrated in vacuo to give the title compound as a colourless gum (0.0174 g).

LCMS (system A) $R_t$ 2.14 min. Mass Spectrum m/z 436 [MH$^+$].

Examples 92-134

| | Name | Preparation analogous to | Characterising Data |
|---|---|---|---|
| 92 | 2-[3-(acetylamino)phenyl]-N-{[4-(3,4-difluorobenzyl)morpholin-2-yl]methyl}acetamide | Example 91 | LC-MS(System A): Rt 2.31 mins. Mass Spectrum m/z 418[MH$^+$]. |
| 93 | 2-[4-(acetylamino)phenyl]-N-{[4-(3,4-difluorobenzyl)morpholin-2-yl]methyl}acetamide | Example 91 | LC-MS(System A): Rt 2.10 mins. Mass Spectrum m/z 418[MH$^+$]. |
| 94 | N-{[4-(3,4-difluorobenzyl)morpholin-2-yl]methyl}-2-(2-pyrazin-2-yl-1,3-thiazol-4-yl)acetamide | Example 91 | LC-MS(System A): Rt 2.09 mins. Mass Spectrum m/z 554[MH$^+$]. |
| 95 | N-{[4-(3,4-difluorobenzyl)morpholin-2-yl]methyl}-2-{3-[(methylsulfonyl)amino]phenyl}acetamide | Example 91 | LC-MS(System A): Rt 2.13 mins. Mass Spectrum m/z 446[MH$^+$]. |
| 96 | N-{[4-(3,4-difluorobenzyl)morpholin-2-yl]methyl}-2-[3-(methylsulfonyl)phenyl]acetamide | Example 91 | LC-MS(System A): Rt 2.04 mins. Mass Spectrum m/z 439[MH$^+$]. |
| 97 | N-{[4-(3-chlorobenzyl)morpholin-2-yl]methyl}-2-[4-(methylsulfonyl)phenyl]acetamide | Example 91 | LC-MS(System A): Rt 2.09 mins. Mass Spectrum m/z 437[MH$^+$]. |
| 98 | N-{[4-(3-chlorobenzyl)morpholin-2-yl]methyl}-2-[3-(methylsulfonyl)phenyl]acetamide | Example 91 | LC-MS(System A): Rt 2.11 mins. Mass Spectrum m/z 437[MH$^+$]. |
| 99 | 2-[3-(acetylamino)phenyl]-N-{[4-(4-fluorobenzyl)morpholin-2-yl]methyl}acetamide | Example 91 | LC-MS(System A): Rt 1.95 mins. Mass Spectrum m/z 400[MH$^+$]. |
| 100 | 2-[4-(acetylamino)phenyl]-N-{[4-(4-fluorobenzyl)morpholin-2-yl]methyl}acetamide | Example 91 | LC-MS(System A): Rt 1.91 mins. Mass Spectrum m/z 400[MH$^+$]. |
| 101 | N-{[4-(4-fluorobenzyl)morpholin-2-yl]methyl}-2-(2-pyrazin-2-yl-1,3-thiazol-4-yl)acetamide | Example 91 | LC-MS(System A): Rt 2.10 mins. Mass Spectrum m/z 428[MH$^+$]. |
| 102 | N-{[4-(2,3-dichlorobenzyl)morpholin-2-yl]methyl}-2-[4-(methylsulfonyl)phenyl]acetamide | Example 91 | LC-MS(System A): Rt 2.36 mins. Mass Spectrum m/z 471[MH$^+$]. |
| 103 | 2-[3-(acetylamino)phenyl]-N-{[4-(2,3-dichlorobenzyl)morpholin-2-yl]methyl}acetamide | Example 91 | LC-MS(System A): Rt 2.30 mins. Mass Spectrum m/z 450[MH$^+$]. |
| 104 | N-{[4-(2,3-dichlorobenzyl)morpholin-2-yl]methyl}-2-{4-[(methylsulfonyl)amino]phenyl}acetamide | Example 91 | LC-MS(System A): Rt 2.37 mins. Mass Spectrum m/z 486[MH$^+$]. |
| 105 | N-{[4-(2,3-dichlorobenzyl)morpholin-2-yl]methyl}-2-(4-{[(methylamino)carbonyl]amino}phenyl)acetamide | Example 91 | LC-MS(System A): Rt 2.24 mins. Mass Spectrum m/z 465[MH$^+$]. |
| 106 | N-{[4-(2,3-dichlorobenzyl)morpholin-2-yl]methyl}-2-(2-pyrazin-2-yl-1,3-thiazol-4-yl)acetamide | Example 91 | LC-MS(System A): Rt 2.44 mins. Mass Spectrum m/z 478[MH$^+$]. |
| 107 | N-({4-[(5-chlorothien-2-yl)methyl]morpholin-2-yl}methyl)-2-[4-(methylsulfonyl)phenyl]acetamide | Example 91 | LC-MS(System A): Rt 2.16 mins. Mass Spectrum m/z 443[MH$^+$]. |

-continued

| | Name | Preparation analogous to | Characterising Data |
|---|---|---|---|
| 108 | 2-[3-(acetylamino)phenyl]-N-({4-[(5-chlorothien-2-yl)methyl]morpholin-2-yl}methyl)acetamide | Example 91 | LC-MS(System A): Rt 2.13 mins. Mass Spectrum m/z 422[MH$^+$]. |
| 109 | N-({4-[(5-chlorothien-2-yl)methyl]morpholin-2-yl}methyl)-2-{4-[(methylsulfonyl)amino]phenyl}acetamide | Example 91 | LC-MS(System A): Rt 2.18 mins. Mass Spectrum m/z 458[MH$^+$]. |
| 110 | N-({4-[(5-chlorothien-2-yl)methyl]morpholin-2-yl}methyl)-2-(2-pyrazin-2-yl-1,3-thiazol-4-yl)acetamide | Example 91 | LC-MS(System A): Rt 2.26 mins. Mass Spectrum m/z 450[MH$^+$]. |
| 111 | 2-[3-(acetylamino)phenyl]-N-{[4-(3-chlorobenzyl)morpholin-2-yl]methyl}acetamide | Example 91 | LC-MS(System A): Rt 2.37 mins. Mass Spectrum m/z 416[MH$^+$]. |
| 112 | N-{[4-(3-chlorobenzyl)morpholin-2-yl]methyl}-2-{4-[(methylsulfonyl)amino]phenyl}acetamide | Example 91 | LC-MS(System A): Rt 2.37 mins. Mass Spectrum m/z 452[MH$^+$]. |
| 113 | 2-[4-(acetylamino)phenyl]-N-{[4-(3-chlorobenzyl)morpholin-2-yl]methyl}acetamide | Example 91 | LC-MS(System A): Rt 2.31 mins. Mass Spectrum m/z 416[MH$^+$]. |
| 114 | N-{[4-(3-chlorobenzyl)morpholin-2-yl]methyl}-2-(4-{[(methylamino)carbonyl]amino}phenyl)acetamide | Example 91 | LC-MS(System A): Rt 2.31 mins. Mass Spectrum m/z 431[MH$^+$]. |
| 115 | N-{[4-(3-chlorobenzyl)morpholin-2-yl]methyl}-2-(2-pyrazin-2-yl-1,3-thiazol-4-yl)acetamide | Example 91 | LC-MS(System A): Rt 2.46 mins. Mass Spectrum m/z 444[MH$^+$]. |
| 116 | 2-[4-(acetylamino)phenyl]-N-{[4-(2,3-dichlorobenzyl)morpholin-2-yl]methyl}acetamide | Example 91 | LC-MS(System A): Rt 2.51 mins. Mass Spectrum m/z 450[MH$^+$]. |
| 117 | N-{[4-(2,3-dichlorobenzyl)morpholin-2-yl]methyl}-2-[3-(methylsulfonyl)phenyl]acetamide | Example 91 | LC-MS(System A): Rt 2.43 mins. Mass Spectrum m/z 471[MH$^+$]. |
| 118 | 2-[4-(aminosulfonyl)phenyl]-N-{[4-(3,4-dichlorobenzyl)morpholin-2-yl]methyl}acetamide | Example 41 | LC-MS(System A): Rt 2.37 mins. Mass Spectrum m/z 472[MH$^+$]. |
| 119 | 2-[2-(acetylamino)phenyl]-N-{[4-(3,4-dichlorobenzyl)morpholin-2-yl]methyl}acetamide | Exampl(e 41 | LC-MS(System A): Rt 2.44 mins. Mass Spectrum m/z 450[MH$^+$]. |
| 120 | 2-(3-cyanophenyl)-N-{[4-(3,4-dichlorobenzyl)morpholin-2-yl]methyl}acetamide | Example 41 | LC-MS(System A): Rt 2.64 mins. Mass Spectrum m/z 418[MH$^+$]. |
| 121 | N-{[(2S,5R)-4-(2,5-dichlorobenzyl)-5-methylmorpholin-2-yl]methyl}-2-phenylacetamide | Example 24 | LC-MS(System A): Rt 2.73 mins. Mass Spectrum m/z 407[MH$^+$]. |
| 122 | 2-(4-chlorophenyl)-N-{[(2S,5R)-4-(2,5-dichlorobenzyl)-5-methylmorpholin-2-yl]methyl}acetamide | Example 24 | LC-MS(System A): Rt 3.02 mins. Mass Spectrum m/z 441[MH$^+$]. |
| 123 | N-{[4-(3,4-dichlorobenzyl)morpholin-2-yl]methyl}-2-(2-fluorophenyl)acetamide | Example 1 | LC-MS(System A): Rt 2.67 mins. Mass Spectrum m/z 411[MH$^+$]. |
| 124 | N-{[4-(3,4-dichlorobenzyl)morpholin-2-yl]methyl}-2-(2,3-difluorophenyl)acetamide | Example 1 | LC-MS(System A): Rt 2.75 mins. Mass Spectrum m/z 429[MH$^+$]. |
| 125 | N-{[4-(3,4-dichlorobenzyl)morpholin-2-yl]methyl}-2-(2,4-difluorophenyl)acetamide | Example 1 | LC-MS(System A): Rt 2.74 mins. Mass Spectrum m/z 429[MH$^+$]. |
| 126 | N-{[4-(3,4-dichlorobenzyl)morpholin-2-yl]methyl}-2-(2,5-difluorophenyl)acetamide | Example 1 | LC-MS(System A): Rt 2.73 mins. Mass Spectrum m/z 429[MH$^+$]. |
| 127 | 3-[2-({[4-(3,4-dichlorobenzyl)morpholin-2-yl]methyl}amino)-2-oxoethyl]-N-(2-methoxyethyl)benzamide | Example 53 | LC-MS(System A): Rt mins 2.57. Mass Spectrum m/z 494[MH$^+$]. |
| 128 | 3-[2-({[4-(3,4-dichlorobenzyl)morpholin-2-yl]methyl}amino)-2-oxoethyl]-N-ethylbenzamide | Example 53 | LC-MS(System A): Rt mins 2.65. Mass Spectrum m/z 464[MH$^+$]. |

| | Name | Preparation analogous to | Characterising Data |
|---|---|---|---|
| 129 | 3-[2-({[4-(3,4-dichlorobenzyl)morpholin-2-yl]methyl}amino)-2-oxoethyl]-N,N-dimethylbenzamide | Example 53 | LC-MS(System A): Rt 2.61 mins. Mass Spectrum m/z 464[MH$^+$]. |
| 130 | 3-[2-({[4-(3,4-dichlorobenzyl)morpholin-2-yl]methyl}amino)-2-oxoethyl]-N-[2-(dimethylamino)ethyl]benzamide | Example 53 | LC-MS(System A): Rt 2.27 mins. Mass Spectrum m/z 507[MH$^+$]. |
| 131 | N-{[4-(3,4-dichlorobenzyl)morpholin-2-yl]methyl}-2-{3-[(4-methylpiperazin-1-yl)carbonyl]phenyl}acetamide | Example 53 | LC-MS(System A): Rt 2.25 mins. Mass Spectrum m/z 519[MH$^+$]. |
| 132 | 2-(3-aminophenyl)-N-{[4-(3,4-dichlorobenzyl)morpholin-2-yl]methyl}acetamide | Example 56 | LC-MS(System A): Rt 2.26 mins. Mass Spectrum m/z 408[MH$^+$]. |
| 133 | 2-(4-aminophenyl)-N-{[4-(3,4-dichlorobenzyl)morpholin-2-yl]methyl}acetamide | Example 56 | LC-MS(System A): Rt 2.29 mins. Mass Spectrum m/z 408[MH$^+$]. |
| 134 | N-{[(2S)-4-(3,4-dichlorobenzyl)morpholin-2-yl]methyl}-2-(5-methyl-2-phenyl-1,3-oxazol-4-yl)acetamide hydrochloride | Example 54 | LC-MS(System A): Rt 2.90 mins. Mass Spectrum m/z 474[MH$^+$]. |

Example 135

N-{[(2S)-4-(3,4-dichlorobenzyl)morpholin-2-yl]methyl}-2-(5-methyl-2-phenyl-1,3-oxazol-4-yl)acetamide fumarate salt Example 54 (1 g) was dissolved in acetonitrile (10 ml) and methanol (3 ml). Fumaric acid (0.245 g) was added forming a slurry. The slurry was heated to and held at reflux for 1 h, during which time the reaction mixture became a solution. After 1 h heating, the solution was allowed to cool slowly to 23° C. Product was filtered off and washed with acetonitrile (2×5 ml), then dried in a vacuum oven at 50° C. for 16 h, to give the title compound as a white solid (0.35 g).

$^1$H nmr (400 MHz, d$_6$ DMSO) 13δ(2H, v.br.s, fumaric acid COOH), 8.03δ(1H, br.t, NH), 7.92-7.87δ(2H, m, aromatic CH's), 7.56δ(1H, d, aromatic CH), 7.52-7.46δ(4H, m, aromatic CH's), 7.27δ(1H, dd, aromatic CH), 6.62δ(2H, s, fumaric acid CH), 3.78δ(1H, ddd, CH), 3.53-3.44δ(2H, m, 2×CH), 3.43δ(2H, s, CH$_2$), 3.35δ(2H, s, CH$_2$), 3.12δ(2H, br.t, CH$_2$), 2.68δ(1H, br. dd, CH), 2.56δ(1H, dddd, CH), 2.31δ (3H, s, CH$_3$), 2.05δ(1H, ddd, CH), 1.82δ(1H, dd, CH).

Example 136-138

| | Name | Preparation analogous to | Characterising Data |
|---|---|---|---|
| 136 | 2-[4-(acetylamino)phenyl]-N-{[4-(3,4-dichlorobenzyl)morpholin-2-yl]methyl}acetamide | Example 139 | LC-MS(System A): Rt mins 2.49. Mass Spectrum m/z 450[MH$^+$]. |
| 137 | N-{4-[2-({[4-(3,4-dichlorobenzyl)morpholin-2-yl]methyl}amino)-2-oxoethyl]phenyl}-2-methylpropanamide | Example 139 | LC-MS(System A): Rt 2.77 mins. Mass Spectrum m/z 478[MH$^+$]. |
| 138 | N-{3-[2-({[4-(3,4-dichlorobenzyl)morpholin-2-yl]methyl}amino)-2-oxoethyl]phenyl}-2-methylpropanamide | Example 139 | LC-MS(System A): Rt 2.77 mins. Mass Spectrum m/z 478[MH$^+$]. |

Example 139

N-{[4-(3,4-dichlorobenzyl)morpholin-2-yl]methyl}-2-{3-[(methylsulfonyl)amino]phenyl}acetamide Methanesulphonylchloride (0.022 ml) was added to a stirred solution of Example 132 (0.114 g) in dichloromethane (5 ml), and stirring was continued at 22° C. for 2 h. After leaving to stand for a further 112 h, tris-(2-aminoethyl)amine polystyrene resin (0.026 g) was added and stirring continued for a further 2 h. N,N-Dimethylformamide (1 ml) was added and the mixture applied to a 10 g ion exchange cartridge (Isolute SCX, pre-conditioned with methanol). Elution with methanol (3 column volumes) followed by 10% 0.880 ammonia in methanol (2 column volumes) and evaporation of the first basic fraction gave a residue, which was re-dissolved in dichloromethane, treated with polystyrene methylisocyanate resin (3.85 mmol/g, 0.026 g), and left to stand for 1 h. The mixture was applied to a 10 g silica gel cartridge (Varian Bond Elut, pre-conditioned with dichloromethane), and eluted with 1 column volume each of dichloromethane, chloroform, ether, ethyl acetate, acetone, acetonitrile and methanol. The appropriate fraction was evaporated in vacuo to give the title compound as a colourless gum (0.115 g).

LC/MS (system A) $R_t$ 2.65 min Mass Spectrum m/z 486 [MH$^+$]

Examples 140-150

| | Name | Preparation analogous to | Characterising Data |
|---|---|---|---|
| 140 | N-{[(2S,5R)-4-(3,4-dichlorobenzyl)-5-methylmorpholin-2-yl]methyl}-2-(5-methyl-2-phenyl-1,3-oxazol-4-yl)acetamide | Example 24 | LC-MS(System A): Rt 2.93 mins. Mass Spectrum m/z 488[MH$^+$]. Normal Phase Analytical HPLC RT 14.31 mins. |
| 141 | N-{[4-(3,4-dichlorobenzyl)morpholin-2-yl]methyl}-2-{4-[(methylsulfonyl)amino]phenyl}acetamide | Example 139 | LC-MS(System A): Rt 2.57 mins. Mass Spectrum m/z 486[MH$^+$]. |
| 142 | N-{3-[2-({[4-(3,4-dichlorobenzyl)morpholin-2-yl]methyl}amino)-2-oxoethyl]phenyl}-2-(dimethylamino)acetamide | Example 136 | LC-MS(System A): Rt 2.29 mins. Mass Spectrum m/z 493[MH$^+$]. |
| 143 | 2-{4-[bis(methylsulfonyl)amino]phenyl}-N-{[4-(3,4-dichlorobenzyl)morpholin-2-yl]methyl}acetamide | Example 139 | LC-MS(System A): Rt 2.62 mins. Mass Spectrum m/z 564, 566[MH$^+$]. |
| 144 | N-{[4-(3,4-dichlorobenzyl)morpholin-2-yl]methyl}-2-(5-methyl-2-phenyl-1,3-thiazol-4-yl)acetamide | Example 41 | LC-MS(System A): Rt 3.05 mins. Mass Spectrum m/z 490[MH$^+$]. |
| 145 | N-{[4-(3,4-dichlorobenzyl)morpholin-2-yl]methyl}-2-(5-methyl-2-pyrazin-2-yl-1,3-thiazol-4-yl)acetamide | Example 41 | LC-MS(System A): Rt 2.60 mins. Mass Spectrum m/z 492[MH$^+$]. |
| 146 | N-{[4-(3,4-dichlorobenzyl)morpholin-2-yl]methyl}-2-[3-(methylsulfonyl)phenyl]acetamide | Example 56 | LC-MS(System A): Rt 2.61 mins. Mass Spectrum m/z 471[MH$^+$]. |
| 147 | N-{[4-(3,4-dichlorobenzyl)morpholin-2-yl]methyl}-2-[4-(methylsulfonyl)-2-nitrophenyl]acetamide | Example 41 | LC-MS(System A): Rt 2.6 mins. Mass Spectrum m/z 518[MH$^+$]. |
| 148 | N-{[4-(3,4-dichlorobenzyl)morpholin-2-yl]methyl}-2-(2-hydroxyphenyl)acetamide | Example 41 | LC-MS(System A): Rt 2.52 mins. Mass Spectrum m/z 409[MH$^+$]. |
| 149 | N-{[4-(3,4-dichlorobenzyl)morpholin-2-yl]methyl}-2-(2-phenyl-1,3-oxazol-4-yl)acetamide | Example 41 | LC-MS(System A): Rt 2.78 mins. Mass Spectrum m/z 460[MH$^+$]. |
| 150 | N-{[4-(3,4-dichlorobenzyl)morpholin-2-yl]methyl}2-{4-[methyl(methylsulfonyl)amino]phenyl}acetamide | Example 151 | LC-MS(System A): Rt 2.73 mins. Mass Spectrum m/z 500[MH$^+$]. |

Example 151

N-{[4-(3,4-dichlorobenzyl)morpholin-2-yl]methyl}-2-{3-[methyl(methylsulfonyl)amino]phenyl}acetamide Potassium carbonate (0.035 g) and iodomethane (0.015 ml) were added to a stirred solution of Example 139 (0.115 g) in acetone (1 ml), and stirring was continued at 22° C. for 72 h before a further portion of iodomethane (0.003 ml) was added. After stirring for a further 24 h, more iodomethane (0.003 ml) and potassium carbonate (0.007 g) were added, and the mixture stirred for a further 48 h. The mixture was applied in two equal portions to two ion exchange cartridges (2 g Isolute SCX, pre-conditioned with methanol). Elution with methanol (3 column volumes) followed by 10% 0.880 ammonia in methanol (2 column volumes), and evaporation of the first basic fraction from each elution in vacuo gave the title compound as a pale yellow gum (0.038 g).

LC/MS (system A) $R_t$ 2.73 min Mass Spectrum m/z 500 [MH$^+$]

Examples 152-157

Example 158

N-{[(2S)-4-(3,4-Dichlorobenzyl)morpholin-2-yl]methyl}-2-(5-methyl-2-pyridin-3-yl-1,3-oxazol-4-yl)acetamide Compound with formic acid (1:1)

N,N'-carbonyldiimidazole (15 mg) was added to a stirred solution of Intermediate 34 (20 mg) at 22° C. under nitrogen, and the mixture was stirred at 22° C. for 1 h. Intermediate 9 (26 mg) was added and the mixture stirred at 22° C. for 24 h. The mixture was applied directly to a sulphonic acid ion exchange cartridge (Isolute SCX, 2 g) and eluted with methanol followed by 10% 0.880 ammonia in methanol. Evaporation of the methanolic ammonia fraction gave a gum (50 mg) which was further purified by solid phase extraction on silica gel (1 g Varian Bondelut cartridge), eluting with chloroform, ether, ethyl acetate, acetone and methanol to give a gum (38 mg). The gum was partitioned between dichloromethane and water, and the organic layer treated with polystyrene methylisocyanate resin (Argonaut, 95 mg, 1.6 mmol/g). After shaking for 4 h the resin was filtered off and the filtrate evaporated to give a gum (29 mg), which was further purified by chro-

| | Name | Preparation analogous to | Characterising Data |
|---|---|---|---|
| 152 | N-{[(2S)-4-(3,4-dichlorobenzyl)morpholin-2-yl]methyl}-4-(methylsulfonyl)butanamide | Example 44 | LC-MS(System A): Rt 2.18 mins. Mass Spectrum m/z 423[MH$^+$] |
| 153 | N-{[4-(3,4-dichlorobenzyl)morpholin-2-yl]methyl}-2-[5-methyl-2-(5-methylthien-2-yl)-1,3-oxazol-4-yl]acetamide | Example 41 | LC-MS(System A): Rt 2.87 mins. Mass Spectrum m/z 494[MH$^+$]. |
| 154 | 2-[2-amino-4-(methylsulfonyl)phenyl]-N-{[4-(3,4-dichlorobenzyl)morpholin-2-yl]methyl}acetamide | Example 41 | LC-MS(System A): Rt 2.36 mins. Mass Spectrum m/z 486[MH$^+$]. |
| 155 | N-{[4-(3,4-dichlorobenzyl)morpholin-2-yl]methyl}-2-(5-methyl-2-thien-2-yl-1,3-oxazol-4-yl)acetamide | Example 41 | LC-MS(System A): Rt 2.79 mins. Mass Spectrum m/z 480[MH$^+$]. |
| 156 | N-{[4-(3,4-dichlorobenzyl)morpholin-2-yl]methyl}-2-[2-(2-furyl)-5-methyl-1,3-oxazol-4-yl]acetamide | Example 41 | LC-MS(System A): Rt 2.64 mins. Mass Spectrum m/z 464[MH$^+$]. |
| 157 | N-{[4-(3,4-dichlorobenzyl)morpholin-2-yl]methyl}pent-4-ynamide | Example 1 | LC-MS(System A): Rt 2.30 mins. Mass Spectrum m/z 355[MH$^+$]. | matography on silica gel, eluting with dichloromethane: ethanol: 0.880 ammonia 100:0:0-95:5:0.5, followed by mass directed preparative HPLC to give the title compound (7.6 mg).

LC-MS (System A) Rt 2.48 min. Mass Spectrum m/z 475 [MH$^+$].

Examples 159-161

| | Name | Preparation analogous to | Characterising Data |
|---|---|---|---|
| 159 | N-{[(2S)-4-(3,4-dichlorobenzyl)morpholin-2-yl]methyl}-2-(2-isopropyl-5-methyl-1,3-oxazol-4-yl)acetamide | Example 158 | LC-MS(System A): Rt 2.66 mins. Mass Spectrum m/z 440[MH$^+$]. |
| 160 | N-{[(2S)-4-(3,4-dichlorobenzyl)morpholin-2-yl]methyl}-2-{4-[(methylamino)sulfonyl]phenyl}acetamide | Example 162 | LC-MS(System A): Rt 2.50 mins. Mass Spectrum m/z 486[MH$^+$]. |
| 161 | N-{[(2S)-4-(3,4-dichlorobenzyl)morpholin-2-yl]methyl}-2-{4-[(ethylamino)sulfonyl]phenyl}acetamide | Example 162 | LC-MS(System A): Rt 2.58 mins. Mass Spectrum m/z 500[MH$^+$]. |

Example 162

2-[3-(Aminosulfonyl)phenyl]-N-{[(2S)-4-(3,4-dichlorobenzyl)morpholin-2-yl]methyl}acetamide To a stirred solution of Intermediate 40 (0.021 g) in N,N-dimethylformamide (1 ml) was added 1-hydroxybenzotriazole (0.015 g), N,N-diisopropylethylamine (0.028 ml) and 1-(3-dimethylaminopropyl)-3-ethylcarbodiimide hydrochloride (0.025 g) followed by a solution of Intermediate 9 (0.023 g) in N,N-dimethylformamide (1 ml). The mixture was stirred for 4 h at 22° C., and applied to an ion exchange cartridge (2 g Isolute SCX, pre-conditioned with methanol). Elution with methanol (3 column volumes) followed 10% 0.880 ammonia in methanol (2 column volumes) and evaporation of the first basic fraction in vacuo gave a residue which was re-dissolved in dichloromethane and applied to a silica gel cartridge (2g Varian Bond Elut, pre-conditioned with dichloromethane). Elution with dichloromethane, chloroform, ether, ethyl acetate, acetone, acetonitrile and methanol (1 column volume each), and evaporation of the product containing fractions in vacuo gave the title compound as a yellow gum (0.026 g).

LCMS (System A) R$_t$ 2.38 min Mass Spectrum m/z 472 [MH$^+$].

Chiral Analytical HPLC on Chiralcel OD-H column, detection at 230 nm, eluent 25% EtOH/n-heptane, Rt 12.4 min.

Examples 162A-213

| | Name | Preparation analogous to | Characterising Data |
|---|---|---|---|
| 162A | 2-[3-(Aminosulfonyl)phenyl]-N-{[4-(3,4-dichlorobenzyl)morpholin-2-yl]methyl}acetamide | Example 162 (from Intermediate 1) | LC-MS(System A): Rt 2.36 mins. Mass Spectrum m/z 472[MH$^+$]. Chiral Analytical HPLC on Chiralcel OD-H column, detection at 230 nm, eluent 25% EtOH/n-heptane, Rt 12.5 min and 10.3 min. |
| 163 | 2-{3-[(cyclopropylamino)sulfonyl]phenyl}-N-{[(2S)-4-(3,4-dichlorobenzyl)morpholin-2-yl]methyl}acetamide | Example 162 | LC-MS(System A): Rt 2.66 mins. Mass Spectrum m/z 512[MH$^+$]. |
| 164 | N-{[(2S)-4-(3,4-dicholorobenzyl)morpholin-2-yl]methyl}-2-{3-[(ethylamino)sulfonyl]phenyl}acetamide | Example 162 | LC-MS(System A): Rt 2.62 mins. Mass Spectrum m/z 500[MH$^+$]. |

| | Name | Preparation analogous to | Characterising Data |
|---|---|---|---|
| 165 | N-{[(2S)-4-(3,4-dichlorobenzyl)morpholin-2-yl]methyl}-2-{3-[(methylamino)sulfonyl]phenyl}acetamide | Example 162 | LC-MS(System A): Rt 2.50 mins. Mass Spectrum m/z 486[MH$^+$]. |
| 166 | N-{[(2S)-4-(3,4-dichlorobenzyl)morpholin-2-yl]methyl}-2-(5-methyl-2-morpholin-4-yl-1,3-oxazol-4-yl)acetamide | Example 41 | LC-MS(System A): Rt 2.41 mins. Mass Spectrum m/z 483[MH$^+$]. |
| 167 | 2-[4-(aminosulfonyl)phenyl]-N-{[4-(3,4-dichlorobenzyl)morpholin-2-yl]methyl}acetamide | Example 162 | LC-MS(System A): Rt 2.34 mins. Mass Spectrum m/z 472[MH$^+$]. |
| 168 | 2-{4-[(cyclopropylamino)sulfonyl]phenyl}-N-{[4-(3,4-dichlorobenzyl)morpholin-2-yl]methyl}acetamide | Example 162 | LC-MS(System A): Rt 2.65 mins. Mass Spectrum m/z 512[MH$^+$]. |
| 169 | methyl 2-[2-({[4-(3,4-dichlorobenzyl)morpholin-2-yl]methyl}amino)-2-oxoethyl]-2H-1,2,3-benzotriazole-5-carboxylate | Example 86 | LC-MS(System A): Rt 2.76 mins. Mass Spectrum m/z 492[MH$^+$]. |
| 170 | N-{[4-(3,4-dichlorobenzyl)morpholin-2-yl]methyl}-2-(1H-pyrrolo[2,3-b]pyridin-1-yl)acetamide | Example 86 | LC-MS(System A): Rt 2.59 mins. Mass Spectrum m/z 433[MH$^+$]. |
| 171 | N-{[4-(3,4-dichlorobenzyl)morpholin-2-yl]methyl}-2-(5-pyridin-2-yl-2H-tetraazol-2-yl)acetamide | Example 86 | LC-MS(System A): Rt 2.48 mins. Mass Spectrum m/z 462[MH$^+$]. |
| 172 | N-{[4-(3,4-dichlorobenzyl)morpholin-2-yl]methyl}-2-(5-pyridin-3-yl-2H-tetraazol-2-yl)acetamide | Example 86 | LC-MS(System A): Rt 2.45 mins. Mass Spectrum m/z 462[MH$^+$]. |
| 173 | N-{[4-(3,4-dichlorobenzyl)morpholin-2-yl]methyl}-2-[5-(3-formylphenyl)-2H-tetraazol-2-yl]acetamide | Example 86 | LC-MS(System A): Rt 2.77 mins. Mass Spectrum m/z 489[MH$^+$]. |
| 174 | methyl 1-[2-({[4-(3,4-dichlorobenzyl)morpholin-2-yl]methyl}amino)-2-oxoethyl]-1H-1,2,3-benzotriazole-5-carboxylate, compound with methyl 1-[2-({[4-(3,4-dichlorobenzyl)morpholin-2-yl]methyl}amino)-2-oxoethyl]-1H-1,2,3-benzotriazole-6-carboxylate (1:1) | Example 86 | LC-MS(System A): Rt 2.66 mins. Mass Spectrum m/z 492[MH$^+$]. |
| 175 | N-{[(2S)-4-(3,4-dichlorobenzyl)morpholin-2-yl]methyl}-2-[2-(2-furyl)-5-methyl-1,3-oxazol-4-yl]acetamide | Example 41 | LC-MS(System A): Rt 2.65 mins. Mass Spectrum m/z 464[MH$^+$]. |
| 176 | N-{[(2S)-4-(3,4-dichlorobenzyl)morpholin-2-yl]methyl}-2-(5-methyl-2-thien-2-yl-1,3-oxazol-4-yl)acetamide | Example 41 | LC-MS(System A): Rt 2.80 mins. Mass Spectrum m/z 478[MH$^+$]. |
| 177 | N-({(2S)-4-[(5-chlorothien-2-yl)methyl]morpholin-2-yl}methyl)-2-(5-methyl-2-phenyl-1,3-oxazol-4-yl)acetamide | Example 41 | LC-MS(System A): Rt 2.75 mins. Mass Spectrum m/z 446[MH$^+$]. |
| 178 | N-{[(2S)-4-(2,3-dichlorobenzyl)morpholin-2-yl]methyl}-2-(5-methyl-2-phenyl-1,3-oxazol-4-yl)acetamide | Example 41 | LC-MS(System A): Rt 2.97 mins. Mass Spectrum m/z 474[MH$^+$]. |
| 179 | N-({(2S)-4-[(5-chlorothien-2-yl)methyl]morpholin-2-yl}methyl)-2-[2-(4-fluorophenyl)-5-methyl-1,3-oxazol-4-yl]acetamide | Example 41 | LC-MS(System A): Rt 2.82 mins. Mass Spectrum m/z 464[MH$^+$]. |
| 180 | N-{[(2S)-4-(4-fluorobenzyl)morpholin-2-yl]methyl}-2-[2-(4-fluorophenyl)-5-methyl-1,3-oxazol-4-yl]acetamide | Example 41 | LC-MS(System A): Rt 2.54 mins. Mass Spectrum m/z 442[MH$^+$]. |
| 181 | N-{[(2S)-4-(2,3-dichlorobenzyl)morpholin-2-yl]methyl}-2-[2-(4-fluorophenyl)-5-methyl-1,3-oxazol-4-yl]acetamide | Example 54 | LC-MS(System A): Rt 2.97 mins. Mass Spectrum m/z 492[MH$^+$]. |

| | Name | Preparation analogous to | Characterising Data |
|---|---|---|---|
| 182 | N-({(2S)-4-[(5-chlorothien-2-yl)methyl]morpholin-2-yl}methyl)-2-(2-phenyl-1,3-oxazol-4-yl)acetamide | Example 41 | LC-MS(System A): Rt 2.64 mins. Mass Spectrum m/z 432[MH$^+$]. |
| 183 | N-{[(2S)-4-(4-fluorobenzyl)morpholin-2-yl]methyl}-2-(2-phenyl-1,3-oxazol-4-yl)acetamide | Example 41 | LC-MS(System A): Rt 2.39 mins. Mass Spectrum m/z 410[MH$^+$]. |
| 184 | N-{[(2S)-4-(2,3-dichlorobenzyl)morpholin-2-yl]methyl}-2-(2-phenyl-1,3-oxazol-4-yl)acetamide | Example 41 | LC-MS(System A): Rt 2.86 mins. Mass Spectrum m/z 460[MH$^+$]. |
| 185 | N-{[(2S)-4-(3,4-difluorobenzyl)morpholin-2-yl]methyl}-2-(5-methyl-2-phenyl-1,3-oxazol-4-yl)acetamide | Example 41 | LC-MS(System A): Rt 2.59 mins. Mass Spectrum m/z 442[MH$^+$]. |
| 186 | N-{[(2S)-4-(3-chlorobenzyl)morpholin-2-yl]methyl}-2-(5-methyl-2-phenyl-1,3-oxazol-4-yl)acetamide | Example 41 | LC-MS(System A): Rt 2.63 mins. Mass Spectrum m/z 440[MH$^+$]. |
| 187 | N-{[(2S)-4-(3,4-difluorobenzyl)morpholin-2-yl]methyl}-2-[2-(4-fluorophenyl)-5-methyl-1,3-oxazol-4-yl]acetamide | Example 41 | LC-MS(System A): Rt 2.64 mins. Mass Spectrum m/z 460[MH$^+$]. |
| 188 | N-{[((2S)-4-(3-chlorobenzyl)morpholin-2-yl]methyl}-2-[2-(4-fluorophenyl)-5-methyl-1,3-oxazol-4-yl]acetamide | Example 41 | LC-MS(System A): Rt 2.68 mins. Mass Spectrum m/z 458[MH$^+$]. |
| 189 | N-{[(2S)-4-(3,4-difluorobenzyl)morpholin-2-yl]methyl}-2-(2-phenyl-1,3-oxazol-4-yl)acetamide | Example 41 | LC-MS(System A): Rt 2.50 mins. Mass Spectrum m/z 428[MH$^+$]. |
| 190 | N-{[(2S)-4-(3-chlorobenzyl)morpholin-2-yl]methyl}-2-(2-phenyl-1,3-oxazol-4-yl)acetamide | Example 41 | LC-MS(System A): Rt 2.54 mins. Mass Spectrum m/z 426[MH$^+$]. |
| 191 | N-{[(2S)-4-(3,4-dichlorobenzyl)morpholin-2-yl]methyl}-2-[2-(4-fluorophenyl)-5-methyl-1,3-oxazol-4-yl]acetamide | Example 54 | LC-MS(System A): Rt 2.90 mins. Mass Spectrum m/z 492[MH$^+$]. |
| 192 | N-{[(2S)-4-(3,4-dichlorobenzyl)morpholin-2-yl]methyl}-2-(2-phenyl-1,3-oxazol-4-yl)acetamide | Example 41 | LC-MS(System A): Rt 2.81 mins. Mass Spectrum m/z 460[MH$^+$]. |
| 193 | N-cyclopropyl-3-[2-({[(2S)-4-(2,3-dichlorobenzyl)morpholin-2-yl]methyl}amino)-2-oxoethyl]benzamide | Example 41 | LC-MS(System A): Rt 2.45 mins. Mass Spectrum m/z 476[MH$^+$]. |
| 194 | 3-{2-[({(2S)-4-[(5-chlorothien-2-yl)methyl]morpholin-2-yl}methyl)amino]-2-oxoethyl}-N-cyclopropylbenzamide | Example 41 | LC-MS(System A): Rt 2.28 mins. Mass Spectrum m/z 447[MH$^+$]. |
| 195 | N-cyclopropyl-3-(2-({[(2S)-4-(4-fluorobenzyl)morpholin-2-yl]methyl}amino)-2-oxoethyl]benzamide | Example 41 | LC-MS(System A): Rt 2.11 mins. Mass Spectrum m/z 425[MH$^+$]. |
| 196 | 3-[2-({[(2S)-4-(3-chlorobenzyl)morpholin-2-yl]methyl}amino)-2-oxoethyl]-N-cyclopropylbenzamide | Example 41 | LC-MS(System A): Rt 2.24 mins. Mass Spectrum m/z 442[MH$^+$]. |
| 197 | N-cyclopropyl-3-(2-({[(2S)-4-(3,4-difluorobenzyl)morpholin-2-yl]methyl}amino)-2-oxoethyl]benzamide | Example 41 | LC-MS(System A): Rt 2.12 mins. Mass Spectrum m/z 444[MH$^+$]. |
| 198 | N-cyclopropyl-3-(2-({[(2S)-4-(3,4-dichlorobenzyl)morpholin-2-yl]methyl}amino)-2-oxoethyl]benzamide | Example 41 | LC-MS(System A): Rt 2.46 mins. Mass Spectrum m/z 476[MH$^+$]. |
| 199 | N-{[(2S)-4-(2,3-dichlorobenzyl)morpholin-2-yl]methyl}-2-(5-phenyl-2H-tetraazol-2-yl)acetamide | Example 41 | LC-MS(System A): Rt 2.90 mins. Mass Spectrum m/z 461[MH$^+$]. |
| 200 | N-{[(2S)-4-(4-fluorobenzyl)morpholin-2-yl]methyl}-2-(5-phenyl-2H-tetraazol-2-yl)acetamide | Example 41 | LC-MS(System A): Rt 2.42 mins. Mass Spectrum m/z 410[MH$^+$]. |

| | Name | Preparation analogous to | Characterising Data |
|---|---|---|---|
| 201 | N-{[(2S)-4-(3-chlorobenzyl)morpholin-2-yl]methyl}-2-(5-phenyl-2H-tetraazol-2-yl)acetamide | Example 41 | LC-MS(System A): Rt 2.57 mins. Mass Spectrum m/z 427[MH$^+$]. |
| 202 | N-{[(2S)-4-(3,4-difluorobenzyl)morpholin-2-yl]methyl}-2-(5-phenyl-2H-tetraazol-2-yl)acetamide | Example 41 | LC-MS(System A): Rt 2.53 mins. Mass Spectrum m/z 429[MH$^+$]. |
| 203 | N-{[(2S)-4-(3,4-dichlorobenzyl)morpholin-2-yl]methyl}-2-[5-methyl-2-(3-methylthien-2-yl)-1,3-oxazol-4-yl]acetamide | Example 41 | LC-MS(System A): Rt 2.95 mins. Mass Spectrum m/z 494[MH$^+$]. |
| 204 | N-{[(2S)-4-(3,4-dichlorobenzyl)morpholin-2-yl]methyl}-2-[2-(1,3-dimethyl-1H-pyrazol-5-yl)-5-methyl-1,3-oxazol-4-yl]acetamide | Example 41 | LC-MS(System A): Rt 2.63 mins. Mass Spectrum m/z 492 [MH$^+$]. |
| 205 | 2-[2-(3-chlorothien-2-yl)-5-methyl-1,3-oxazol-4-yl]-N-{[(2S)-4-(3,4-dichlorobenzyl)morpholin-2-yl]methyl}acetamide | Example 41 | LC-MS(System A): Rt 2.93 mins. Mass Spectrum m/z 514,516[MH$^+$]. |
| 206 | N-({(2S)-4-[(5-chlorothien-2-yl)methyl]morpholin-2-yl}methyl)-2-(5-phenyl-2H-tetraazol-2-yl)acetamide | Example 41 | LC-MS(System A): Rt 2.69 mins. Mass Spectrum m/z 433[MH$^+$]. |
| 207 | N-{[(2S)-4-(3-cyanobenzyl)morpholin-2-yl]methyl}-2-[2-(4-fluorophenyl)-5-methyl-1,3-oxazol-4-yl]acetamide | Example 54 | LC-MS(System A): Rt 2.55 mins. Mass Spectrum m/z 449[MH$^+$]. |
| 208 | N-{[(2S)-4-(2,1,3-benzoxadiazol-5-ylmethyl)morpholin-2-yl]methyl}-2-[2-(4-fluorophenyl)-5-methyl-1,3-oxazol-4-yl]acetamide | Example 54 | LC-MS(System A): Rt 2.80 mins. Mass Spectrum m/z 466[MH$^+$]. |
| 209 | 2-[2-(4-fluorophenyl)-5-methyl-1,3-oxazol-4-yl]-N-{[(2S)-4-(2,3,4-trifluorobenzyl)morpholin-2-yl]methyl}acetamide | Example 54 | LC-MS(System A): Rt 2.78 mins. Mass Spectrum m/z 478[MH$^+$]. |
| 210 | 2-[2-(4-fluorophenyl)-5-methyl-1,3-oxazol-4-yl]-N-({(2S)-4-[4-fluoro-3-(trifluoromethyl)benzyl]morpholin-2-yl}methyl)acetamide | Example 54 | LC-MS(System A): Rt 2.89 mins. Mass Spectrum m/z 510[MH$^+$]. |
| 211 | N-{[(2S)-4-(3,4-dichlorobenzyl)morpholin-2-yl]methyl}-2-{5-methyl-2-[4-(methylsulfonyl)phenyl]-1,3-oxazol-4-yl}acetamide | Example 56 | LC-MS(System A): Rt 2.62 mins. Mass Spectrum m/z 552[MH$^+$]. |
| 212 | N-{[(2S)-4-(3,4-dichlorobenzyl)morpholin-2-yl]methyl}-2-(5-methyl-2-phenyl-1,3-thiazol-4-yl)acetamide | Example 41 | LC-MS(System A): Rt 2.97 mins. Mass Spectrum m/z 490[MH$^+$]. |
| 213 | N-{[(2S)-4-(3,4-dichlorobenzyl)morpholin-2-yl]methyl}-2-(5-methyl-2-pyrazin-2-yl-1,3-thiazol-4-yl)acetamide | Example 41 | LC-MS(System A): Rt 2.51 mins. Mass Spectrum m/z 492[MH$^+$]. |

Example 214

N-({(2S)-4-[3-(4-chloarophenyl)propyl]morpholin-2-yl}methyl)-2-[2-4-flourophennyl)-5-menthyl-1,3-oxazol-4-yl]acetamide A mixture of Intermediate 28 (0.04 g), 3-(4-chlorophenyl) propanal (0.026 g) and acetic acid (0.02 ml) in dichloromethane (4 ml) was treated with sodium triacetoxyborohydride (0.080 g). The mixture was stirred at 20° C. for 72 h. The mixture was partitioned between chloroform (6 ml) and saturated aqueous sodium hydrogen carbonate (6 ml). The phases were separated and the organic phase applied to an ion exchange cartridge (2 g Isolute SCX, prewashed with methanol). The SCX cartridge was eluted with methanol (10 ml) followed by 10% 0.880 ammonia in methanol (10 ml) and the appropriate fractions were concentrated in vacuo to give the title compound as a colourless gum (0.055 g).

LCMS (system A) R$_t$ 2.65 min Mass Spectrum m/z 486 [MH$^+$].

Examples 215-219

| | Name | Preparation analogous to | Characterising Data |
|---|---|---|---|
| 215 | 2-(2-cyclopropyl-5-methyl-1,3-oxazol-4-yl)-N-{[(2S)-4-(3,4-dichlorobenzyl)morpholin-2-yl]methyl}acetamide | Example 158 | LC-MS(System A): Rt 2.48 mins. Mass Spectrum m/z 438[MH$^+$]. |
| 216 | N-{[(2S)-4-(3,4-dichlorobenzyl)morpholin-2-yl]methyl}-2-(2-isobutyl-5-methyl-1,3-oxazol-4-yl)acetamide | Example 158 | LC-MS(System A): Rt 2.70 mins. Mass Spectrum m/z 454[MH$^+$]. |
| 217 | N-{[(2S)-4-(3,4-dichlorobenzyl)morpholin-2-yl]methyl}-2-[5-methyl-2-(2-methylprop-1-enyl)-1,3-oxazol-4-yl]acetamide | Example 158 | LC-MS(System A): Rt 2.71 mins. Mass Spectrum m/z 452[MH$^+$]. |
| 218 | N-{[(2S)-4-(3,4-dichlorobenzyl)morpholin-2-yl]methyl}-2-(5-methyl-2-pyridin-2-yl-1,3-oxazol-4-yl)acetamide compound with formic acid (1:1) | Example 158 | LC-MS(System A): Rt 2.38 mins. Mass Spectrum m/z 475[MH$^+$]. |
| 219 | N-{[(2S)-4-(3,4-dichlorobenzyl)morpholin-2-yl]methyl}-2-[5-(4-fluorophenyl)-2H-tetraazol-2-yl]acetamide | Example 41 | LC-MS(System A): Rt 2.85 mins. Mass Spectrum m/z 479[MH$^+$]. |

Example 220

N-{[(2S)-4-(3,4-Dichlorobenzyl)morpholin-2-yl]methyl}-2-[5-(4-fluorophenyl)-1,2,4oxadiazol-3-yl]acetamide A mixture of Intermediate 38 (0.024 g), Intermediate 9(0.025 g), and 1-methyl-2-pyrrolidinone (1 drop) was subjected was subjected to irradiation in a 600 W microwave oven on full power for 4 mins. The reaction mixture was dissolved in methanol and applied to an ion exchange cartridge (2 g Isolute SCX, pre-conditioned with methanol). Elution with methanol (3 column volumes) followed 10% 0.880 ammonia in methanol (2 column volumes) and evaporation of the first basic fraction in vacuo gave the crude product. Purification by Biotage flash column chromatography on silica gel (8 g cartridge), eluting with 100:8:1 dichloromethane/ethanol/0.880 ammonia, gave the title compound as a white solid (0.025 g).

LCMS (System A) R$_t$ 2.85 min Mass Spectrum m/z 479, 481 [MH+]

Examples 221-224

| | Name | Preparation analogous to | Characterising Data |
|---|---|---|---|
| 221 | N-{[(2S)-4-(2,1,3-benzothiadiazol-5-ylmethyl)morpholin-2-yl]methyl}-2-[2-(4-fluorophenyl)-5-methyl-1,3-oxazol-4-yl]acetamide | Example 54 | LC-MS(System A): Rt 2.51 mins. Mass Spectrum m/z 482[MH$^+$]. |
| 222 | 4-{4-[2-({[(2S)-4-(3,4-dichlorobenzyl)morpholin-2-yl]methyl}amino)-2-oxoethyl]-5-methyl-1,3-oxazol-2-yl}-N,N-dimethylbenzamide | Example 56 | LC-MS(System A): Rt 2.50 mins. Mass Spectrum m/z 545[MH$^+$]. |
| 223 | 2-{2-[4-(acetylamino)phenyl]-5-methyl-1,3-oxazol-4-yl}-N-{[(2S)-4-(3,4-dichlorobenzyl)morpholin-2-yl]methyl}acetamide | Example 56 | LC-MS(System A): Rt 2.54 mins. Mass Spectrum m/z 531[MH$^+$]. |
| 224 | N-{[(2S)-4-(1,2,3-benzothiadiazol-6-ylmethyl)morpholin-2-yl]methyl}-2-[2-(4-fluorophenyl)-5-methyl-1,3-oxazol-4-yl]acetamide | Example 214 | LC-MS(System A): Rt 2.59 mins. Mass Spectrum m/z 482[MH$^+$]. |

Example 225

N-{[(2S)-4-(3,4-dichlorobenzyl)morpholin-2-yl]methyl}pentanamide

A solution of Intermediate 9 (0.028 g) in dichloromethane (2 ml) containing a suspension of polyvinyl pyridine (0.1 g) was treated with valeryl chloride (0.018 ml), and the mixture was shaken at 20° C. for 16 h. Tris(2-aminoethyl)amine polystyrene scavenger resin (Argonaut Technologies, 4.46 mmol/g; 0.067 g) was added, and the mixture was shaken at 20° C. for 2 h. The mixture was filtered and the filtrate applied directly to a silica gel cartridge (1 g Varian Bond Elut). Elution with chloroform, ether, and ethyl acetate gave the title compound 0.0225 g).

LC-MS (System A) Rt 2.43 mins. Mass Spectrum m/z 359 [MH$^+$].

Examples 226-238

| | Name | Preparation analogous to | Characterising Data |
|---|---|---|---|
| 226 | N-{[(2S)-4-(3,4-dichlorobenzyl)morpholin-2-yl]methyl}-4-methylpentanamide | Example 225 | LC-MS(System A): Rt 2.58 mins. Mass Spectrum m/z 373[MH$^+$]. |
| 227 | N-({4-[3-(3,4-dichlorophenyl)propyl]morpholin-2-yl}methyl)-2-phenoxyacetamide | Example 1 | LC-MS(System A): Rt 2.76 mins. Mass Spectrum m/z 437[MH$^+$]. |
| 228 | 2-cyclohexyl-N-{[4-(3,4-dichlorobenzyl)morpholin-2-yl]methyl}acetamide trifluoroacetate | Example 1 | LC-MS(System A): Rt 2.81 mins. Mass Spectrum m/z 399[MH$^+$]. |
| 229 | 2-(4-chlorophenyl)-N-{[4-(3,4-dichlorobenzyl)morpholin-2-yl]methyl}propanamide | Example 1 | LC-MS(System A): Rt 3.00 mins. Mass Spectrum m/z 443[MH$^+$]. |
| 230 | N-{[4-(3,4-dichlorobenzyl)morpholin-2-yl]methyl}-2-(1,1-dioxidothiomorpholin-4-yl)acetamide | Example 1 | LC-MS(System A): Rt 2.39 mins. Mass Spectrum m/z 450[MH$^+$]. |
| 231 | 2-[2-(4-fluorophenyl)-5-methyl-1,3-oxazol-4-yl]-N-({(2S)-4-[2-(4-fluorophenyl)-2-oxoethyl]morpholin-2-yl}methyl)acetamide | Example 54 | LC-MS(System A): Rt 2.58 mins. Mass Spectrum m/z 470[MH$^+$]. |
| 232 | N-({(2S)-4-[(3-chloro-1-benzothien-2-yl)methyl]morpholin-2-yl}methyl)-2-[2-(4-fluorophenyl)-5-methyl-1,3-oxazol-4-yl]acetamide | Example 54 | LC-MS(System A): Rt 3.46 mins. Mass Spectrum m/z 514[MH$^+$]. |
| 233 | 2-[2-(4-fluorophenyl)-5-methyl-1,3-oxazol-4-yl]-N-{[(2S)-4-(2-methylprop-2-enyl)morpholin-2-yl]methyl}acetamide | Example 54 | LC-MS(System A): Rt 2.37 mins. Mass Spectrum m/z 488[MH$^+$]. |
| 234 | 2-[2-(4-fluorophenyl)-5-methyl-1,3-oxazol-4-yl]-N-{[(2S)-4-(1-phenylethyl)morpholin-2-yl]methyl}acetamide | Example 54 | LC-MS(System A): Rt 2.48 mins. Mass Spectrum m/z 438[MH$^+$]. |
| 235 | N-{[(2S)-4-(3-cyano-4-fluorobenzyl)morpholin-2-yl]methyl}-2-[2-(4-fluorophenyl)-5-methyl-1,3-oxazol-4-yl]acetamide | Example 54 | LC-MS(System A): Rt 2.59 mins. Mass Spectrum m/z 467[MH$^+$]. |
| 236 | N-{[(2S)-4-(3,4-dichlorobenzyl)morpholin-2-yl]methyl}-2-[2-(4-fluorophenyl)-5-isopropyl-1,3-oxazol-4-yl]acetamide | Example 41 | LC-MS(System A): Rt 3.16 mins. Mass Spectrum m/z 520[MH$^+$]. |
| 237 | N-{[(2S)-4-(3,4-dichlorobenzyl)morpholin-2-yl]methyl}cyclopropane carboxamide | Example 225 | LC-MS(System A): Rt 2.22 mins. Mass Spectrum m/z 343[MH$^+$]. |
| 238 | N-({(2S)-4-[2-(3-chlorophenoxy)ethyl]morpholin-2-yl}methyl)-2-[2-(4-fluorophenyl)-5-methyl-1,3-oxazol-4-yl]acetamide | Example 54 | LC-MS(System A): Rt 2.72 mins. Mass Spectrum m/z 488[MH$^+$]. |

Example 239

N-{[(2S)-4-(3,4-dichlorobenzoyl)morpholin-2-yl]methyl}-2-[2-(4-fluorophenyl)-5-methyl-1,3-oxazol-4-yl]acetamide A mixture of Intermediate 12 (0.015 g), 1-hydroxybenzotriazole (0.0097 g), 1-(3-dimethylaminopropyl)-3-ethylcarbodiimide hydrochloride (0.012 g) and N,N-diisopropylethylamine (0.027 ml) in N,N-dimethylformamide (2 ml) was stirred at 20° C. for 10 min. The mixture was treated with Intermediate 31 (0.023 g) and stirred at 20° C. for 96 h. The mixture was applied sequentially to a sulphonic acid ion exchange cartridge (1 g SCX, prewashed with methanol) and Isolute$^R$ aminopropyl solid phase extraction cartridge (1 g), eluting both cartridges with methanol (5 ml). The solvent was removed in vacuo to give the title compound as a yellow gum (0.032 g).

LCMS (system A) R$_t$ 3.3 min Mass Spectrum m/z 506 [MH$^+$]

Example 240 tert-butyl 4-[3-({[(2S)-4-(3,4-dichlorobenzyl)morpholin-2-yl]methyl}amino)-3-oxopropyl]piperidine-1-carboxylate Example 240 was prepared in an analogous manner to Example 44 from 3-[1-(tert-butoxycarbonyl)piperidin-4-yl]propanoic acid.

LC-MS (System A) Rt 2.89 mins Mass Spectrum m/z 514 [MH$^+$]

Biological Data

The compounds of the Examples were tested in the CCR-3 binding and/or eosinophil chemotaxis assays (assays (a) and (b)) and results were obtained as follows:

| Example | CCR-3 Binding Assay (pIC50) | CCR-3 Eosinophil Chemotaxis Assay (fpKi) |
|---|---|---|
| 2 | | 6.51 |
| 3 | | 7.15 |
| 5 | 7.11 | |
| 6 | 6.86 | |
| 7 | 7.82 | |
| 8 | 6.84 | |
| 10 | 6.80 | |
| 12 | | 6.82 |
| 13 | 6.62 | |
| 14 | 6.47 | |
| 17 | | 6.24 |
| 19 | 6.08 | |
| 22 | 6.96 | |
| 25 | 7.22 | |
| 27 | | 7.39 |
| 31 | 6.29 | |
| 32 | | 7.32 |
| 35 | 6.81 | |
| 37 | | 7.97 |
| 38 | 7.00 | |
| 39 | | 8.31 |
| 41 | | 7.99 |
| 42 | | 9.32 |
| 44 | 8.17 | |
| 45 | 7.88 | |
| 46 | 7.14 | |
| 49 | | 8.07 |
| 53 | 8.39 | |
| 54 | 7.62 | 7.96 |
| 55 | 6.40 | |
| 162 | 7.9 | 8.2 |

Compounds of Examples 1, 4, 9, 11, 15-16, 18, 20-21, 23-24, 26, 28-30, 33-34, 36, 40, 43, 47-48, 50-52, 56-161 and 163-240 were also tested in CCR-3 binding assay (assay (a)) and achieved a pIC50 value greater than 5.0.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The invention claimed is:

1. A compound N-{[(2S)-4-(3,4-dichlorobenzyl)morpholin-2-yl]methyl}cyclopropane carboxamide; or a salt thereof.

* * * * *